US007084106B1

(12) United States Patent \
Kotwal et al.

(10) Patent No.: US 7,084,106 B1 \
(45) Date of Patent: Aug. 1, 2006

(54) APPLICATION OF A VIRAL COMPLEMENT INHIBITORY PROTEIN IN THE TREATMENT AND DIAGNOSIS OF ALZHEIMER'S DISEASE

(75) Inventors: Girish J. Kotwal, Louisville, KY (US); James Daly, IV, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 09/889,624

(22) PCT Filed: Jan. 19, 2000

(86) PCT No.: PCT/US00/01115

§ 371 (c)(1), \
(2), (4) Date: Nov. 7, 2001

(87) PCT Pub. No.: WO00/43027

PCT Pub. Date: Jul. 27, 2000

Related U.S. Application Data

(60) Provisional application No. 60/116,328, filed on Jan. 19, 1999.

(51) Int. Cl.
*A61K 38/00* (2006.01)
*A61K 31/44* (2006.01)
*A61K 31/135* (2006.01)

(52) U.S. Cl. .................. 514/2; 514/297; 514/299; 514/648

(58) Field of Classification Search .............. 514/2, 514/297, 299, 648 \
See application file for complete search history.

(56) References Cited

U.S. PATENT DOCUMENTS

| 4,609,647 | A |  | 9/1986 | Growdon et al. |
| 5,157,110 | A |  | 10/1992 | Kotwal et al. |
| 5,187,268 | A |  | 2/1993 | Kotwal et al. |
| 5,807,671 | A | * | 9/1998 | Soreq et al. ............ 435/6 |
| 5,855,882 | A |  | 1/1999 | Li et al. |

OTHER PUBLICATIONS

Daly J 4th, Kotwal GJ. Pro-inflammatory complement activation by the A beta peptide of Alzheimer's disease is biologically significant and can be blocked by vaccinia virus complement control protein. Neurobiol Aging. 1998 Nov.-Dec.;19(6):619-27.*

Janus C, Westaway D. Transgenic mouse models of Alzheimer's disease. Physiol Behav. 2001 Aug.;73(5):873-86.*

Adams, "Alzheimer's Disease Research: A Game of Connect the Dots," *Gerontology*, 1997, 43:8-19.

Beal et al., "Alzheimer's Disease and Other Dementias," *Harrison's Principles of Internal Medicine*, 13th Edition, vol. 2, Chapter 370, pp. 2269-2275, 1998.

Beyreuther and Masters, "Serpents on the road to dementia and death," *Nature Med.*, 1997, 3(7):723-725.

Breitner et al., "Delayed Onset of Alzheimer's Disease With Nonsteroidal Anti-Inflammatory and Histamine H2 Blocking Drugs," *Neurobiol. Aging*, 1995, 16(4):523-530.

Buxbaum and Greengard, "Regulation of APP Processing by Intra- and Intercellular Signals," *Ann. N.Y. Acad. Sci.*, 1996, 777:327-331.

Cheng, "A heparin-binding protein in porcine seminal plasma stimulates neurite outgrowth on neuroblastoma cells in culture," *Neurosci. Lett.*, 1992, 142:77-80.

Citron et al., "Mutant presenilins of Alzheimer's disease increase production of 42-residue amyloid β-protein in both transfected cells and transgenic mice," *Nature Med.*, 1997, 3(1):67-72.

Corder et al., "Gene Dose of Apolipoprotein E Type 4 Allele and the Risk of Alzheimer's Disease in Late Onset Families," *Science*, 1993, 261:921-923.

Cotman et al., "β-Amyloid Converts an Acute Phase Injury Response to Chronic Injury Responses," *Neurobiol. Aging*, 1996, 17(5):723-731.

Cribbs et al., "Complement activation by cross-linked truncated and chimeric full-length β-amyloid," *NeuroReport*, 1997, 8:3457-3462.

Dragunow and Preston, "The role of inducible transcription factors in apoptic nerve cell death," *Brain Res. Rev.*, 1995, 21:1-28.

(Continued)

*Primary Examiner*—Joseph Murphy \
(74) *Attorney, Agent, or Firm*—Fish & Richardson P.C., P.A.

(57) ABSTRACT

The present invention provides a novel treatment for senile dementia (Alzheimer's Type), comprising administering an anti-complement protein to a patient in need of such treatment in an amount sufficient to inhibit the complement cascade and thereby inhibit the production or enlargement of amyloid plaques in the brain of the patient. The present invention further provides pharmaceutical compositions comprising anti-complement protein, or derivatives thereof, and/or pharmaceutically acceptable salts thereof in a variety of unique pharmaceutical dosage forms.

6 Claims, 22 Drawing Sheets

OTHER PUBLICATIONS

Figure 1B:
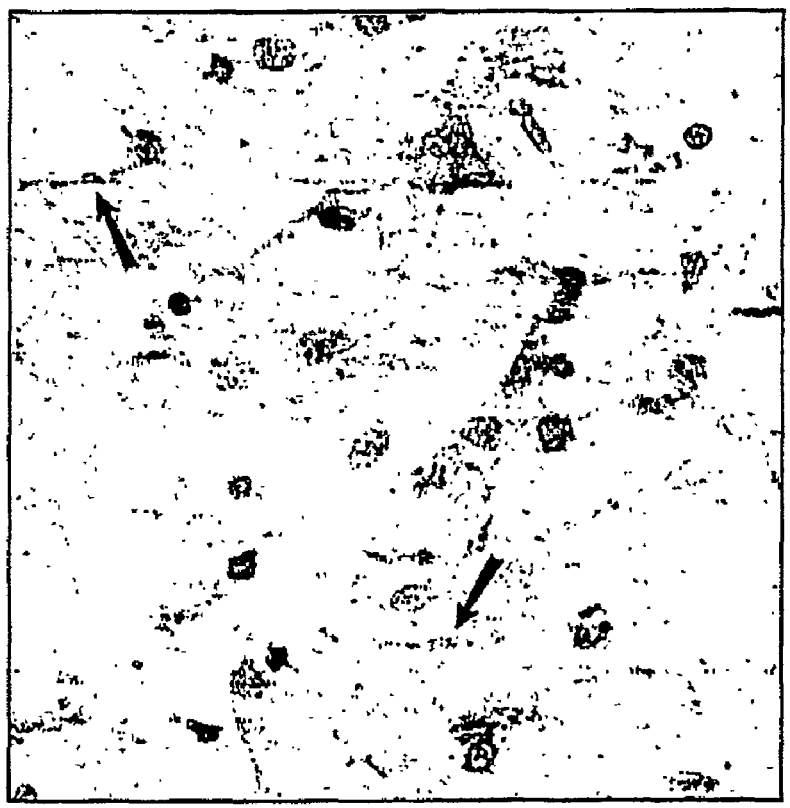

Elkabes et al., "Brain Microglia/Macrophages Express Neurotrophins that Selectively Regulate Microglial Proliferation and Function," *J. Neurosci.*, 1996, 16:2508-2521.

Farias et al., "Immunological characterization of epitopes on tau of Alzheimer's type and chemically modified tau," *Mol. Cell. Biochem.*, 1997, 168:59-66.

Goebel et al., "The Complete DNA Sequence of Vaccinia Virus," *Virology*, 1990, 179(1):247-266.

Jiang et al., "βAmyloid Activates Complement by Binding to a Specific Region of the Collagen-Like Domain of the Clq A Chain," *J. Immunol.*, 1994, 152(10):5050-5059.

Kotwal and Moss, "Vaccinia virus encodes a secretory polypeptide structurally related to complement control proteins," *Nature*, 1988, 335:176-178.

Kotwal et al., "The inflammation modulatory protein (IMP) of cowpox virus drastically diminishes the tissue damage by down-regulating cellular infiltration resulting from complement activation," *Mol. Cell. Biochem.*, 1998, 185:39-46.

Kotwal et al., "Inhibition of the Complement Cascade by the Major Secretory Protein of Vaccinia Virus," *Science*, 1990, 250:827-830.

Kotwal et al., "Intracellular Detection of the C-Terminal Tail Containing APP Polypeptides in AD Brain Tissue," *Soc. Neurosci. Abstr.*, 1996, 22:502, Abstract No. 204.2.

Kotwal et al., "Mapping and Insertional mutagenesis of a Vaccinia Virus Gene Encoding a 13,800-Da Secreted Protein," *Virology*, 1989, 171(2):579-587.

Kotwal et al., "Vaccinia virus complement control protein is a virokine with lysozyme-like heparin-binding activity: possible implications in prolonged evasion of host immune response," *10th International Congress of Immunology*, New Delhi, India, Nov. 1-6 1998, 1:315-320.

Kotwal, "The Great Escape. Immune Evasion by Pathogens," *The Immunologist*, 1996, 4:157-164.

Mackenzie and Munoz, "Nonsteroidal anti-inflammatory drug use and Alzheimer-type pathology in aging," *Neurology*, 1998, 50(4):986-990.

Mahley et al., "Apolipoprotein E. Structure, Function, and Possible Roles in Alzheimer's Disease," *Ann. N. Y. Acad. Sci.*, 1996, 777:139-145.

Mann et al., "Microglial cells and amyloid β protein (Aβ) deposition: association with $A\beta_{40}$-containing plaques," *Acta Neuropathol.*, 1995, 90(5):472-477.

Massung et al., "Analysis of the Complete Genome of Smallpox Variola Major Virus Strain Bangledesh-1975," *Virology*, 1994, 201(2):215-240.

Massung et al., "Terminal Region Sequence Variations in Variola Virus DNA," *Virology*, 1996, 221:291-300.

McGeer et al., "Arthritis and anti-inflammatory agents as possible protective factors for Alzheimer's disease: A review of 17 epidemiologic studies," *Neurology*, 1996, 47:425-432.

McKenzie et al., "Regulation of Complement Activity by Vaccinia Virus Complement-Control Protein," *J. Infect. Dis.*, 1992, 166:1245-1250.

Messing et al., "A system for shotgun DNA sequencing," *Nucl. Acids Res.*, 1981, 9:309-321.

Miller et al., "Severe and Prolonged Inflammatory Response to Localized Cowpox Virus Infection in Footpads of C5-Deficient Mice: Investigation of the Role of Host Complement in Poxvirus Pathogenesis," *Cell. Immunol.*, 1995, 162:326-332.

Miller et al., "The Cowpox Virus-Encoded Homolog of the Vaccinia Virus Complement Control Protein Is an Inflammation Modulatory Protein," *Virology*, 1997, 229(1):126-133.

Mulligan and Berg, "Expression of a Bacterial Gene in Mammalian Cells," *Science*, 1980, 209:1422-1427.

Palmert et al. "Amyloid Protein Precursor Messenger RNAs: Differential Expression in Alzheimer's Disease," *Science*, 1988, 241:1080-1084.

Peskind, "Neurobiology of Alzheimer's Disease," *J. Clin. Psychiatry*, 1996, 57:(Suppl. 14): 5-8.

Rebeck et al., "Multiple, Diverse Senile Plaque—associated Proteins Are Ligands of an Apolipoprotein E Receptor, the $\alpha_2$-Macroglobulin Receptor/Low-Density-Lipoprotein Receptor-related Protein," *Ann. Neurol.*, 1995, 37(2):211-217.

Rohan de Silva and Patel, "Presenilins and early-onset familial Alzheimer's disease," *NeuroReport*, 1997, 8(8):i-xii.

Roses, "Alzheimer's Disease: The Genetics of Risk," *Hosp. Pract.*, 1997, 32(7):51-69.

Shchelkunov et al., "The Genomic Sequence Analysis of the Left and Right Species-Specific Terminal Region of a Cowpox Virus Strain Reveals Unique Sequences and a Cluster of Intact ORFs for Immunomodulatory and Host Range Proteins," *Virology*, 1998, 243:432-460.

Schellenberg et al., "$APP_{717}$, $APP_{693}$, and PRIP Gene Mutations Are Rare in Alzheimer Disease," *Am. J. Hum. Genet.*, 1991, 49:511-517.

Schmidt et al., "Chemical and Immunological Heterogeniety of Fibrillar Amyloid in Plaques of Alzheimer's Disease and Down's Syndrome Brains Revealed by Confocal Microscopy," *Am. J. Pathol.*, 1995, 147(2):503-515.

Selkoe, "The Role of APP Processing and Trafficking Pathways in the Formation of Amyloid β-Protein[a]," *Ann. N.Y. Acad. Sci.*, 1996, 777:57-64.

Selkoe, "Amyloid β-Protein and the Genetics of Alzheimer's Disease," *J. Biol. Chem.*, 1996, 271(31):18295-18298.

Selkoe, "Alzheimer's Disease: Genotypes, Phenotype, and Treatments," *Science*, 1997, 275:630-631.

Singh, "Neuroautoimmunity: Pathogenic Implications for Alzheimer's Disease," *Gerontology*, 1997, 43:79-94.

Sisodia, "β-Amyloid precursor protein cleavage by a membrane-bound protease," *Proc. Natl. Acad. Sci. USA*, 1992, 89:6075-6079.

Sisodia et al., "Evidence that β-Amyloid Protein in Alzheimer's Disease Is Not Derived by Normal Processing," *Science*, 1990, 248:492-495.

Southern and Berg, "Transformation of Mammalian Cells to Antibiotic Resistance with a Bacterial Gene Under Control of the SV40 Early Region Promoter," *J. Molec. Appl. Genet.*, 1982, 1:327-341.

Spillantini et al., "Comparison of the neurofibrillary pathology in Alzheimer's disease and familial presenile dementia with tangles," *Acta Neuropathol.*, 1996, 92:42-48.

Strittmatter and Roses, "Apolipoprotein E and Alzheimer's Disease," *Annu. Rev. Neurosci.*, 1996, 19:53-77.

Strittmatter et al., "Binding of human apolipoprotein E to synthetic amyloid β peptide: Isoform-specific effect and implications for late-onset Alzheimer disease," *Proc. Natl. Acad. Sci. USA*, 1993, 90:8098-8102.

Strittmatter et al., "Isoform-specific interactions of apolipoprotein E with microtubule-associated protein tau: Implications for Alzheimer disease," *Proc. Natl. Acad. Sci. USA*, 1994, 91:11183-11186.

Sugden et al., "A Vector That Replicates as a Plasmid and Can Be Efficiently Selected in B-Lymphoblasts Transformed by Epstein-Barr Virus," *Mol. Cell. Biol.*, 1985, 5(2):410-413.

Takashima et al., "Localization of Alzheimer-Associated Presenilin 1 in Transfeceted COS-7 Cells," *Biochem. Biophys. Res. Comm.*, 1996, 227:423-426.

Tanzi et al., "The Presenilin Genes and Their Role in Early-Onset Familial Alzheimer's Disease," *Alzheimer's Dis. Rev.*, 1996, 1:90-98.

Thinakaran et al., "Endoproteolysis of Presenilin 1 and Accumulation of Processed Derivatives In Vivo," *Neuron*, 1996, 17:181-190.

Van Broeckhoven, "Molecular Genetics of Alzheimer Disease: Identification of Genes and Gene Mutations," *Eur. Neurol.*, 1995, 35:8-19.

Velazquez et al., "Aspartate residue 7 in amyloid β-protein is critical for classical complement pathway activation: Implications for Alzheimer's disease pathogenesis," *Nature Med.*, 1997, 3:77-79.

Webster et al., "Multivalent Binding of Complement Protein C1Q to the Amyloid β-Peptide (Aβ) Promotes the Nucleation Phase of Aβ Aggregation," *Biochem. Biophys. Res. Comm.*, 1995, 217(3):869-875.

Webster et al., "Aggregation State-Dependent Activation of the Classical Complement Pathway by the Amyloid β Peptide," *J. Neurochem.*, 1997, 69:388-398.

Webster et al., "Molecular and Cellular Characterization of the Membrane Attack Complex, C5b-9, in Alzheimer's Disease," *Neurobiol. Aging*, 1997, 18(4):415-421.

Webster et al., "Charge-Based Binding of Complement Component C1q to the Alzheimer Amyloid β-Peptide," *Am. J. Pathol.*, 1997, 150(5):1531-1536.

Webster and Rogers, "Relative Efficacies of Amyloid β Peptide (Aβ) Binding Proteins in Aβ Aggregation," *J. Neurosci. Res.*, 1996, 46:58-66.

Weidemann et al., "Formation of stable complexes between two Alzheimer's disease gene products: Presenilin-2 and β-amyloid precursor protein," *Nat. Med.*, 1997, 3(3):328-332.

Wiles et al., "NMR Studies of a Viral Protein that Mimics the Regulators of Complement Activation," *J. Mol. Biol.*, 1997, 272:253-265.

Pasinetti, G.M., "Inflammatory Mechanisms in Neurodegeneration and Alzheimer's Disease: The Role of the Complement System" Neurobiology of Aging, 1996, vol. 17, No. 5, pp. 707-716, see whole reference.

* cited by examiner

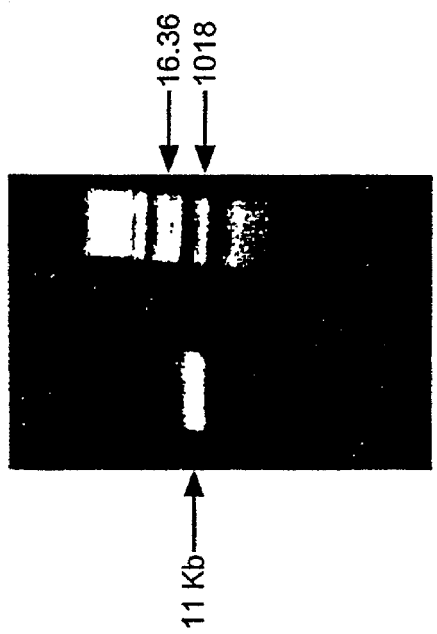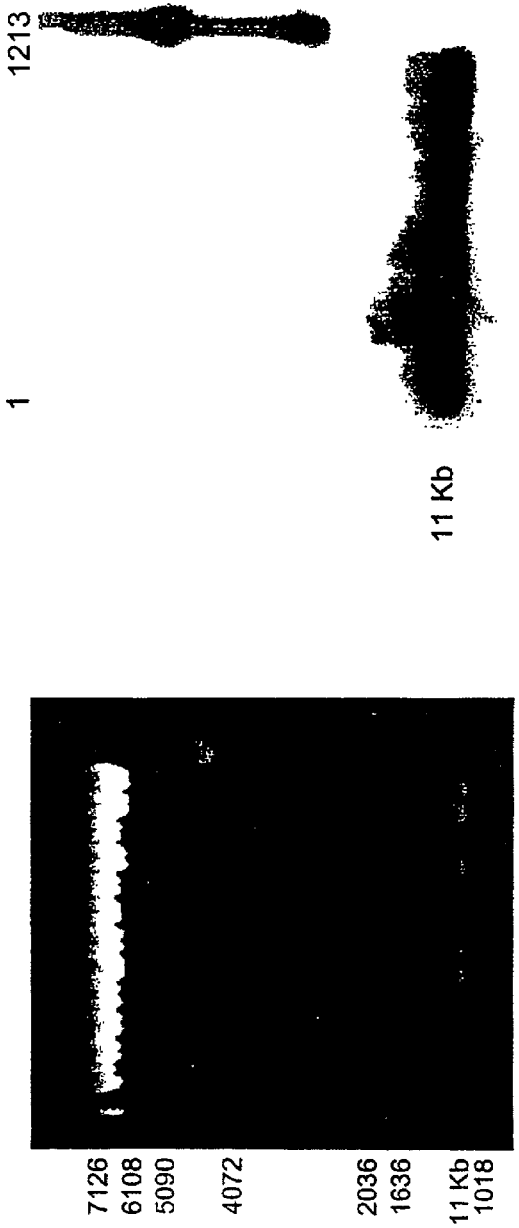

APP C-terminus Sequence Data

```
5'TAAAAAACGTCTAGGCCCCCCGAACCACGGGGACGTGGTTTTCCTTTGAAAAAC
  ACGATAATACCATGGATGCAGAATTCCGACATGACTCAGGATATGAAGTTCATC
             M  D  A  E  F  R  H  D  S  G  Y  E  V  H  H
  ATCAAAAATTGGTGTTCTTTGCAGAAGATGTGGGTTCAAACAAAGGTGCAATCAT
   Q  K  L  V  F  F  A  E  D  V  G  S  N  K  G  A  I  I
  TGGACTCATGGTGGGCGGTGTTGTCATAGCGACAGTGATCGTCATCACCTTGGTG
   G  L  M  V  G  G  V  V  I  A  T  V  I  V  I  T  L  V
  ATGCTGAAGAAGAAACAGTACACATCCATTCATCATGGTGTGGTGGAGGTTGACG
   M  L  K  K  K  Q  Y  T  S  I  H  H  G  V  V  E  V  D  A
  CCGCTGTCACCCCAGAGGAGCGCCACCTGTCCAAGATGCAGCAGAACGGCTACGA
    A  V  T  P  E  E  R  H  L  S  K  M  Q  Q  N  G  Y  E
  AAATCCAACCTACAAGTTCTTTGAGCAGATGCAGAACTAGACCCCCGCCACAGCA
    N  P  T  Y  K  F  F  E  Q  M  Q  N  *
  GCCTCTGAAGTTGGACAGCAAAACCATTGCTTCACTACCCATCGGTGTCCATTTAT
  AGAATAATGTGGGAAGAAACAAACCCGTTTTATGATTTACTCATTATCGCCTTTTG
  ACAGCTGTGCTGTAACACAAGTAGATGCCTGAACTTGAATTAATCCACACATCAGT
  AATGTATTCTATCTCTCTTTACATTTTGGTCTCTATACTACATTATTAATGGGTTT
  TGTGTACTGTAAAGAATTTAGCTGTATCAAACTAGTGCATGAATAGATTCTCCT
  GATTATTTATCACATAGCCCCTTAGCCAGTTGTATATTATTCTTGTGGTTTGTGAC
  CCAATTAAGTCCTACTTTACATATGCTTTAAGAATCGATGGGGGATGCTTCATGTG
  AACGTGGGAGTTCAGCTGCTTCTCTTGCCTAAGTATTCCTTTCCTGATCACTATGC
  ATTTTAAAGTTAAACATTTTTAAGTATTTCAGATGCTTTAGAGAGATTTTTTTTCC
  ATGACTGCATTTTACTGTACAGATTGCTGCTTCTGCTATATTTGTGATATAGGAAT
  TAAGAGGATACACACGTTTGTTTCTTCGTGCCTGTTTTATGTGCACACATTAGGCA
  TTGAGACTTCAAGCTTTTCTTTTTTTGTCCACGTATCTTTGGGTCTTTGATAAAGA
  AAAGAATCCCTGTTCATTGTAAGCACTTTTACGGGGCGGGTGGGGAGGGGTGCTCT
  GCTGGTCGACGATCCGGCTGCTAACAAAGCCCGAAGGAAGCTGAGTTGGCTGCTG
  CCACCGCTGAGCAATAACTAGCATAACCCCTTGGGGCC3'
```

Legend

Text in *italics* is adjoining plasmid DNA.
*Bold Italicised* texts are restriction sites.
<u>Underlined</u> texts are forward and reverse primer sites used for sequencing.
Boxed text represents amino acid sequence for Aß peptide region.
(Boxed) text represents amino acid sequence for endosome targeting.
Highlighted text represents transmembrane domain.

FIG. 7

FIG. 15

```
                                                    (2,3) (2,3,4)
              (1-4)                                    ↑     ↑
              (1,2)
              (1,2,3)
VAC-COP C3L   CCTIPSRPINMKFKNSVETDANANYNIGDTIEYLCLPGYRKQKMGPIYAKCTGTGWTLFNQCI
VAC-WR  C21L  .......P.........T...GT.......SH..........................
CPV-GRI C17L  .................T...GT....-SH.............................
CPV-BRI IMP   .....................G....................................
VAR-BSH D15L  ...........................................................
VAR-IND D12L  ...........T...............................................
VAR-GAR B18L  ...........................................................
MPV-ZAI D15L  ......Y....................................................

VAC-COP C3L   KRRCPSPRDIDNGQLDIGGVDFGSSITYSCNSGYHLIGESKSYCELGSTGSMVWNPEAPICE
VAC-WR  C21L  ...K........................................................
CPV-GRI C17L  .................I.............E..........................
CPV-BRI IMP   ...........................................................
VAR-BSH D15L  .................H.........Q..Y.......K....................
VAR-IND D12L  .................H.........Y..Y.......K....................
VAR-GAR B18L  .................H.........Y..Y.......K....................
MPV-ZAI D15L  ...........................Y..............................
              (1,2)
              ↑
              (3,4)
VAC-COP C3L   SVKCQSPPSISNGRHNGYEDFYTDGSVVTYSCNSGYSLIGNSGVLCSGGEWSDPPTCQ
VAC-WR  C21L  ..........................................................
CPV-GRI C17L  ..........VT...............................................
CPV-BRI IMP   ........P........................IV........................
VAR-BSH D15L  ........L...............N.................N..............
VAR-IND D12L  ........L...............N.................N..............
VAR-GAR B18L  ........L...............N..........I.....M.N..............
MPV-ZAI D15L  ..........................................................
              (2,3) (1,2,3)                               (3,4) (2,3,4)
              ↓                                           ↓     ↓
VAC-COP C3L   IVKCPHPTISNGYLSSGFKRSYSYNDNVDFKCKYGYKLSGSSSTCSPGNTWKPELPKCVR
VAC-WR  C21L  ...................................................(1-4) ↓
CPV-GRI C17L  .......S.T...........H...............RH..........Q........
CPV-BRI IMP   .........L.............................T.........Q........
VAR-BSH D15L  .........L.............................T.........Q........
VAR-IND D12L  .........L.............................T.........Q........
VAR-GAR B18L  .........Y.............................T..................
MPV-ZAI D15L  ........-..........K.LAA...................................
```

| | Inhabition of Hemolysis | Heparin Binding Activity | K+R | %K+R | pI | # of Putative Sites (K/R X K/R) |
|---|---|---|---|---|---|---|
| VCP/IMP/SPICE | + | + | 23 | 9.43 | 8.80 | 4 |
| MPV Homolog of VCP | + | N/D | 16 | 8.00 | 7.22 | 3 |
| rVCP | + | + | 23 | 9.43 | 8.80 | 4 |
| rVCP SCR (2,3,4) | – | + | 16 | 8.79 | 7.22 | 2 |
| rVCP SCR (1,2) | – | + | 12 | 9.60 | 7.00 | 3 |
| rVCP SCR (2,3) | – | – | 7 | 5.83 | 4.41 | 1 |
| rVCP SCR (3,4) | – | + | 11 | 9.24 | 9.08 | 1 |

Short Consensus Repeats (SCR)

---C--P-------YF-C---C--------C---G-W-----A/P-C-

FIG. 16

SEQUENCE LISTING

<160> NUMBER OF SEQ ID NOS: 12

<210> SEQ ID NO 1
<211> LENGTH: 263
<212> TYPE: PRT
<213> ORGANISM: Vaccinia Virus

<400> SEQUENCE: 1

```
Met Lys Val Glu Ser Val Thr Phe Leu Thr Leu Leu Gly Ile Gly Cys
 1               5                  10                  15

Val Leu Ser Cys Cys Thr Ile Pro Ser Arg Pro Ile Asn Met Lys Phe
            20                  25                  30

Lys Asn Ser Val Glu Thr Asp Ala Asn Ala Asn Tyr Asn Ile Gly Asp
        35                  40                  45

Thr Ile Glu Tyr Leu Cys Leu Pro Gly Tyr Arg Lys Gln Lys Met Gly
    50                  55                  60

Pro Ile Tyr Ala Lys Cys Thr Gly Thr Gly Trp Thr Leu Phe Asn Gln
65                  70                  75                  80

Cys Ile Lys Arg Arg Cys Pro Ser Pro Arg Asp Ile Asp Asn Gly Gln
                85                  90                  95

Leu Asp Ile Gly Gly Val Asp Phe Gly Ser Ser Ile Thr Tyr Ser Cys
            100                 105                 110

Asn Ser Gly Tyr His Leu Ile Gly Glu Ser Lys Ser Tyr Cys Glu Leu
        115                 120                 125

Gly Ser Thr Gly Ser Met Val Trp Asn Pro Glu Ala Pro Ile Cys Glu
    130                 135                 140

Ser Val Lys Cys Gln Ser Pro Pro Ser Ile Ser Asn Gly Arg His Asn
145                 150                 155                 160

Gly Tyr Glu Asp Phe Tyr Thr Asp Gly Ser Val Val Thr Tyr Ser Cys
                165                 170                 175

Asn Ser Gly Tyr Ser Leu Ile Gly Asn Ser Gly Val Leu Cys Ser Gly
            180                 185                 190

Gly Glu Trp Ser Asp Pro Pro Thr Cys Gln Ile Val Lys Cys Pro His
        195                 200                 205

Pro Thr Ile Ser Asn Gly Tyr Leu Ser Ser Gly Phe Lys Arg Ser Tyr
    210                 215                 220

Ser Tyr Asn Asp Asn Val Asp Phe Lys Cys Lys Tyr Gly Tyr Lys Leu
225                 230                 235                 240

Ser Gly Ser Ser Ser Ser Thr Cys Ser Pro Gly Asn Thr Trp Lys Pro
                245                 250                 255

Glu Leu Pro Lys Cys Val Arg
            260
```

<210> SEQ ID NO 2

-continued

<211> LENGTH: 840
<212> TYPE: DNA
<213> ORGANISM: Vaccinia Virus

<400> SEQUENCE: 2
tttttattat ttgtacgatg tccaggataa catttttacg gataaataaa tatgaaggtg 60
gagagcgtga cgttcctgac attgttggga ataggatgcg ttctatcatg ctgtactatt 120
ccgtcacgac ccattaatat gaaatttaag aatagtgtgg agactgatgc taatgctaat 180
tacaacatag gagacactat agaatatcta tgtctacctg gatacagaaa gcaaaaaatg 240
ggacctatat atgctaaatg tacaggtact ggatggacac tctttaatca atgtattaaa 300
cggagatgcc catcgcctcg agatatcgat aatggccaac ttgatattgg tggagtagac 360
tttggctcta gtataacgta ctcttgtaat agcggatatc atttgatcgg tgaatctaaa 420
tcgtattgtg aattaggatc tactggatct atggtatgga atcccgaggc acctatttgt 480
gaatctgtta aatgccaatc ccctccatct atatccaacg gaagacataa cggatacgag 540
gatttttata ccgatgggag cgttgtaact tatagttgca atagtggata ttcgttgatt 600
ggtaactctg gtgtcctgtg ttcaggagga gaatggtccg atccacccac gtgtcagatt 660
gttaaatgtc cacatcctac aatatcaaac ggatacttgt ctagcgggtt taaaagatca 720
tactcataca acgacaatgt agactttaag tgcaagtacg gatataaact atctggttcc 780
tcatcatcta cttgctctcc aggaaataca tggaagccgg aacttccaaa atgtgtacgc 840

<210> SEQ ID NO 3
<211> LENGTH: 1205
<212> TYPE: DNA
<213> ORGANISM: Artificial Sequence
<220> FEATURE:
<223> OTHER INFORMATION: C-terminus (nucleotides 1786-3207) of amyloid
precursor protein (APP)

<400> SEQUENCE: 3
taaaaaacgt ctaggccccc cgaaccacgg ggacgtggtt ttcctttgaa aaacacgata 60
ataccatgga tgcagaattc cgacatgact caggatatga agttcatcat caaaaattgg 120
tgttctttgc agaagatgtg ggttcaaaca aaggtgcaat cattggactc atggtgggcg 180
gtgttgtcat agcgacagtg atcgtcatca ccttggtgat gctgaagaag aaacagtaca 240
catccattca tcatggtgtg gtggaggttg acgccgctgt caccccagag gagcgccacc 300
tgtccaagat gcagcagaac ggctacgaaa atccaaccta caagttcttt gagcagatgc 360
agaactagac cccgccacag cagcctctga agttggacag caaaaccatt tgcttcacta 420
cccatcggtg tccatttata gaataatgtg ggaagaaaca aacccgtttt atgatttact 480
cattatcgcc ttttgacagc tgtgctgtaa cacaagtaga tgcctgaact tgaattaatc 540
cacacatcag taatgtattc tatctctctt tacattttgg tctctatact acattattaa 600
tgggttttgt gtactgtaaa gaatttagct gtatcaaact agtgcatgaa tagattctct 660
cctgattatt tatcacatag ccccttagcc agttgtatat tattcttgtg gtttgtgacc 720
caattaagtc ctactttaca tatgctttaa gaatcgatgg gggatgcttc atgtgaacgt 780
gggagttcag ctgcttctct tgcctaagta ttcctttcct gatcactatg cattttaaag 840
ttaaacattt ttaagtattt cagatgcttt agagagattt tttttccatg actgcatttt 900
actgtacaga ttgctgcttc tgctatattt gtgatatagg aattaagagg atacacacgt 960
ttgtttcttc gtgcctgttt tatgtgcaca cattaggcat tgagacttca agcttttctt 1020

-continued

```
tttttgtcca cgtatctttg ggtctttgat aaagaaaaga atccctgttc attgtaagca    1080
cttttacggg gcgggtgggg aggggtgctc tgctggtcga cgatccggct gctaacaaag    1140
cccgaaagga agctgagttg gctgctgcca ccgctgagca ataactagca taaccccttg    1200
gggcc                                                                 1205
```

<210> SEQ ID NO 4
<211> LENGTH: 100
<212> TYPE: PRT
<213> ORGANISM: Artificial Sequence
<220> FEATURE:
<223> OTHER INFORMATION: C-terminus (nucleotides 1786-3207) of amyloid
      precursor protein (APP)

<400> SEQUENCE: 4

```
Met Asp Ala Glu Phe Arg His Asp Ser Gly Tyr Glu Val His His Gln
  1               5                  10                  15

Lys Leu Val Phe Phe Ala Glu Asp Val Gly Ser Asn Lys Gly Ala Ile
             20                  25                  30

Ile Gly Leu Met Val Gly Gly Val Val Ile Ala Thr Val Ile Val Ile
         35                  40                  45

Thr Leu Val Met Leu Lys Lys Lys Gln Tyr Thr Ser Ile His His Gly
     50                  55                  60

Val Val Glu Val Asp Ala Ala Val Thr Pro Glu Glu Arg His Leu Ser
 65                  70                  75                  80

Lys Met Gln Gln Asn Gly Tyr Glu Asn Pro Thr Tyr Lys Phe Phe Glu
                 85                  90                  95

Gln Met Gln Asn
            100
```

<210> SEQ ID NO 5
<211> LENGTH: 244
<212> TYPE: PRT
<213> ORGANISM: Vaccinia Virus, Copenhagen Strain

<400> SEQUENCE: 5

```
Cys Cys Thr Ile Pro Ser Arg Pro Ile Asn Met Lys Phe Lys Asn Ser
  1               5                  10                  15

Val Glu Thr Asp Ala Asn Ala Asn Tyr Asn Ile Gly Asp Thr Ile Glu
             20                  25                  30

Tyr Leu Cys Leu Pro Gly Tyr Arg Lys Gln Lys Met Gly Pro Ile Tyr
         35                  40                  45

Ala Lys Cys Thr Gly Thr Gly Trp Thr Leu Phe Asn Gln Cys Ile Lys
     50                  55                  60

Arg Arg Cys Pro Ser Pro Arg Asp Ile Asp Asn Gly Gln Leu Asp Ile
 65                  70                  75                  80

Gly Gly Val Asp Phe Gly Ser Ser Ile Thr Tyr Ser Cys Asn Ser Gly
                 85                  90                  95

Tyr His Leu Ile Gly Glu Ser Lys Ser Tyr Cys Glu Leu Gly Ser Thr
            100                 105                 110

Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
```

```
                        165                 170                 175
Ser Asp Pro Pro Thr Cys Gln Ile Val Lys Cys Pro His Pro Thr Ile
                180                 185                 190

Ser Asn Gly Tyr Leu Ser Ser Gly Phe Lys Arg Ser Tyr Ser Tyr Asn
            195                 200                 205

Asp Asn Val Asp Phe Lys Cys Lys Tyr Gly Tyr Lys Leu Ser Gly Ser
        210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 6
<211> LENGTH: 244
<212> TYPE: PRT
<213> ORGANISM: Vaccinia Virus, Western Reserve Strain

<400> SEQUENCE: 6

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly Gln Leu Asp Ile
65                  70                  75                  80

Gly Gly Val Asp Phe Gly Ser Ser Ile Thr Tyr Ser Cys Asn Ser Gly
                85                  90                  95

Tyr His Leu Ile Gly Glu Ser Lys Ser Tyr Cys Glu Leu Gly Ser Thr
            100                 105                 110

Gly Ser Met Val Trp Asn Pro Glu Ala Pro Ile Cys Glu Ser Val Lys
        115                 120                 125

Cys Gln Ser Pro Pro Ser Ile Ser Asn Gly Arg His Asn Gly Tyr Glu
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asp Pro Pro Thr Cys Gln Ile Val Lys Cys Pro His Pro Thr Ile
            180                 185                 190

Ser Asn Gly Tyr Leu Ser Ser Gly Phe Lys Arg Ser Tyr Ser Tyr Asn
        195                 200                 205

Asp Asn Val Asp Phe Lys Cys Lys Tyr Gly Tyr Lys Leu Ser Gly Ser
    210                 215                 220

Ser Ser Ser Thr Cys Ser Pro Gly Asn Thr Trp Lys Pro Glu Leu Pro
225                 230                 235                 240

Lys Cys Val Arg

<210> SEQ ID NO 7
<211> LENGTH: 240
<212> TYPE: PRT
<213> ORGANISM: Cowpox Virus, Russian Isolate From Human Patient

<400> SEQUENCE: 7
```

-continued

Cys Cys Pro Ile Pro Ser Arg Pro Ile Thr Met Lys Phe Lys Gly Thr
1               5                   10                  15

Val Asp Ser His Tyr Asn Ile Gly Asp Thr Ile Glu Tyr Leu Cys Leu
            20                  25                  30

Pro Gly Tyr Arg Lys Gln Lys Met Gly Pro Ile Tyr Ala Lys Cys Thr
        35                  40                  45

Gly Thr Gly Trp Thr Leu Phe Asn Gln Cys Ile Lys Arg Arg Cys Pro
50                      55                  60

Ser Pro Arg Asp Ile Asp Asn Gly Gln Leu Asp Ile Gly Gly Val Asp
65                  70                  75                  80

Phe Gly Ser Ser Ile Thr Tyr Ser Cys Asn Ser Gly Tyr His Leu Ile
                85                  90                  95

Gly Glu Ser Lys Ser Tyr Cys Glu Leu Gly Ser Thr Gly Ser Met Val
            100                 105                 110

Trp Asn Pro Glu Ala Pro Ile Cys Glu Ser Val Lys Cys Gln Ser Pro
        115                 120                 125

Pro Ser Ile Ser Asn Gly Arg His Asn Gly Tyr Glu Asp Phe Tyr Thr
130                 135                 140

Asp Gly Ser Val Val Thr Tyr Ser Cys Asn Ser Gly Tyr Ser Leu Ile
145                 150                 155                 160

Gly Asn Ser Gly Val Leu Cys Ser Gly Gly Glu Trp Ser Asp Pro Pro
                165                 170                 175

Thr Cys Gln Ile Val Lys Cys Pro His Pro Thr Ile Ser Asn Gly Tyr
            180                 185                 190

Leu Ser Ser Gly Phe Lys Arg Ser Tyr Ser Tyr Asn Asp Asn Val Asp
        195                 200                 205

Phe Lys Cys Lys Tyr Gly Tyr Lys Leu Ser Gly Ser Ser Ser Ser Thr
210                 215                 220

Cys Ser Pro Gly Asn Thr Trp Gln Pro Glu Leu Pro Lys Cys Val Arg
225                 230                 235                 240

<210> SEQ ID NO 8
<211> LENGTH: 244
<212> TYPE: PRT
<213> ORGANISM: Cowpox Virus, Brighton Strain

<400> SEQUENCE: 8

Cys Cys Thr Ile Pro Ser Arg Pro Ile Asn Met Lys Phe Lys Asn Ser
1               5                   10                  15

Val Gly Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
50                      55                  60

Arg Lys Cys Pro Ser Pro Arg Asp Ile Asp Asn Gly Gln Ile Asp Ile
65                  70                  75                  80

Gly Gly Val Glu Phe Gly Ser Ser Ile Thr Tyr Ser Cys Asn Ser Gly
                85                  90                  95

Tyr Gln Leu Ile Gly Glu Ser Lys Ser Tyr Cys Glu Leu Gly Tyr Thr
            100                 105                 110

Gly Ser Met Val Trp Asn Pro Glu Ala Pro Ile Cys Glu Ser Val Lys
        115                 120                 125

Cys Pro Ser Pro Pro Ser Val Thr Asn Gly Arg His Asn Gly Tyr Glu
130                 135                 140

-continued

```
Asp Phe Tyr Thr Asp Gly Ser Val Val Thr Tyr Ser Cys Asn Ser Gly
145                 150                 155                 160

Tyr Ser Leu Ile Gly Asn Ser Gly Ile Val Cys Ser Gly Gly Glu Trp
            165                 170                 175

Ser Asp Pro Pro Thr Cys Gln Ile Val Lys Cys Pro His Pro Ser Ile
        180                 185                 190

Thr Asn Gly Tyr Leu Ser Ser Gly Phe Lys Arg Ser Tyr Ser His Asn
    195                 200                 205

Asp Asn Val Asp Phe Lys Cys Arg His Gly Tyr Lys Leu Ser Gly Ser
210                 215                 220

Ser Ser Thr Cys Ser Pro Gly Asn Thr Trp Gln Pro Glu Leu Pro
225                 230                 235                 240

Lys Cys Val Arg

<210> SEQ ID NO 9
<211> LENGTH: 244
<212> TYPE: PRT
<213> ORGANISM: Variola Virus, Bangladesh Strain

<400> SEQUENCE: 9

Cys Cys Thr Ile Pro Ser Arg Pro Ile Asn Met Lys Phe Lys Asn Ser
1               5                   10                  15

Val Glu Thr Asp Ala Asn Ala Asn Tyr Asn Ile Gly Asp Thr Ile Glu
            20                  25                  30

Tyr Leu Cys Leu Pro Gly Tyr Arg Lys Gln Lys Met Gly Pro Ile Tyr
        35                  40                  45

Ala Lys Cys Thr Gly Thr Gly Trp Thr Leu Phe Asn Gln Cys Ile Lys
    50                  55                  60

Arg Arg Cys Pro Ser Pro Arg Asp Ile Asp Asn Gly His Leu Asp Ile
65                  70                  75                  80

Gly Gly Val Asp Phe Gly Ser Ser Ile Thr Tyr Ser Cys Asn Ser Gly
                85                  90                  95

Tyr Tyr Leu Ile Gly Glu Tyr Lys Ser Tyr Cys Lys Leu Gly Ser Thr
            100                 105                 110

Gly Ser Met Val Trp Asn Pro Lys Ala Pro Ile Cys Glu Ser Val Lys
        115                 120                 125

Cys Gln Leu Pro Pro Ser Ile Ser Asn Gly Arg His Asn Gly Tyr Asn
    130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
            165                 170                 175

Ser Asn Pro Pro Thr Cys Gln Ile Val Lys Cys Pro His Pro Thr Ile
        180                 185                 190

Leu Asn Gly Tyr Leu Ser Ser Gly Phe Lys Arg Ser Tyr Ser Tyr Asn
    195                 200                 205

Asp Asn Val Asp Phe Thr Cys Lys Tyr Gly Tyr Lys Leu Ser Gly Ser
210                 215                 220

Ser Ser Thr Cys Ser Pro Gly Asn Thr Trp Gln Pro Glu Leu Pro
225                 230                 235                 240

Lys Cys Val Arg

<210> SEQ ID NO 10
<211> LENGTH: 244
```

```
<212> TYPE: PRT
<213> ORGANISM: Variola Major Virus, Indian Strain

<400> SEQUENCE: 10

Cys Cys Thr Ile Pro Ser Arg Pro Ile Asn Met Thr Phe Lys Asn Ser
  1               5                  10                  15

Val Glu Thr Asp Ala Asn Ala Asn Tyr Asn Ile Gly Asp Thr Ile Glu
             20                  25                  30

Tyr Leu Cys Leu Pro Gly Tyr Arg Lys Gln Lys Met Gly Pro Ile Tyr
         35                  40                  45

Ala Lys Cys Thr Gly Thr Gly Trp Thr Leu Phe Asn Gln Cys Ile Lys
 50                  55                  60

Arg Arg Cys Pro Ser Pro Arg Asp Ile Asp Asn Gly His Leu Asp Ile
 65                  70                  75                  80

Gly Gly Val Asp Phe Gly Ser Ser Ile Thr Tyr Ser Cys Asn Ser Gly
                 85                  90                  95

Tyr Tyr Leu Ile Gly Glu Tyr Lys Ser Tyr Cys Lys Leu Gly Ser Thr
             100                 105                 110

Gly Ser Met Val Trp Asn Pro Lys Ala Pro Ile Cys Glu Ser Val Lys
         115                 120                 125

Cys Gln Leu Pro Pro Ser Ile Ser Asn Gly Arg His Asn Gly Tyr Asn
130                 135                 140

Asp Phe Tyr Thr Asp Gly Ser Val Val Thr Tyr Ser Cys Asn Ser Gly
145                 150                 155                 160

Tyr Ser Leu Ile Gly Asn Ser Gly Val Leu Cys Ser Gly Gly Glu Trp
                165                 170                 175

Ser Asn Pro Pro Thr Cys Gln Ile Val Lys Cys Pro His Pro Thr Ile
            180                 185                 190

Leu Asn Gly Tyr Leu Ser Ser Gly Phe Lys Arg Ser Tyr Ser Tyr Asn
        195                 200                 205

Asp Asn Val Asp Phe Thr Cys Lys Tyr Gly Tyr Lys Leu Ser Gly Ser
    210                 215                 220

Ser Ser Ser Thr Cys Ser Pro Gly Asn Thr Trp Gln Pro Glu Leu Pro
225                 230                 235                 240

Lys Cys Val Arg

<210> SEQ ID NO 11
<211> LENGTH: 244
<212> TYPE: PRT
<213> ORGANISM: Variola Minor Virus, Alastrim Garcia Strain

<400> SEQUENCE: 11

Cys Cys Thr Ile Pro Ser Arg Pro Ile Asn Met Lys Phe Lys Asn Ser
  1               5                  10                  15

Val Glu Thr Asp Ala Asn Ala Asn Tyr Asn Ile Gly Asp Thr Ile Glu
             20                  25                  30

Tyr Leu Cys Leu Pro Gly Tyr Arg Lys Gln Lys Met Gly Pro Ile Tyr
         35                  40                  45

Ala Lys Cys Thr Gly Thr Gly Trp Thr Leu Phe Asn Gln Cys Ile Lys
 50                  55                  60

Arg Arg Cys Pro Ser Pro Arg Asp Ile Asp Asn Gly His Leu Asp Ile
 65                  70                  75                  80

Gly Gly Val Asp Phe Gly Ser Ser Ile Thr Tyr Ser Cys Asn Ser Gly
                 85                  90                  95

Tyr Tyr Leu Ile Gly Glu Tyr Lys Ser Tyr Cys Lys Leu Gly Ser Thr
```

-continued

```
                100                 105                 110
Gly Ser Met Val Trp Asn Pro Lys Ala Pro Ile Cys Glu Ser Val Lys
            115                 120                 125
Cys Gln Leu Pro Pro Ser Ile Ser Asn Gly Arg His Asn Gly Tyr Asn
        130                 135                 140
Asp Phe Tyr Thr Asp Gly Ser Val Val Thr Tyr Ser Cys Asn Ser Gly
145                 150                 155                 160
Tyr Ser Leu Ile Gly Asn Ser Gly Val Leu Cys Ser Gly Gly Glu Trp
                165                 170                 175
Ser Asn Pro Pro Thr Cys Gln Ile Val Lys Cys Pro Tyr Pro Thr Ile
            180                 185                 190
Leu Asn Gly Tyr Leu Ser Ser Gly Phe Lys Arg Ser Tyr Ser Tyr Asn
        195                 200                 205
Asp Asn Val Asp Phe Thr Cys Lys Tyr Gly Tyr Lys Leu Ser Gly Ser
    210                 215                 220
Ser Ser Ser Thr Cys Ser Pro Gly Asn Thr Trp Gln Pro Glu Leu Pro
225                 230                 235                 240
Lys Cys Val Arg

<210> SEQ ID NO 12
<211> LENGTH: 197
<212> TYPE: PRT
<213> ORGANISM: Monkeypox Virus, Isolated from a Human Patient fr6

<400> SEQUENCE: 12

Tyr Cys Thr Ile Pro Ser Arg Pro Ile Asn Met Lys Phe Lys Asn Ser
1               5                   10                  15
Val Glu Thr Asp Ala Asn Tyr Asn Ile Gly Asp Thr Ile Glu Tyr Leu
            20                  25                  30
Cys Leu Pro Gly Tyr Arg Lys Gln Lys Met Gly Pro Ile Tyr Ala Lys
        35                  40                  45
Cys Thr Gly Thr Gly Trp Thr Leu Phe Asn Gln Cys Ile Lys Arg Arg
    50                  55                  60
Cys Pro Ser Pro Arg Asp Ile Asp Asn Gly Gln Leu Asp Ile Gly Gly
65                  70                  75                  80
Val Asp Phe Gly Ser Ser Ile Thr Tyr Ser Cys Asn Ser Gly Tyr His
                85                  90                  95
Leu Ile Gly Glu Ser Lys Ser Tyr Cys Glu Leu Gly Ser Thr Gly Ser
            100                 105                 110
Met Val Trp Asn Pro Glu Ala Pro Ile Cys Glu Ser Val Lys Cys Gln
        115                 120                 125
Ser Pro Pro Ser Ile Ser Asn Gly Arg His Asn Gly Tyr Glu Asp Phe
    130                 135                 140
Tyr Ile Asp Gly Ser Ile Val Thr Tyr Ser Cys Asn Ser Gly Tyr Ser
145                 150                 155                 160
Leu Ile Gly Asn Ser Gly Val Met Cys Ser Gly Gly Glu Trp Ser Asn
                165                 170                 175
Pro Pro Thr Cys Gln Ile Val Lys Cys Pro His Pro Ile Ser Asn Gly
            180                 185                 190
Lys Leu Leu Ala Ala
        195
```

APPLICATION OF A VIRAL COMPLEMENT INHIBITORY PROTEIN IN THE TREATMENT AND DIAGNOSIS OF ALZHEIMER'S DISEASE

This Application is a U.S. National Stage Application of PCT/US00/01115 filed Jan. 19, 2000, which claims benefit of U.S. Provisional Application 60/116,328 filed Jan. 19, 1999.

BACKGROUND OF THE INVENTION

1. Field of the Invention

The present invention provides a novel treatment for senile dementia (Alzheimer's Type), comprising administering an anti-complement protein to a patient in need of such treatment in an amount sufficient to inhibit the complement cascade and thereby inhibit the production of amyloid plaques in the brain of the patient.

2. Description of the Related Art

Alzheimer's Disease (AD) is a slowly debilitating neurodegenerative chronic illness that may progress for a decade or longer before death ensues. The disease often strikes later in life. This is evidenced by the fact that half of those over the age of 80 years are afflicted with the disorder. At present, it is the fourth leading cause of adult deaths in the US alone, at an annual cost of approximately $100 billion. As the longevity of the world's population increases, this disease will become an even greater problem unless a better understanding of the disease process and its management is achieved.

Alois Alzheimer is credited with being the first to diagnose what is now known as Alzheimer's disease (AD). In 1906, Alzheimer reported a case of what he termed "presenile dementia" in a 51 year old patient at a psychiatric meeting in Southwest Germany. He recognized certain characteristics that he felt differentiated it from the usual diagnosis of dementia. First was the early onset of the disease in an otherwise healthy young woman. More importantly, however, were the histological changes he found in sections of brain tissue from the patient. Alzheimer described seeing amyloid (starch-like) plaques and coarse-fibered proliferations of neurofibrils under the microscope. Several other researchers in years following reported similar findings of presenile dementia, and in 1910 a textbook of psychiatric disorders defined this form of dementia as "Alzheimer's disease." The eponym was adopted in the literature and became the standard. It is perhaps fitting, since Alzheimer's original observations are still the main criteria of diagnosis for the disease.

Figure 1A:

The plaques and neurofibrils described by Alzheimer, which are today called senile plaques and neurofibrillary tangles (NFT), are used as a definitive diagnosis of AD (FIG. 1A (Palmert, M. R. et al. (1996) *Science* 24:11080–11084). The plaques and tangles are seen primarily in the hippocampus, amygdale, and the cerebral cortex (Van Broeckhoven, C. L. (1995) *Eur. Neurol.* 35:8–19). Evidence for either a molecular or immunological disease origin may be found in the plaques and tangles, depending upon a researcher's point of reference. From a molecular perspective, the initial identification of specific mutations within the amyloid precursor protein (APP) (Schellenberg, G. D. et al. (1991) 49:511–517) and the presence of Aβ (a derivative of APP) in plaques points to a unique protein cause for AD.

Several other protein players have since entered the AD arena. These include the already mentioned major constituent of NFTs, tau, as well as three recent additions. Presenilins 1 and 2 are integral membrane proteins coded for on different chromosomes, that when mutated are responsible for up to 90% of the cases of autosomal dominant early-onset familial Alzheimer's disease (FAD) (Thinakaran, G. et al. (1996) *Neuron* 17(1):181–190). Although FAD accounts for only 10%, of all cases of AD, there is evidence of an interaction between the presenilins and APP (Weidemann, A. et al. (1997)*Nat. Med.* 3(3):328–332). Therefore, even normal forms of the proteins may play a role in the far more common sporadic AD. Finally, a specific isoform of apolipoprotein E (apoE), apoE4, has been shown to be a strong genetic risk factor for AD (Stritmatter, W. J. et al. (1993) *Proc. Natl. Acad. Sci. USA* 90:8098–8102). People carrying two copies of the of the E4 isoform have a statistically greater risk of developing late-onset AD and in vitro experiments have shown that apoE is capable of binding to Aβ (Stritmatter, W. J. et al. (1994) *Proc. Natl. Acad. Sci. USA* 91:11183–11186).

The histopathological investigations into AD also point to the immune response having an important role in disease progression. The presence of activated microglia, reactive astrocytes, acute phase proteins, and complement factors within and around neuritic plaques are all signs of in inflammatory response. It is known that APP is capable of binding specifically to C1q, which can trigger activation of the classical pathway of the complement cascade in an antibody-independent manner (Webster, S. et al. (1995) *Biochem. Biophys. Res. Comm.* 217:869–875). Deposition of complexes and formation of immunomodulators by the cascade have been credited with activating the microglia—macrophages of the brain—which in turn cause a progression and maintenance of the inflammation. Local tissue destruction follows, along with a further persistence and increase in inflammation.

Histological and Immunohistopathological Features of AD

The plaques are the most distinctive feature found in the brain tissue of patients with AD. These characteristic plaques are composed of an aggregation of the Aβ peptide, which is a by-product of APP metabolism. Morphologically distinct varieties of Aβ deposits have been described from conventional silver staining of histological sections:

Early lesions, referred to as diffuse plaques, are formed from Aβ deposits but are not associated with dystrophic neurites. Diffuse plaques are found in nondemented persons over the age of 65 years and are immunoreactive with a variety of different anti-AP antibodies. However, they generally are not stained with dyes like Congo red and thioflavin S.

In sharp contrast, amyloid plaques (also referred to as neuritic plaques because they contain cells and subcellular components such as astrocytic processes, dystrophic neurites, microglia, neurons with or without neurofibrillary tangles and proteins such as complement components, apolipoprotein E and alpha-1-chymotrypsin) develop at later stages of AD. As seen in the autopsied brain tissue in FIG. 1, they appear dark in the center when stained with silver, and also stain with both Congo red and thioflavin S.

Recently, new lesions known as "AMY" plaques have been reported. This third type of plaque is similar to the amyloid plaques but have no central amyloid core (Schmidt, M. L. et al. (1995) *Am. J. Pathol* 147:503–515).

Besides plaques, the intracellular neurofibrillary tangles are often also characteristic of AD brain tissue. The plaques and neurofibrillary tangles are the primary diagnostic features of AD. However, immunohistochemical staining is becoming more useful as additional antibodies specific to plaque components are developed. An immunodominant region of APP has been localized to the C-terminal tail. This region of the processed APP had been postulated to remain intracellular and was recently shown to accumulate specifically in the neuronal cells of the hippocampus and amygdale of AD patients, but not in similar tissue of the normal age-matched patients (Kotwal, G. J. et al. (1997) *Soc. Neurosci. Abstr.* 22:502). As shown in FIG. 1B, a high titer antibody to the immunodominant region can give rise to specific intracellular immunohistochemical staining in the amygdale, which may someday find routine usage to confirm diagnosis in conjunction with clinical history and silver staining. Additionally, the presence of the C-terminus demonstrates that the C-terminal tail of APP accumulates intracellularly in neural tissue of those suffering from AD.

Molecular Genetics of AD

There are several critical molecules their directly or indirectly contribute to the disease state in AD (Selkoe, D. J. (1997) *Science* 275:630–631). These molecules, their chromosomal locations, and how they may impact AD are summarized in Table 1.

cannot prevent the formation of neurofibrillary tangles and does not allow microtubule assembly, thus contributing to some of the pathogenesis of AD (Roses, A. D. (1997) *Hosp. Pract.* 32(7):51–63).

The most recent group of proteins discovered to have an involvement in AD are the two presenilins (PS1 and PS2). Point mutations in these proteins are sufficient to cause early-onset FAD. The roughly 30 mutations in PSI and 2 in PS2 account for at least 50% of the early-onset FAD cases. These proteins are highly conserved with each other.

Structure, Processing, and Interaction of Critical Molecules

Figure 2:
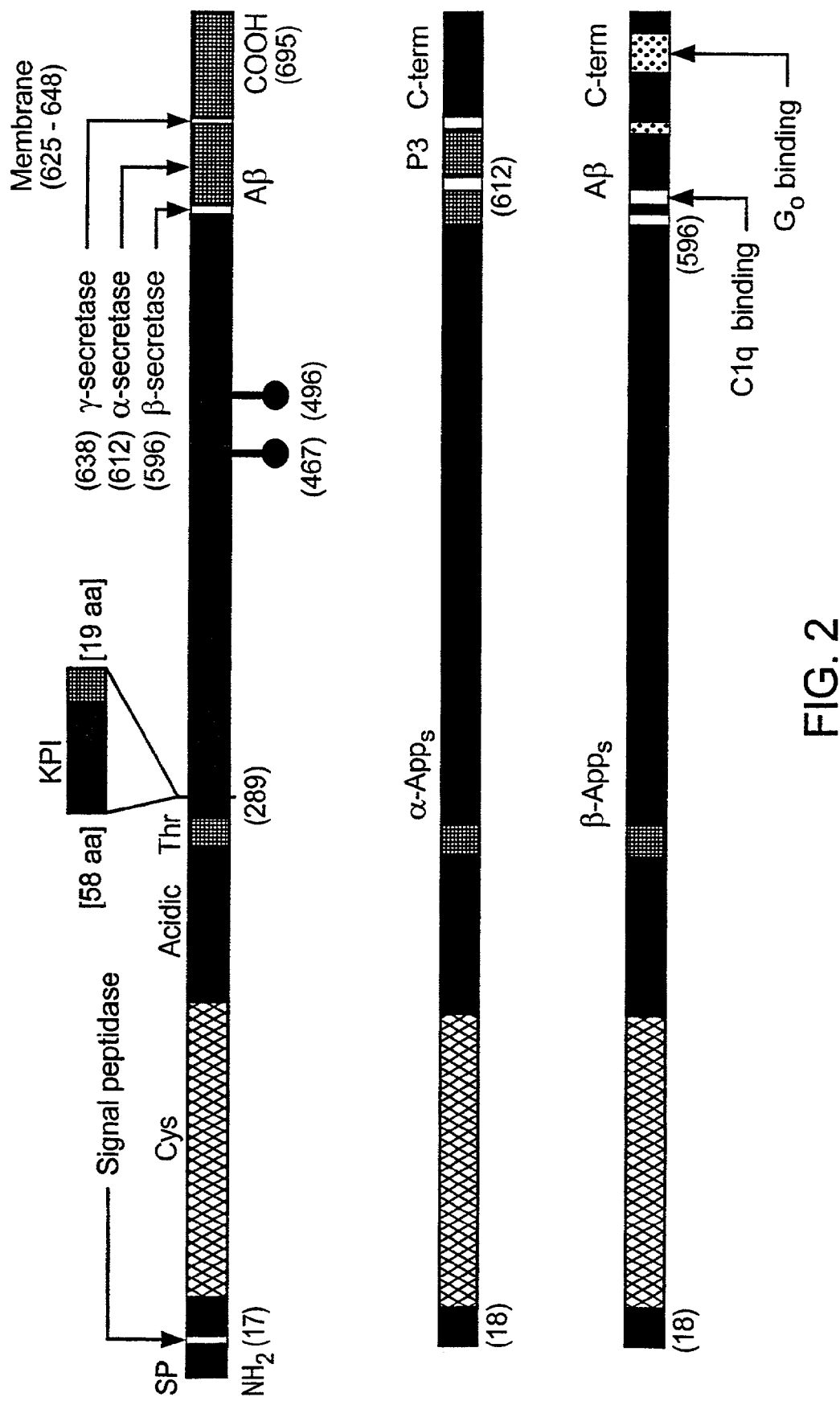

APP is an integral membrane glycoprotein with a large extracellular amino terminus, a single passage through the cell membrane, and a short carboxy-terminal tail, as illustrated in FIG. 2. It is expressed ubiquitously throughout the body and is found in several tissue-specific isoforms due to variant splicing. The largest isoform ($APP_{770}$) contains a putative kunitz protease inhibitor (KPI); however, the form found predominantly in neuronal tissue, $APP_{695}$ does not contain the KPI region. The normal functions of APP have been proposed to include action as a cell receptor, involve-

TABLE 1

Major proteins implicated in Alzheimer's Disease

| Protein | Chromosome | Gene Defect | Age of Onset | Effect on Aβ Production | Sporadic v. Familial |
|---|---|---|---|---|---|
| APP | 21 | Mutations in the C-terminus | 50s | Increased Production | Sporadic/Familial |
| ApoE4 | 19 | Polymorphisms | >60 | Increased density of Aβ plaques | Sporadic |
| Presenilin 1 | 14 | Mutations | 40s and 50s | Increased production | Familial |
| Presenilin 2 | 1 | Mutations | 50s | Increased production | Familial |
| Tau | 17 | None found | Unknown | No known influence on Aβ synthesis | Sporadic? |

The genetic defects in the critical molecules identified to date lead to increased biosynthesis increased aggregation, or decreased clearance of Aβ peptides. Thus, Aβ accumulation is a necessary step in the pathogenesis of AD, but does not account for all the pathogenesis of AD. The gene that is implicated as a risk factor in late-onset sporadic AD and associated with increased risk for AD is the lipid carrier, apolipoprotein E (apoE) epsilon 4 allele (Stritmatter, W. J. & Roses, A. D. (1996) *Ann. Rev. Neurosci.* 19:53). It is suggested that apoE4 is less efficient at cell repair than the alleles E2 and E3. The apoE4 is thought not only to contribute to the formation of β-amyloid plaques, but also to account for the neurofibrillary tangles. It has been suggested that apoE may bind to Aβ and after exiting astrocytes may get trapped into low-density lipoprotein (LDL)-related proteins present on the surface of neurites of apoptotic neurons. ApoE is further suggested to provide protective binding to the tau protein, thus preventing homodimerization. The homodimerization creates paired helical filament formation, which in turn forms the neurofibrillary tangles. In addition, it has been proposed that the alleles of apoE (except E4) contribute to the formation of stabilized cross-bridges on microtubules, and that in the absence of the tau protein microtubules cannot assemble and so the shape and synaptic integrity of cells are not maintained. Since apoE4 has a high affinity for Aβ and the lowest among the isoforms for tau it ment in cell-cell interactions, and inhibition of proteases (KPI), among others (Selkoe, D. J. (1997) *Science* 275: 630–631).

Figure 3:
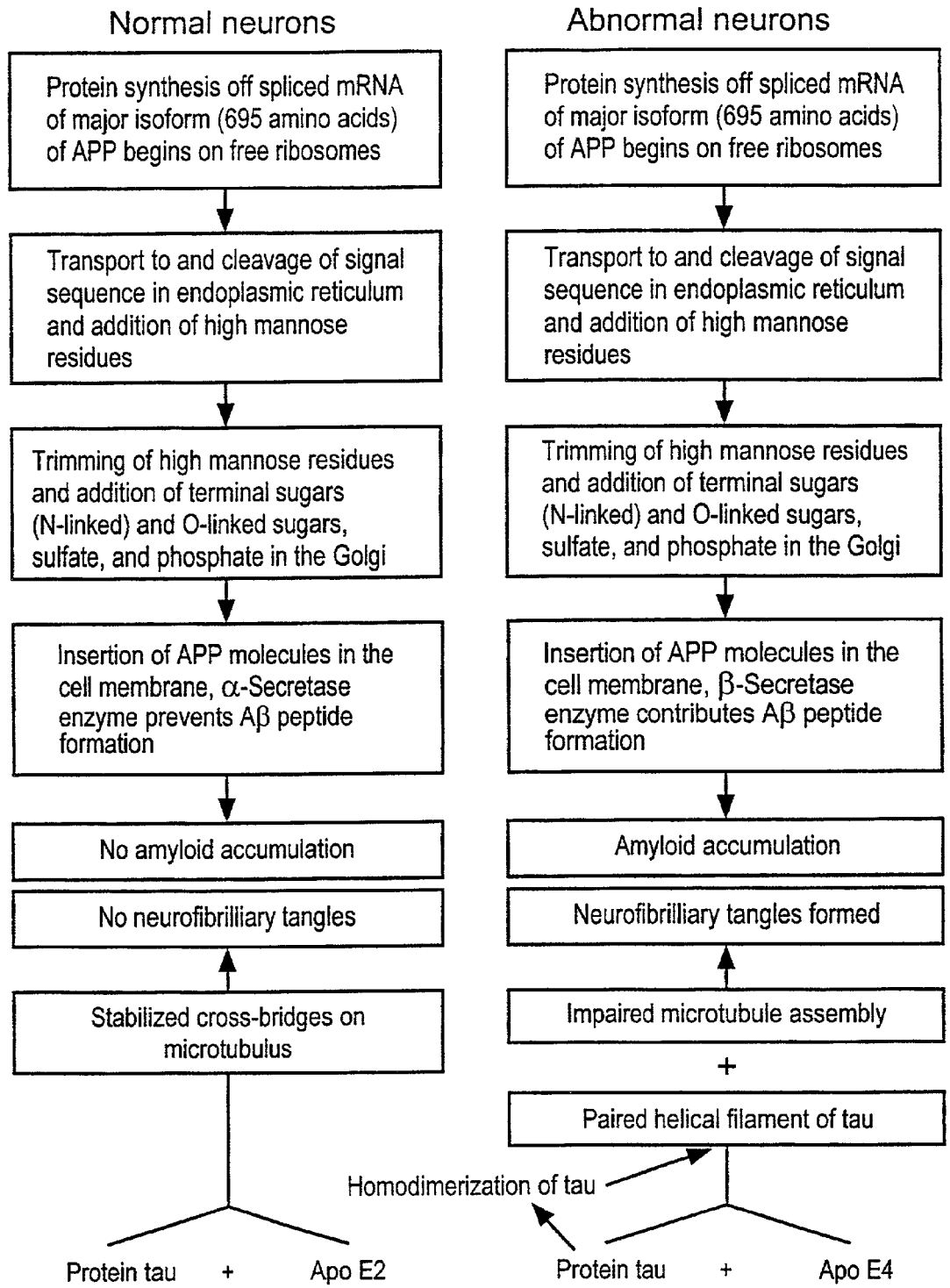

APP contains a signal peptide on its N-terminus and is membrane-anchored, so it is processed through the secretory pathway after translation (see FIG. 3). This pathway begins with cotranslational translocation across the membrane of the endoplasmic membrane (ER) into its lumen, with anchorage in the membrane occurring at the transmembrane domain. Processing of the protein to maturity, including glycosylation and sulfation, continues through the ER and into the Golgi network (Adams, C. (1997) *Gerontology* 43:8–19).

Proteolytic cleavage of APP can also occur as part of its processing through the secretary pathway. Somewhere between the trans-Golgi network and its localization on the cell surface, APP is cleaved at a region on the extracellular side of APP near the membrane in the region that could otherwise form Aβ (Sisodia, S. S. et al. (1990) *Science* 248:492–495), thus prohibiting its formation. The membrane-bound endoprotease responsible for the cleavage has been dubbed α-secretase and appears to require for its specificity no more than an α-helical conformation and a specified distance of 12–13 residues from the membrane (Sisodia, S. S. (1992) *Proc. Nat. Acad. Sci. USA* 89:6075–6079). If cleavage occurs, the soluble amino terminus is released into the solvent, while the carboxyl end remains membrane bound, presumably being degraded. If α-secretase does not hydrolyze APP, then the intact protein may be rapidly reinternalized via a clathrin-mediated endosomal pathway, where it may be either recycled to the surface through an early endosome or fused with a lysosome for degradation (Selkoe, D. J. (1996) *J. Biol. Chem.* 271: 18295–18298).

Aβ is likely to be formed during this process, probably in the early endosome, due to proteolytic cleavage by enzyme(s) called β-secretase and γ-secretase (see FIG. 2). Recycling to the surface would result in release of Aβ into the extracellular medium. It has been demonstrated that Aβ production requires APP to be membrane bound and localized to a slightly acidic vesicle, such as the early endosome or the late trans-Golgi (Selkoe, D. J. (1996) *Ann. N.Y. Acad. Sci.* 777:57–64). The entire processing pathway is tightly controlled. For instance, upregulation of the protein kinase C (PKC) pathway by muscarinic receptors results in an increase in the α-secretase cleavage and a decrease in Aβ production. Serum levels of ligands for these receptors, such as acetylcholine and interleukin-1 (IL-1), have been reported to be abnormal in AD patients (Buxbaum, J. D. & Greengard, P. (1996) *Ann. N.Y. Acad. Sci.* 777:327–331). An intracellular increase in calcium will also upregulate α-secretase activity (Adams, C. (1997) *Gerontology* 43:8–19).

It is known that mutating APP, such as occurs in some cases of early-onset FAD, is sufficient to cause AD. The presence of Aβ in diffuse plaques (precluding symptom onset), its ability to form insoluble filaments in vitro, trisomy 21 in Down's syndrome (patients develop early-onset AD), the exhibited direct neurotoxicity, and the interaction with numerous molecules believed to be involved with AD including immune molecules, all point to APP's, and specifically Aβ's, pivotal role in AD pathogenesis (Spillantini, M. G. et al. (1996) *Acta Neuropath.* (*Berl.*) 92:4248).

One likely mechanism proposed (Stritmatter, W. J. & Roses, A. D. (1996) *Ann. Rev. Neurosci.* 19:53) is that either an increase in Aβ production or a decrease in clearance caused by a variety of different genetic, molecular, or environmental conditions results in Aβ accumulation into fibrils and then diffuse plaques. These plaques activate an inflammatory response (see below and FIG. 4), which can cause local cellular damage, in turn creating more inflammation. Alternatively, or together, the Aβ in the plaques may be directly toxic to neurons, resulting in a similar outcome. The cell damage could result in metabolic changes, which might explain the production of the NFTs seen associated with AD. Persistence of inflammation would result in an ever-spreading synaptic loss and eventual cell death, up to and beyond clinical symptoms of impairment.

A final proposed role of APP in AD involves its C-terminal region. It has been demonstrated that a specific region of the APP terminus (amino acids 657–676) is able to specifically bind and activate heterotrimeric G proteins (see FIG. 2) (Selkoe, D. J. (1996) *J. Biol. Chem.* 271:18295–18298). More specifically, a generated peptide corresponding to $APP_{657-676}$ will bind only with the $G\alpha_o$ subset of G proteins, and it binds with even greater affinity if the transmembrane region is included (Dragunow, M. & Preston, K. (1995) *Brain Res. Rev.* 2:11–28). This suggests that APP acts as a $G_o$-coupled signal receptor. This theory is supported by experiments using a monoclonal antibody generated to the extracellular domain of APP. Application of this antibody to $APP_{695}$ increased binding of the C-terminus $G_o$, but not to other cellular heterotrimeric G proteins (Lassmann, H. et al. (1995) *Acta Neuropath.* (*Berl.*) 92:42–48). Activation of G proteins can result in a signal cascade which ends with apoptotic cell death. It may be that the APP C-terminus could be pathogenic in apoptotic manner, if it accumulates past a critical threshold within cells.

The other important component of AD histopathology is the neurofibrillary tangles (NFTs). There is good evidence that NFTs play an important role in the initiation of AD pathology. This evidence focuses on the microtubule associated protein, tau. When functioning properly, tau binds microtubules and promotes their stable polymerization into fibrils within the cell (Roses, A. D. (1997) *Hosp. Pract.* 32(7):51–63). When tau becomes hyperphosphorylated, it is no longer able to bind microtubules, which causes them to become destabilized, thus resulting in disruption of cellular trafficking and compromises in cytoskeletal integrity. Tau hyperphosphorylation results from an impaired ability to remove phosphates. The microtubule destabilization has been proposed to disrupt axonal transport which causes dying back of axons, impairing synaptic transmission (Peskind, E. R. (1996) *J. Clin. Psychiatry* 57 (Suppl. 14): 5–8). Such a mechanism of AD pathogenesis would not require an interaction with Aβ and therefore would not necessitate plaque formation. Indeed, comparison of a recently discovered presenile dementia lacking plaques but containing tangles shows tau forms and NFTs to be identical to those in AD according to several different analytical methods (Spillantini, M. G. et al. (1996) *Acta Neuropath.* (*Berl.*) 92:42–48).

Hyperphosphorylated tau binds itself, forming long filaments (PHFs), which accumulate intracellularly to form the recognized NFTs. It his been shown that carbamoylation or glycation of cationic tau residues will result in NFTs like those seen in AD. These cationic sites, particularly lysine residues, appear to be important for microtubule binding. Therefore, the phosphorylation of tau probably blocks the normal binding sites of tau to microtubules, preventing interaction (Farias, G. et al., (1997) *Mol. Cell. Biochem.* 168:59–66). NFTs may themselves be pathogenic if they accumulate to such an extent within the cell that they impair normal cellular processes. Also, it has been postulated that isoforms of apoE may interact with tau as well and inhibit or enhance NFT formation (discussed above).

As discussed in detail earlier, ApoE plays a role in at least sporadic AD, and perhaps FAD as well. In particular, the ApoE4 isoform increases the likelihood and decreases the age of onset of AD (Corder, E. H. et al. (1993) *Science* 261:921–923). ApoE is a 34-kDa protein found circulating throughout the body as well as the central nervous system. In the brain, ApoE scavenges lipid from degenerating neurons and redistributes it to branching neurites via uptake by the low-density lipoprotein (LDL) or LDL-related protein (LRP) receptors (Mahley, R. W. et al. (1996) *Ann. N.Y. Acad. Sci.* 777:139–145). ApoE also binds Aβ, and so along with its receptor may be a means of mopping up extracellular Aβ (Rebeck, G. W. (1995) *Ann. Neurol.* 37:211–217).

Presenilins 1 and 2 (PS1, PS2) are also involved in AD. PS1 has been shown to be membrane-anchored and contain eight membrane-spanning regions. The amino and carboxyl termini are both located on the cytoplasmic side of the membrane, along with a large hydrophilic loop between transmembrane domains six and seven. This loop is proteolytically cleaved during maturation of the protein to produce an approximately 25–28 kDa N-terminal and an approximately 16–19 kDa C-terminal protein. The shape is hypothesized to be a barrel within the membrane, with the loop acting as a gate (Rohan de Silva, H. A., & Patel, A. J.

(1997) *Neuroreport* 8(8):i–xii). The mature form has been shown to localize primarily to the perinuclear membrane regions (ER and Golgi), with a small percentage in the surface membrane (Tanzi, R. E. et al. (1996) *Alzheimer's Dis. Rev.* 1:190–198).

The presenilins show close homology to two proteins of *Caenorhabditis elegans*, SPE4 and SEL12. SPE4 mediates the docking of a Golgi-derived organelle which stores and transports polypeptides (Takeshima, A. et al. (1996) *Biochem. Biophys. Res. Comm.* 227:423–426). This suggests a role in protein trafficking through the secretary pathway for the presenilins. SEL12 facilitates signaling by the Notch family of receptors (Beyreuther, K. & Masters, C. L. (1997) *Nature Med.* 3:723–725). These receptors are involved in determination of cell fate during development. This may indicate a role in cell signaling for the presenilins, or perhaps SEL 12 controls transport of second messengers between the nuclear and surface membrane. The latter possibility would again suggest a role for the presenilins in protein trafficking.

A role in cell signaling or protein trafficking relates to AD pathogenesis in the following manner. It is known that mutations in either of the presenilins result in an increase in the expression of Aβ42 without an increase in APP expression (Citron, M. et al. (1997) *Nature Med.* 3:67–72). Also, immunoprecipitation of coexpressed PS2 and APP in cell culture results in complexes of PS2/immature APP (Weidemann, A. et al. (1997)*Nat. Med.* 3(3):328–332). Together, these two pieces of evidence, along with homology and localization studies, suggest that presenilins regulate trafficking and processing of APP through the secretary pathway. When mutations occur in presenilins, it is likely that conformational changes induce a change of function or a new function with regard to APP processing, which results in an increase in the amount of Aβ produced.

Complement-Mediated Inflammatory Response in AD

The neuritic/amyloid plaques which are the hallmark of AD consist of aggregated Aβ, along with a number of complement components and complement control proteins such as C1 inhibitor and other noncomplement proteins. In addition, the neuritic plaques are associated with damaged (dystrophic) neuronal processes, activated microglia, and reactive astrocytes.

An area of intense research has been the antibody-independent activation of complement by nonfibrillar Aβ, the form found in diffuse plaques in the brain. An even more potent activator of complement is the β-pleated sheet aggregated Aβ that forms the fibrils found in neuritic plaques (Webster, S. et al. (1996) *Mol. Immunol.* 33:29). Both the classical complement pathway (CCP) and the alternate complement pathway (ACP) are activated by Aβ, leading to the formation of ester linked Aβ/C3 complexes, generation of a potent proinflammatory response due to products C5a and C5b-9, and formation of membrane attack complexes (MACS) (id.). This local inflammatory response results in the development of an intensely neurotoxic environment due to the influx and activation of glial cells, and damage to neurons near the neuritic plaques.

Specific interaction domains of the Aβ peptide involved in binding to C1q have been reported by Tenner's group. Amino acid residues 4–11 of Aβ have been identified as critical in the binding to C1q, the subunit of C1 that is involved in the activation of the classical complement pathway. Residue number 7, an aspartic acid in Aβ, is believed to be a very critical site for this protein to interact with C1q (Velazquez, P. et al. (1997) *Nature Med.* 3:77–79). Because of the activation of complement and the triggering of signal transduction processes in the classic injury cascade in response to the Aβ; it has been suggested that an amplified Aβ cascade is set off which converts an acute-phase injury response into a chronic one (Cotman, C. W. et al. (1996) *Neurobiol. Aging* 17:723–731). This chronic response is supposedly maintained by continuous stimulation and injury and may be an underlying cause for neuronal dysfunction and progressive degeneration.

Due to the clear involvement of complement in the inflammatory response in AD, targeting the complement system would be expected to slow or stop the progression of AD without affecting the beneficial effects of the normal protective functions of the body's first line of defense. In addition, active regions of several of the microbial immunomodulatory proteins, which target the complement cascade at various sites, can be employed for therapeutic intervention in inflammatory responses due to activation of the complement cascade (Kotwal, G. J. (1996) *Immunologist* 4:157–164). For example, the inflammation modulatory protein (IMP), a small complement-binding protein that has been shown to be functionally similar to CR1, has been shown in in vivo experiments to cause a diminished specific swelling response (Miller, C. G. et al. (1997) *Virology* 22:126–133).

Neuroautoimmunity

Besides complement-mediated inflammation, inflammation resulting from autoimmunity has also been proposed to play a role in the pathogenesis of AD. According to the neuroautoimmunity model, cell-mediated immunity (CMI) plays a key role in the development of autoimmunity and/or inflammation (Singh, V. K. (1997) *Gerontology* 43:79–94). The first step in the proposed process is the formation of an autoantigen during the blood-borne acute phase, resulting in the activation of B and T cells, which give rise to anti-neuronal antibody and cytotoxic T-cell (CTL) activity, respectively. This somehow signals across the blood-brain barrier and leads to a chronic phase in the brain. In the second phase the $CD8^+$ CTLs, either directly through CMI or indirectly through glia activation (microglial and astroglial cells), induce target cell cytotoxicity. The activation of the glial cells then causes nonspecific tissue damage. The neuron-specific degeneration characteristic of AD is due to the CMI directed by specific autoantibodies. A large number of autoantibodies and immune abnormalities, some of which are inherited, have been cataloged by Singh (id.)

Prior Modes of Treatment of Alzheimer's Disease

A major approach to the treatment of AD has involved attempts to augment the cholinergic function of the brain. An early approach was the use of precursors of acetylcholine synthesis, such as choline chloride and phosphatidyl choline (lecithin). Although these supplements are generally well tolerated, randomized trials have failed to demonstrate any clinically significant efficacy. Direct intracerebroventricular injection of cholinergic agonists such as bethanacol appears to have some beneficial effects, although this requires surgical implantation of a reservoir connecting to the subarachnoid space and is too cumbersome and intrusive for practical use. A somewhat more successful strategy has been the use of inhibitors of acetylcholinesterase (AChE), the catabolic enzyme for acetylcholine. Physostigmine, a rapidly acting, reversible AChE inhibitor, produces improved responses in animal models of learning, and in patients with AD some studies have demonstrated mild transitory improvement in memory following physostigmine treatment. The use of physostigmine has been limited because of its short half-life and tendency to produce symptoms of systemic cholinergic excess at therapeutic doses.

Recently, the acridine derivative tacrine (COGNEX®, 1,2,3,4-tetrahydro-9-aminoacridine) has been approved by the United States Food and Drug Administration for the treatment of dementia in AD. Tacrine was first synthesized nearly fifty years ago, and the pharmacology of this agent has been the subject of numerous studies. It is a potent centrally acting inhibitor of AChE. The side effects of tacrine may be significant and dose-limiting: abdominal cramping, nausea, vomiting, and diarrhea are observed in up to one-third of patients receiving therapeutic doses. Tacrine may also cause hepatotoxicity, as evidenced by the elevation of serum transaminases observed in up to 20% of patients treated. Because of the relatively small improvements that result from tacrine treatment and the significant side-effect profile, its clinical usefulness is limited.

Therefore, in view of the aforementioned deficiencies attendant with prior art methods of treating Alzheimer's Disease, it should be apparent that there still exists a need in the art for an safe and effective treatment for AD.

SUMMARY OF THE INVENTION

Briefly, the present invention features a Vaccinia virus encoding a complement control protein which can block the complement pathway, binding to complement components. This property can be used in the treatment and diagnosis of Alzheimer's disease. The viral protein, termed VCP, can block the complement activation in AD and can bind to plaques in pathological samples.

More particularly, the present invention relates to a method for treating Alzheimer's disease comprising administering to a patient in need of such treatment a therapeutic amount of the protein of Formula (I):

```
M K V E S V T F L T L L G I G C V L S C C T I P S
R P I N M K F K N S V E T D A N A N Y N I G D T I
E Y L C L P G Y R K Q K M G P I Y A K C T G T G W
T L F N Q C I K R R C P S P R D I D N G Q L D I G
G V D F G S S I T Y S C N S G Y H L I G E S K S Y
C E L G S T G S M V W N P E A P I C E S V K C Q S
P P S I S N G R H N G Y E D F Y T D G S V V T Y S
C N S G Y S L I G N S G V L C S G G E W S D P P T
C Q I V K C P H P T I S N G Y L S S G F K R S Y S
Y N D N V D F K C K Y G Y K L S G S S S S T C S P
G N T W K P E L P K C V R
(SEQ ID NO:1)
```

The invention further provides a pharmaceutical formulation for the treatment of Alzheimer's Disease, which comprises a protein of the Formula (I) together with one or more pharmaceutical acceptable diluents, carriers or excipients therefore.

With the foregoing and other objects, advantages and features of the invention that will become hereinafter apparent, the nature of the invention may be more clearly understood by reference to the following detailed description of the preferred embodiments of the invention and to the appended claims.

BRIEF DESCRIPTION OF THE DRAWINGS

FIG. 1. AD Brain Tissue. FIG. 1A shows a conventional silver stained section of brain tissue from postmortem AD patient showing the characteristic hallmark of AD, the amyloid/neuritic plaques (indicated by arrows). The central portion of a plaque is a dense, dark brown to black region surrounded by a clear ring and then a ring of particulate matter comprising cell debris, activated microglial cells, and several different proteins. FIG. 1B shows immunohistochemical staining of a microsection of the amygdala (a brain structure that plays a major role in emotions such as fear and anxiety and in the startle response) from a postmortem AD patient. A high-titer antibody raised in a rabbit against a synthetic peptide whose sequence was derived from a computer-generated immunodominant region within the putative intracellularly localized C-terminal tail of APP was used as a primary antibody. This was followed by a peroxidase-conjugated anti-rabbit secondary antibody. Brown color developed on addition of DAB reagent. The nuclei were finally stained with hematoxylin. The numerous brown threads seen specifically in the AD tissue are indicative of the presence of the cytoplasmic C-terminal tail of APP in the neuropils (dead/dying neurons).

FIG. 2. A detailed diagram of the major isoform of amyloid precursor protein ($APP_{695}$) present in neurons. The 17-amino acid signal peptide is cotranslationally cleaved in the endoplasmic reticulum. The APP has a cysteine-rich region (8 cysteines within a span of 150 amino acids), as well as an acidic region with a high percentage of the acidic amino acids, glutamic acid and aspartic acid. A threonine-rich region is marked Thr. Alternatively spliced mRNA (in tissues elsewhere in the body) may have an insertion of up to 225 nucleotides that encodes a 56-amino acid Kunitz protease inhibitor region (KPI) to form the isoform $APP_{751}$, and another additional 19-amino acid region (isoform $APP_{770}$). The APP anchors to the cell surface via a membrane-spanning region. Depending on the type of proteolytic cleavage, the cell surface APP can either be digested by α-secretase and gamma-secretase to give rise to α-APPs (584 amino acids) and a small P3 protein, which are soluble and are released into the extracellular space, with the C-terminus staying behind (as shown in the middle diagram). Alternatively, it may be digested by β-secretase and gamma-secretase to give rise to Aβ containing a region (40–42 amino acids) that is secreted along with β-APPs (578 amino acids), with the C-terminal tail remaining cell associated. The Aβ aggregates to form the nucleus of the amyloid plaque and has a region that can bind C1q and activate the classical complement pathway. The Aβ can also couple to C3 via an ester linkage and activate the alternative pathway. The cytoplasmic C-terminal tail has been speculated to trigger a cascade of events contributing to the apoptosis of the APP-producing neurons. Such a cascade is thought to be initiated by the binding of the C-terminal region to a particular family of GTP binding proteins ($G_0$).

FIG. 3. The aberrant biosynthesis of APP accounts for some of the amyloid plaque formation. This is complicated by other proteins regulating the amount of APP synthesized and process, such as the presenillins 1 and 2. The neurofibrillary tangles (NFTs) may be formed when the tau protein homodimerizes in the presence of the epsilon 4 allele of apoE, statistically found more often in persons susceptible to neurodegenerative disorders. The second and third alleles may be able to block the sites on tau that contribute to the formation of homodimers, thereby contributing to the normal cytoskeletal structure. ApoE, besides having sites for binding to its receptor, has a lipid binding site to which Aβ can bind. Aβ can thus be transported from astrocytes to the neuronal surface and recycled via endosomes and lysosomes to remain cytoplasmic and become incorporated in the neurofilbrillary tangles.

Figure 4:
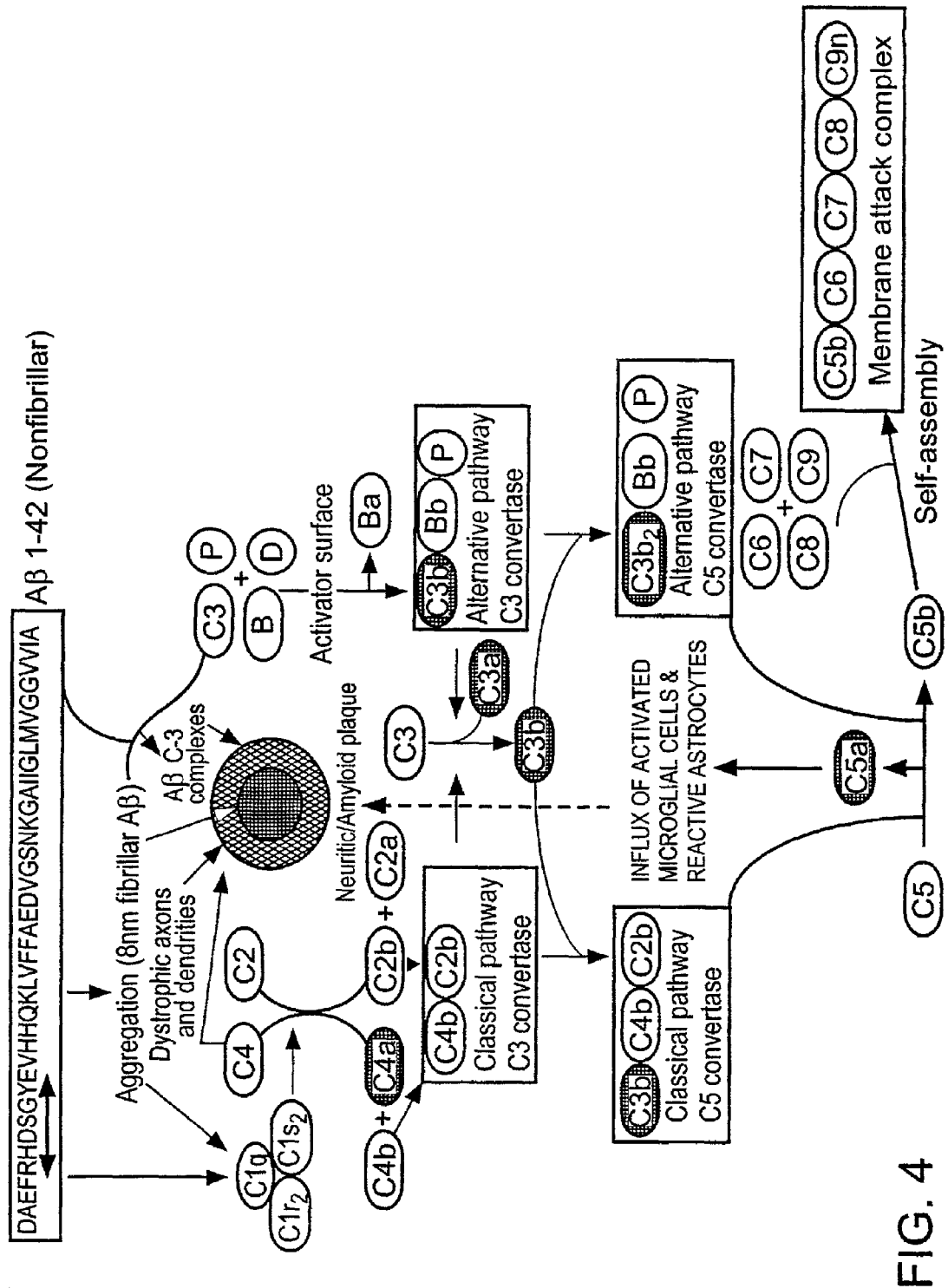

FIG. 4. Antibody-independent activation of the classical complement pathway (CCP) and initiation of inflammatory events in AD. Aβ, its aggregate, or the amyloid plaque can trigger the CCP by binding to C1q. The binding to C1q occurs via the first few amino acids of Aβ (4–11), with the aspartate in position 7 being the most critical for binding. Aβ or its aggregate can form ester links to the C3 component and can activate the alternate complement pathway (ACP). Complement activation can result in the release of chemotactic factors such as C3a, C4a, and C5a. These factors can cause an influx of microglial cells and astrocytes, which contribute to the inflammatory response. These cells are also present in the neuritic plaques.

Figure 5:
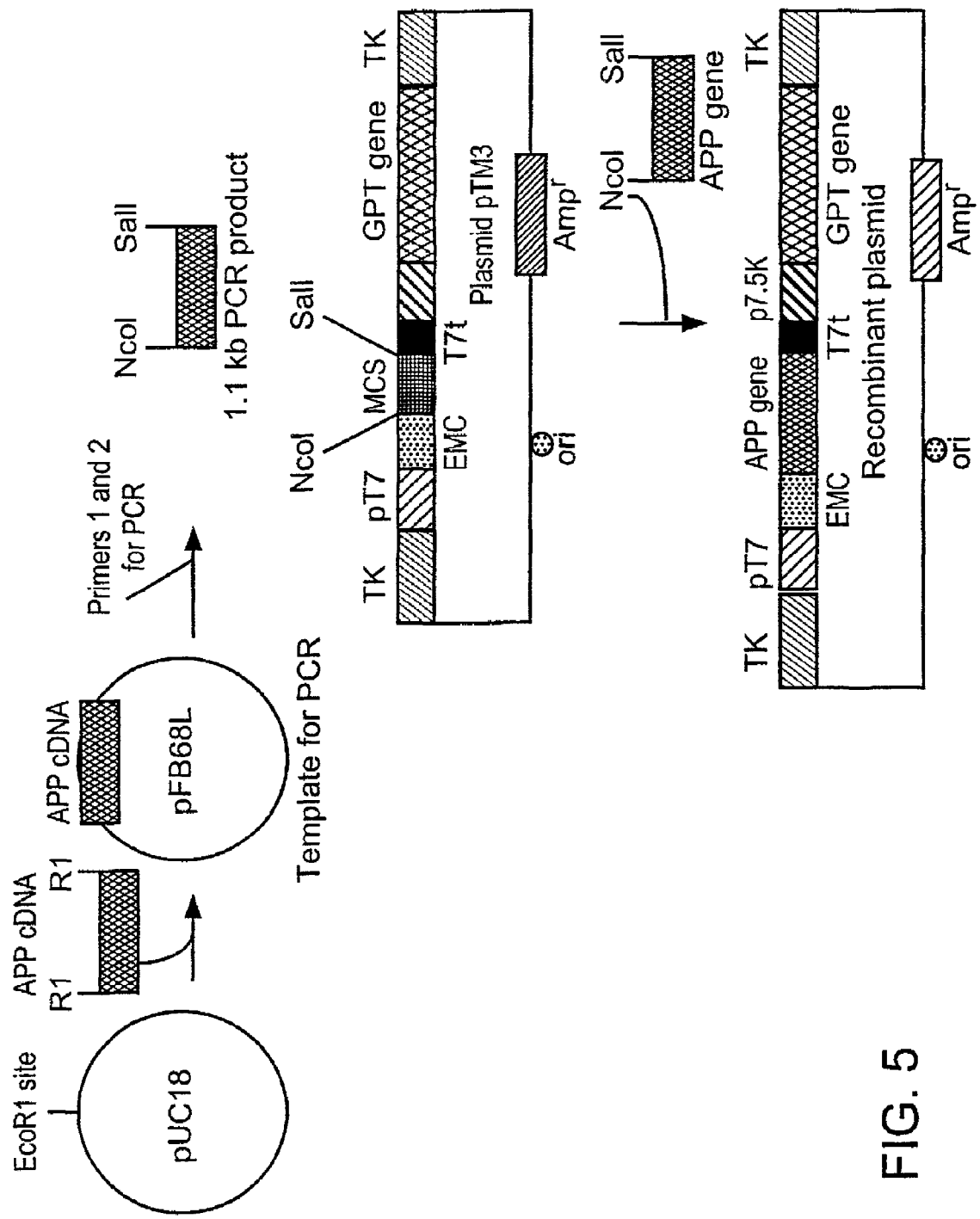

FIG. 5. Generation of recombinant plasmid pAPPc. PCR was performed on a modified pUC 18 vector, pFB68L, containing the $APP_{695}$ C-terminus (nucleotides 1786–3207) incorporated at the EcoRI restriction site. The primers were designed so that the 1.1 kbp PCR product would contain the two new restriction sites NcoI and SalI. Digestion of the PCR product and pTM3 with NcoI and SalI and subsequent ligation produced plasmid pAPPc. Abbreviations: multiple cloning site (MCS), T7 bacteriophage promoter (pT7), termination sequence (T7t), encephalomyocarditis virus "translational enhancer" leader sequence (EMC), guanosyl phophoribosyl transferase (GPT), 7.5 kbp vaccinia promoter (p7.5K), thymidine kinase (TK), origin of replication (ori), ampicillin resistance gene (ampr).

FIG. 6 shows the purification of pAPPc. FIG. 6A shows a purified and restricted clone of pAPPc electrophoresed through an agarose gel. FIG. 6B shows twelve purified and restricted clones of pAPPc electrophoresed through an agarose gel. FIG. 6C shows a Southern blot of the twelve pAPPc clones from the agarose gel shown in FIG. 6B.

FIG. 7. Sequence of pAPPc within insert and flanking regions. The DNA (SEQ ID NO:3) and amino acid (SEQ ID NO:4) sequences of pAPPc and the flanking pTM3 sequence is shown with primer sets, restriction sites and important regions noted. The arrows indicate the location and direction of the five sets of primers synthesized for DNA sequencing.

Figure 8:
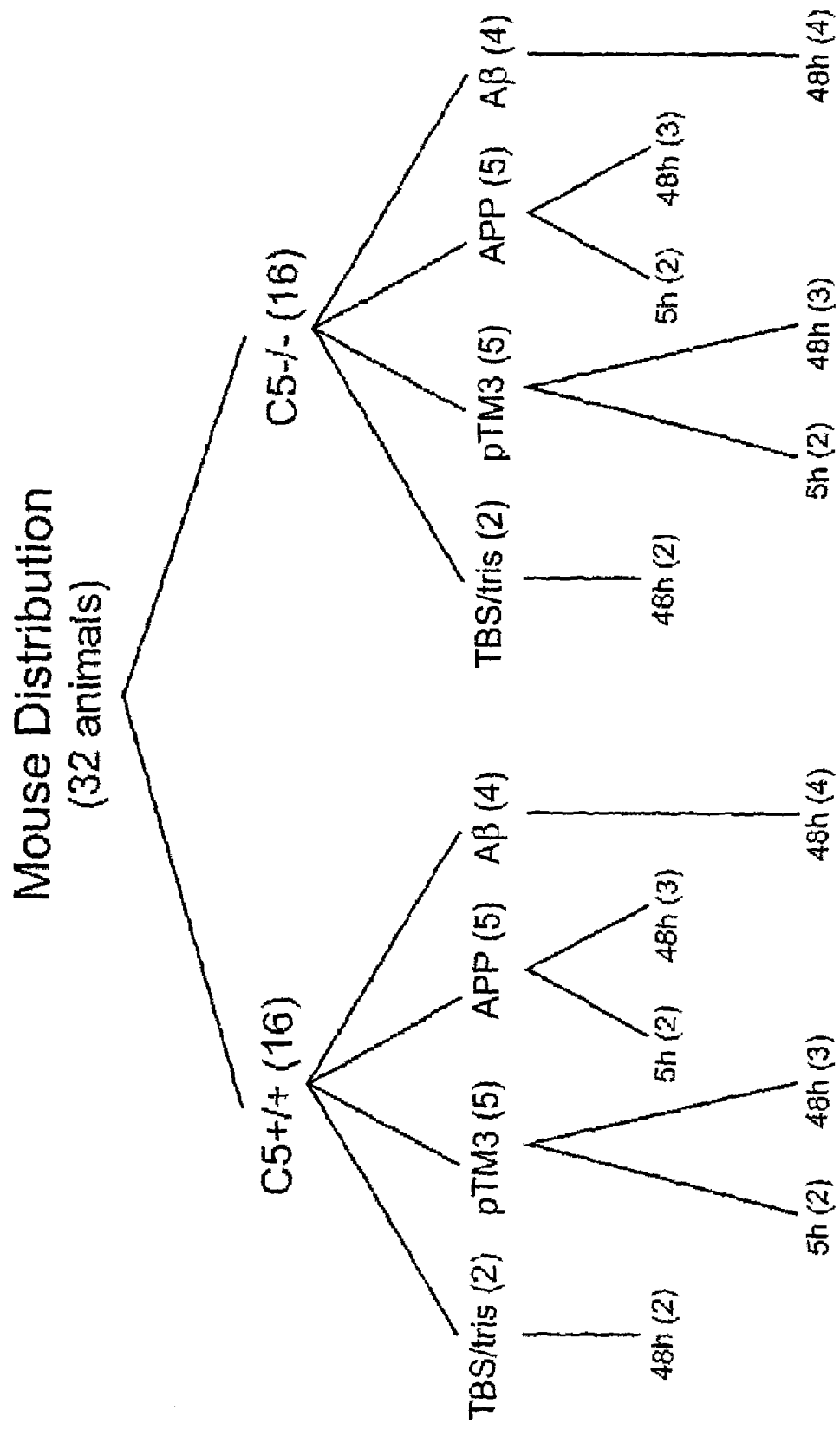

FIG. 8. Flow chart of distribution of mice into groups. Thirty-two animals were injected in a series of three experiments with either Tris-buffered saline or Tris buffer, control product (pTM3) or C-100 (APP), or AB peptide. The mice were sacrificed at either five (5h) or 48 (48h) hours after injection. C5+/+ and C5−/− mice were used. Numbers in parenthesis indicate the number of individual mice in each group.

Figure 9A:
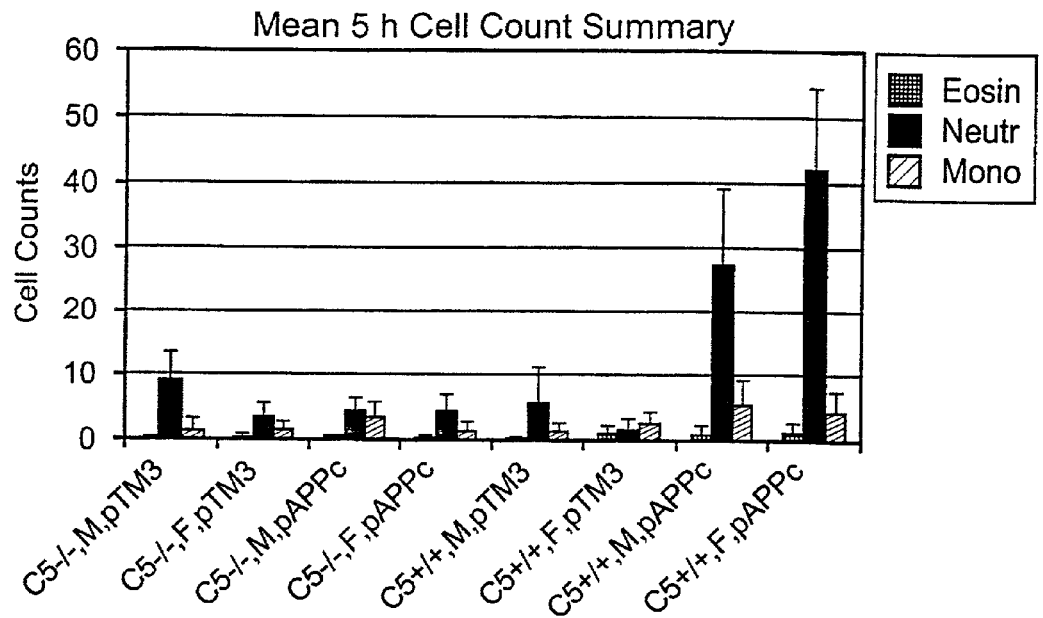
Figure 9B:
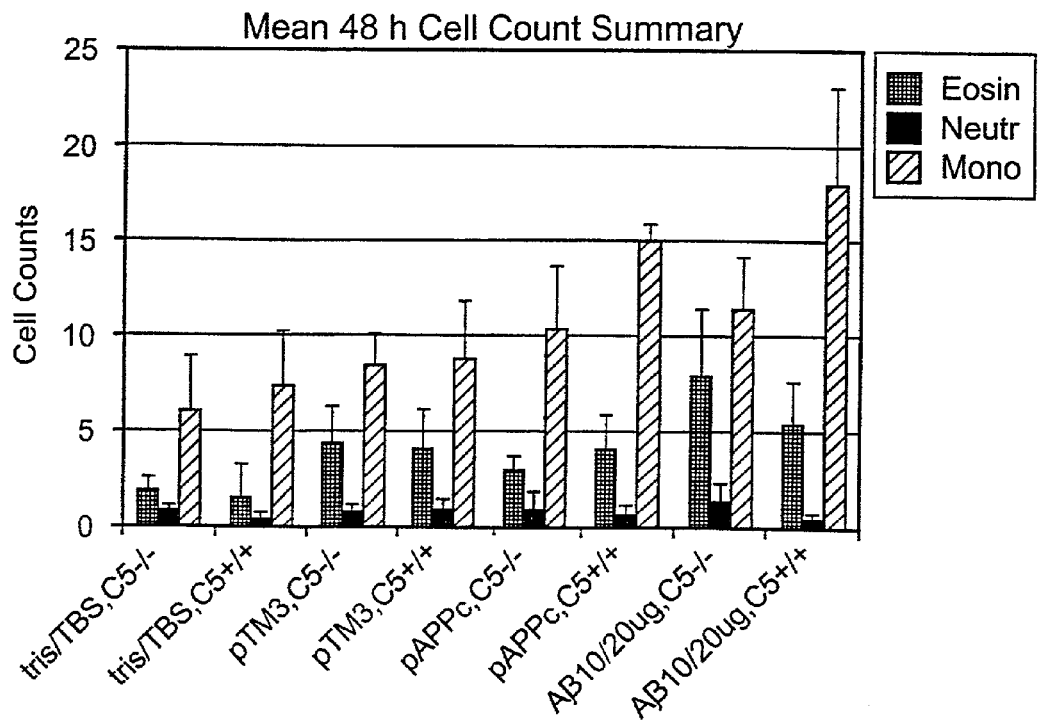
Figure 10A:
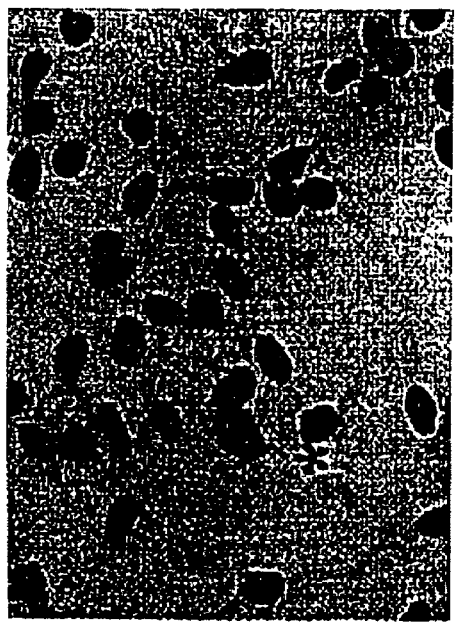
Figure 10B:
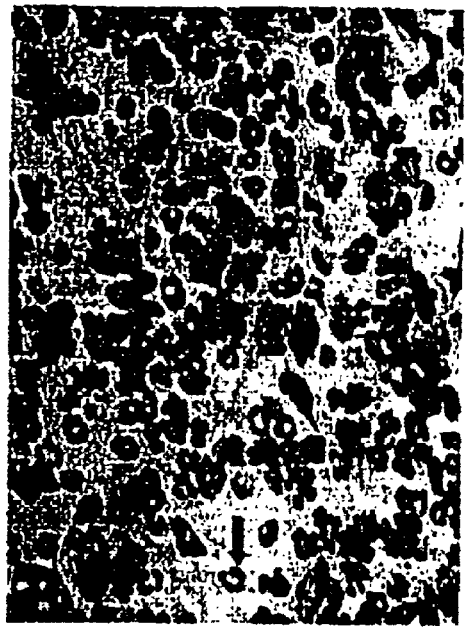
Figure 10C:
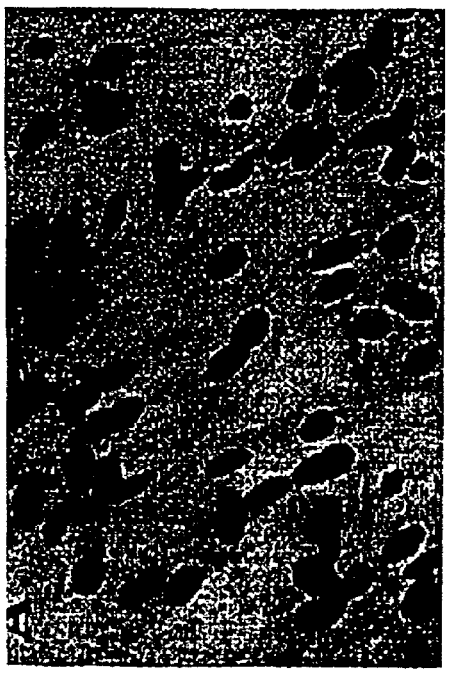
Figure 10D:
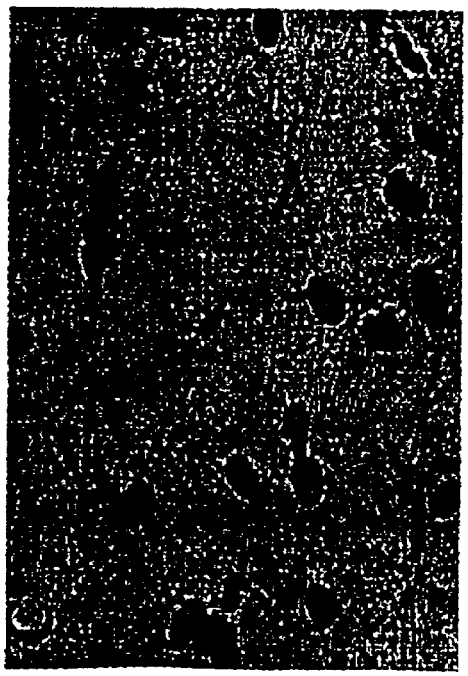
Figure 10E:
Figure 10F:
Figure 10G:
Figure 10H:

FIG. 9. Connective tissue Air pouch cell counts. Cell count bars are means of all gfids counted from animals injected with 100 microliters of sample listed on x-axis, plus or minus standard deviation shown as an error bar. FIG. 9A is a summary of counts from mice sacrificed five h post injection. FIG. 9B is a summary of counts from mice sacrificed 48 h post injection. Abbreviations: C5 sufficient (C5+/+) or deficient (C5−/−) mice, male (M), female (F), control product (pTM3) or C-100 (pAPPc), AB peptide (AB), eosinophil (Eosin), neutrophil (Neutr), monocyte (Mono).

FIG. 10. Air pouch connective tissue section composite Representative photos of single-layer connective tissue spreads from one experiment. Left column panels (FIGS. 10A, C, E and G) are from C5−/− mice injected, whereas right column panels (FIGS. 10B, D, F and H) are from C5+/+ mice injected. Panels 10A, B, C and D are from mice sacrificed five hours after injection. Panels 10E, F, G and H are from mice sacrificed 48 h after infection. Mouse sections in panels 10A, B, E and F were from animals injected with in vitro transcription/translation product encoded by control pTM3 DNA, and those in panels 10 C, D, G and H were injected with product from in vitro transcription/translation reaction encoded by pAPPc DNA. Migrating cells found most frequently in epithelial air pouch sections are indicated: resident fibroblast, (←) neutrophil, (■) eosinophil, (♦) monocytes. The magnification used is 400×.

Figure 11A:
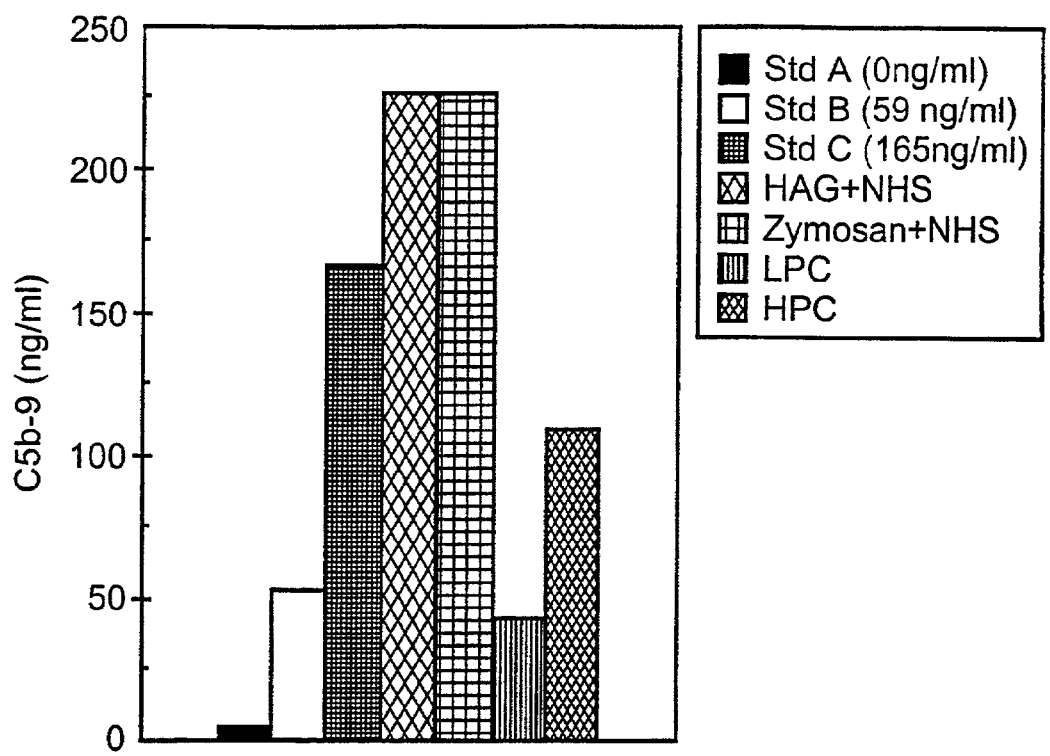
Figure 11B:
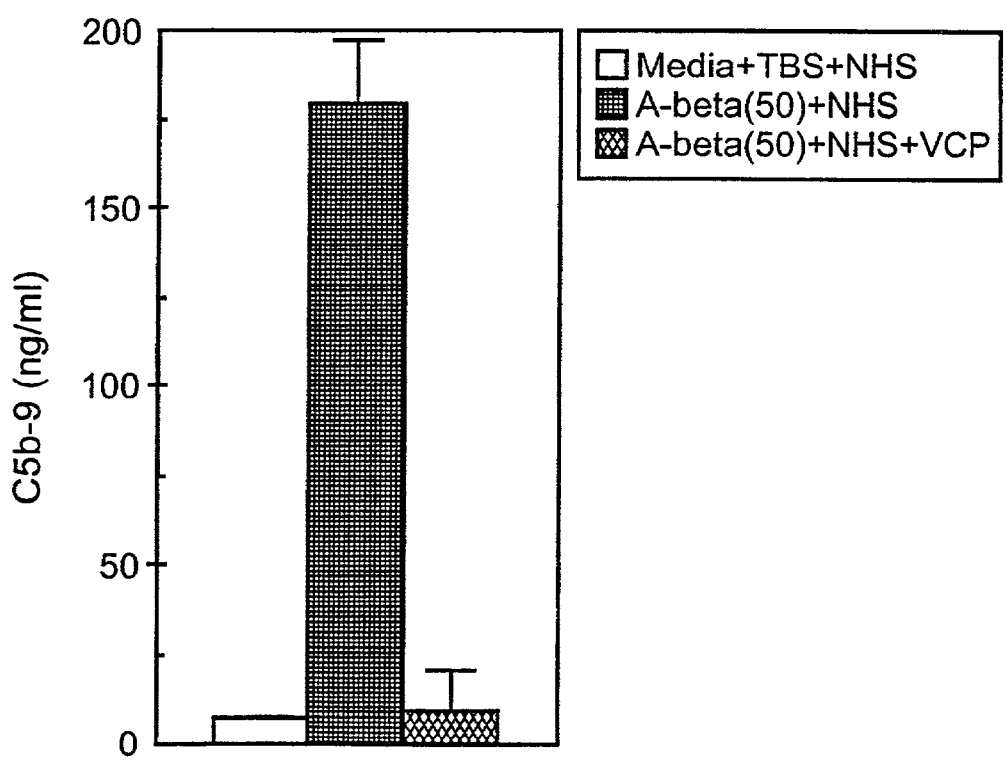
Figure 11C:
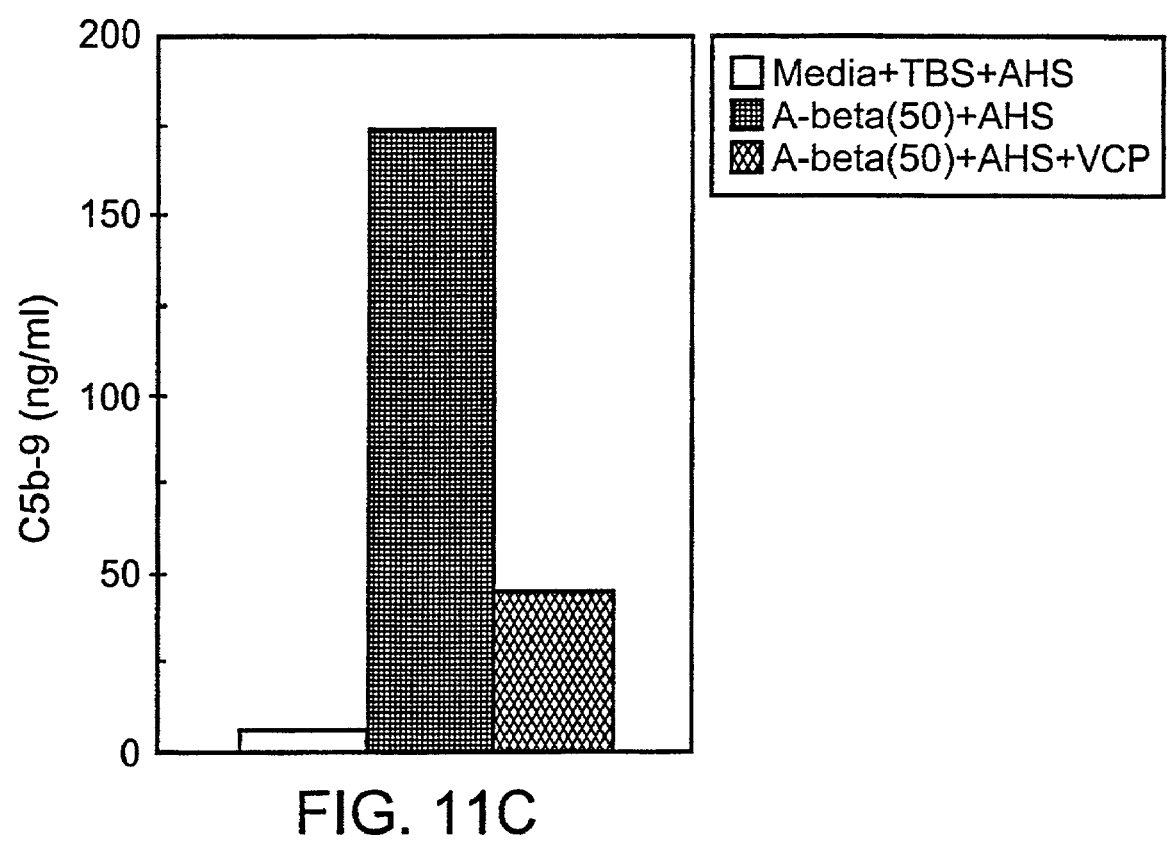

FIG. 11. Immunoassay for complement activation by Aβ. FIG. 11A. Internal controls for quantitation of results in ng/ml included standards A, B and C; and high (HPC) and low (LPC) positive controls. Also, external controls of heat activated IgG (HAG) and zymosan were included for confirmation of intact complement pathway in normal (NHS) and agammaglubulinemic (AHS) human sera. FIG. 11B. Measurement of NHS complement activation in the presence or absence of 50 μM Aβ peptide (A-beta(50)). Inhibition of complement activation by Aβ in NHS was determined by the addition of purified VCP. Background activation is demonstrated by the incubation of NHS with TBS. Standard deviation is indicated by error bars. FIG. 11C. Measurement of AHS complement activation in the presence or absence of 50 μM Aβ peptide, with or without added VCP. Background activation is demonstrated by the incubation of NHS with TBS. The addition of MEM to all reactions was necessary because VCP is solubilized in it and also MEM seems to enhance complement activation by Aβ.

Figure 12B:
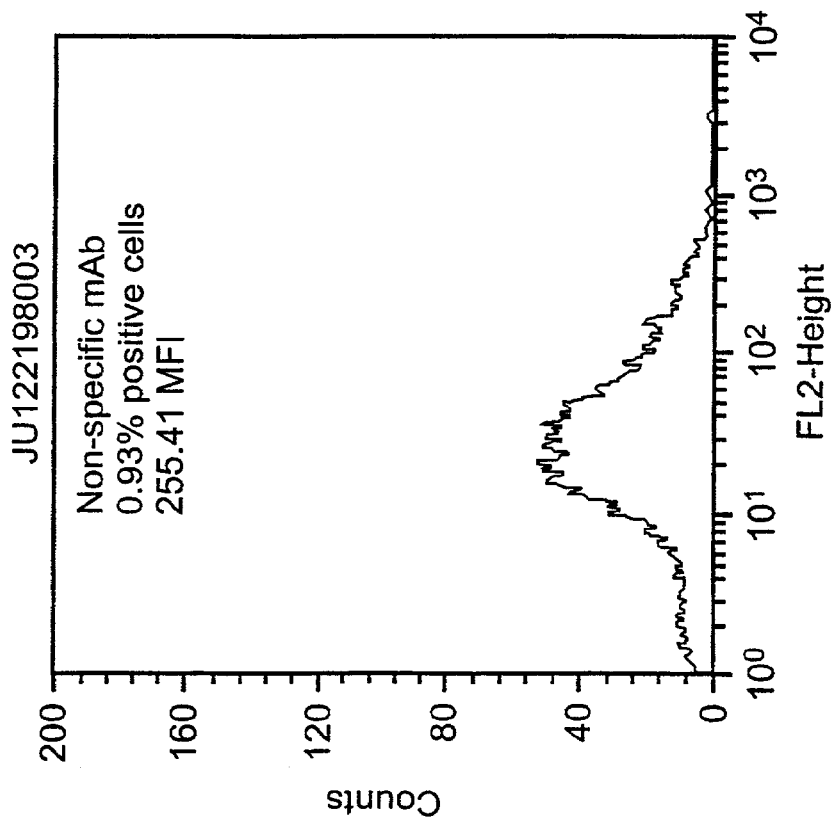
Figure 12A:
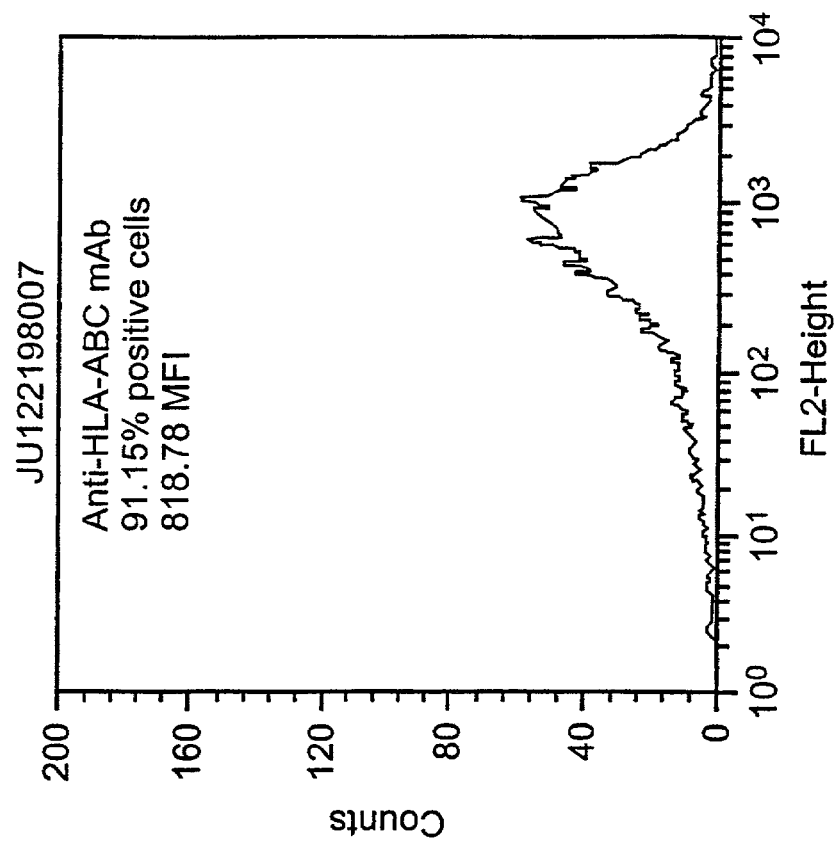
Figures 12C, 12D:
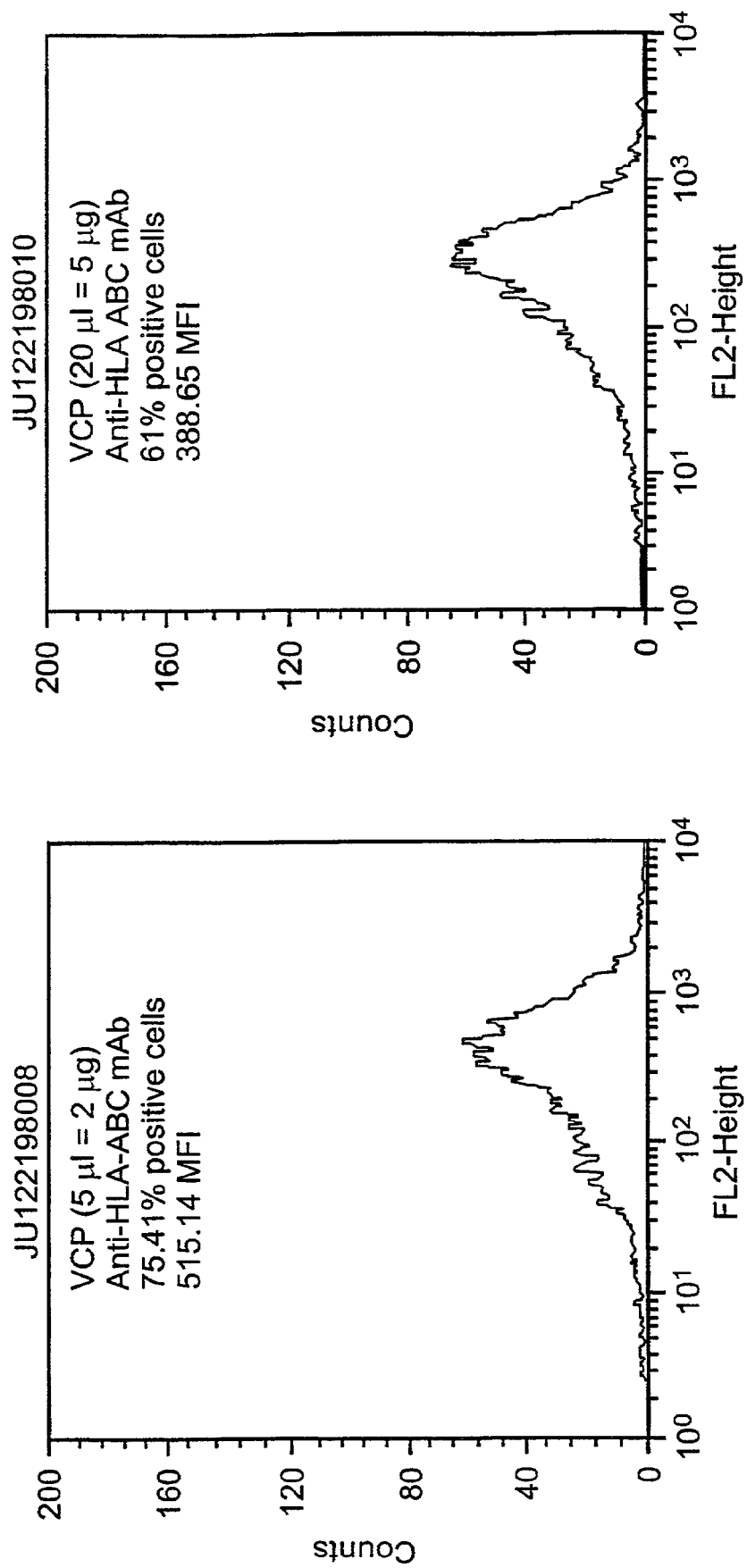

FIG. 12. Representative histograms showing the VCP is able to reduce mouse antihuman HLA class I antibody binding to HUVECs cells. The results of flow microflourimetric analysis are as follows: Panel 12A) Nonspecific mouse monoclonal antibody (isotype-matched mouse IgG2a mAb) binding to HUVECs cells (negative control) Panel 12B) Mouse monoclonal antihuman HLA-ABC antibody binding to HUVECs cells (positive control); Panel 12C) Mouse monoclonal antihuman HLA-ABC antibody binding to HUVECs cells in the presence of 5 μl (2 μg) of VCP; Panel 12D) Mouse antihuman HLA-ABC antibody to HUVECs cells in the present of 20 μl (5 μg) of VCP.

Figure 13:
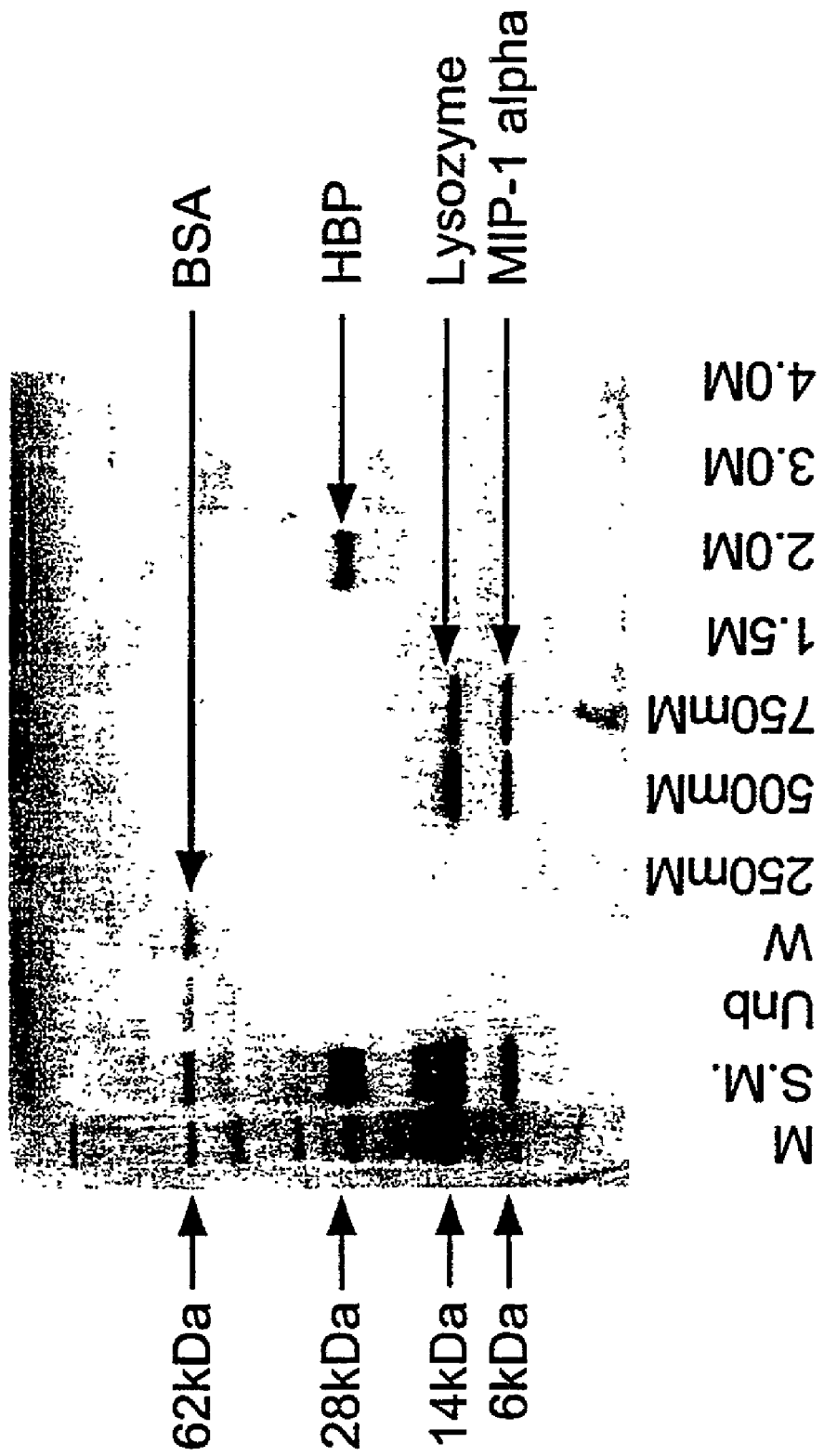
Figures 14A, 14B, 14C:
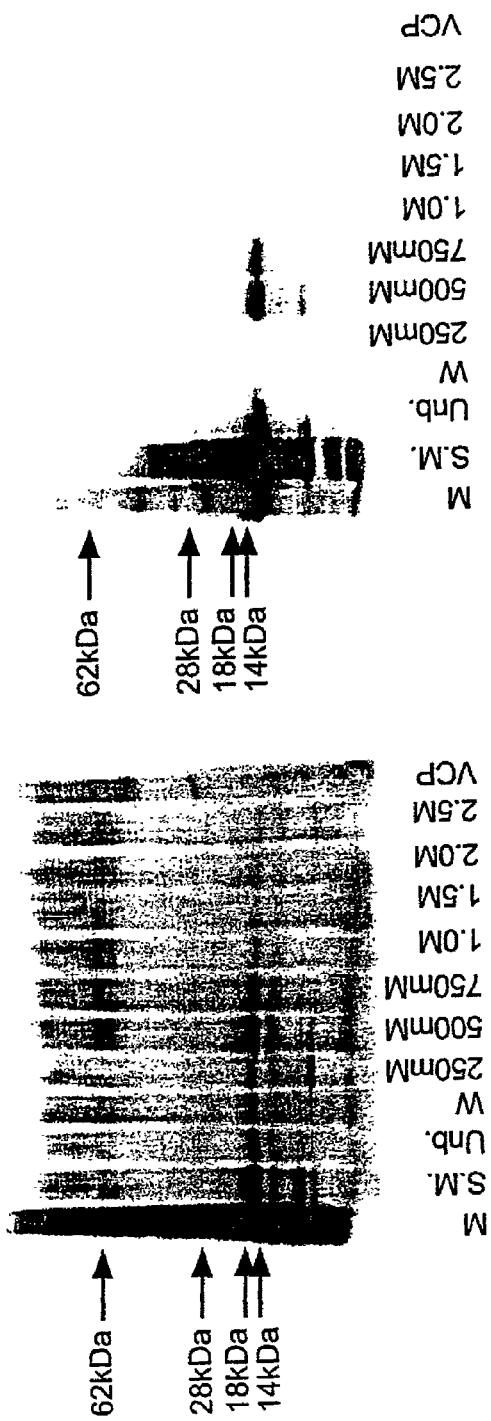
Figure 14E:
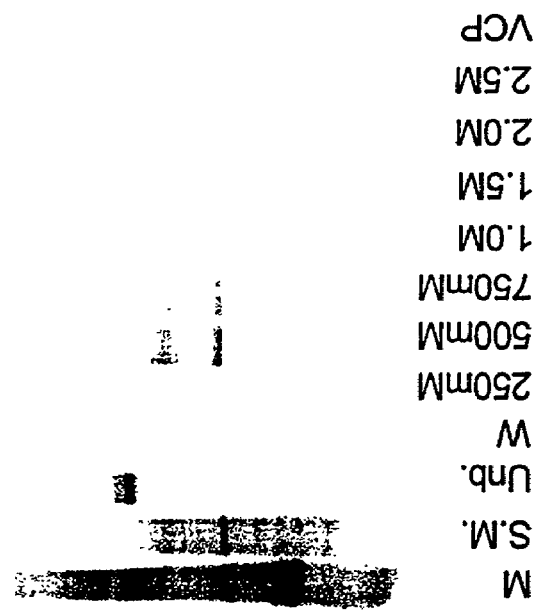
Figure 14D:
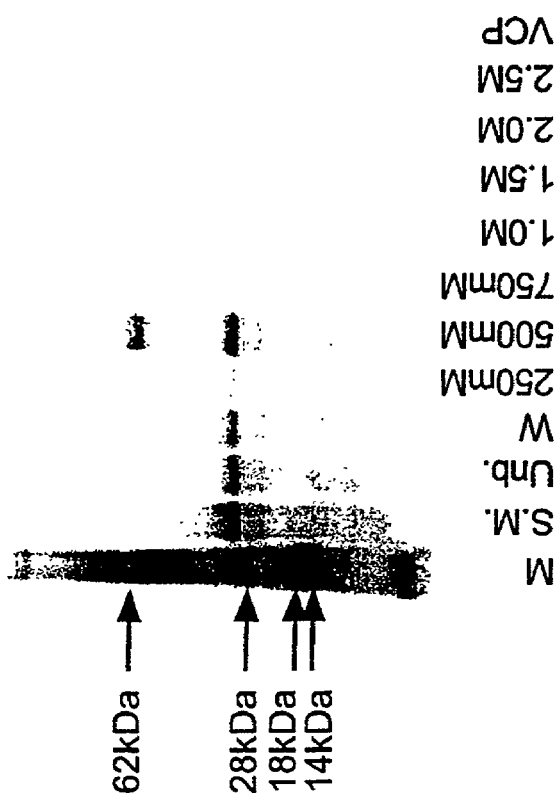
Figure 14F:
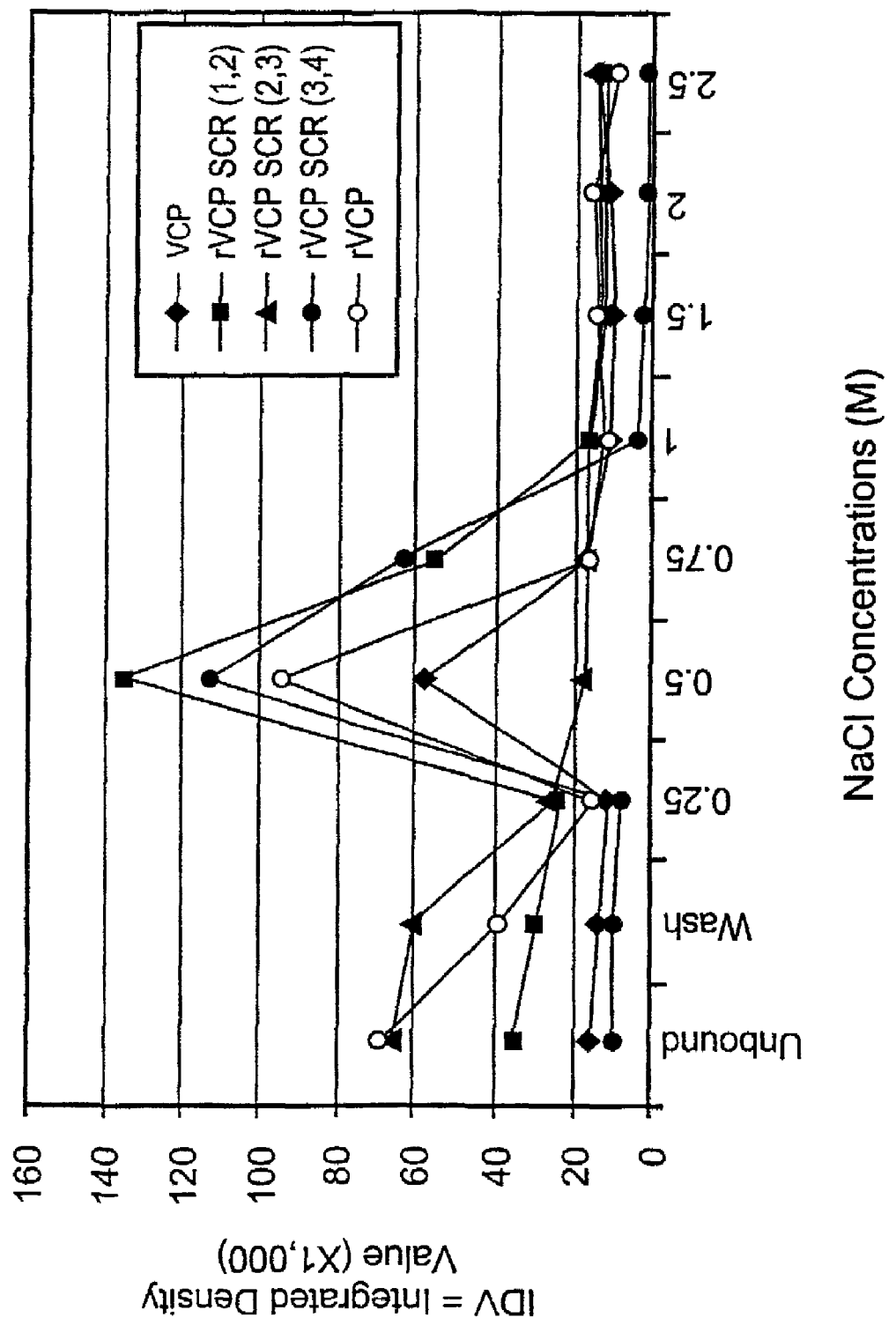

FIG. 13. PAGE analysis of the heparin binding activity of BSA, HBP, lysozyme, and MIP-1 alpha. In order to calibrate the HiTRAP heparin column, various proteins (BSA, HBP, lysozyme, and MIP-1α) with differing affinities for heparin were passed through the column and eluted with sodium chloride concentrations ranging from 250 mM to 4.0 M. M=molecular weight marker, S.M.=starting material, Unb.=unbound fraction, W=wash.

FIG. 14. PAGE analysis of the heparin binding activity of VCP and rVCPs. VCP and various rVCPs were passed through separate HiTRAP heparin columns and eluted with sodium chloride concentrations ranging from 250 mM to 2.5 M. The fractions were collected, run on SDS PAGE, silver stained, and the band densities measured. The results are shown as follows: Panel 14A) recombinant rVCP SCR (1,2) Panel 14B) recombinant rVCP SCR (2,3): Panel 14C) recombinant rVCP SCR (3,4) Panel 14D) recombinant rVCP; Panel 14E) VCP from the natural infection process. For Panels A–E, M=molecular weight marker, S.M.=starting material, Unb.=unbound fraction, W=wash, VCP=VCP from natural infection. Panel 14F) Densitometric scanning of Panels 14A–E.

FIG. 15. Sequence alignment including termini of rVCP constructs and putative heparin binding sites. Multiple alignment of the four short consensus repeats (SCR) from orthopoxviruses VAC-COP (vaccinia virus, copenhagen strain; SEQ ID NO:5) (Goebel et al., 1990 *Virology* 179:247–263), VAC-WR (vaccinia virus, western reserve strain; SEQ ID NO:6) (Kotwal, G. J. et al. 1989 *Virology* 171:579–587), CPV-GRI (cowpox virus, Russian isolate from human patient, SEQ ID NO:7) (Schelkunov, S. N., et al. 1998 *Virology* 243:432–460), CPV BRI (cowpox virus, Brighton strain; SEQ ID NO:8) (Miller, C. G., et al. 1995 *Cell Immunol.* 162:326–332), VAR-BSH (variola virus, Bangladesh strain; SEQ ID NO:9) (Massung, R. F., et al. 1994. *Virology* 201:215–240), VAR-IND (*variola major* virus, Indian strain; SEQ ID NO:10) (Schelkunov, S. N., et al. 1998 *Virology* 243:432–460), VAR-GAR (*variola minor* virus, alastrim Garcia strain; SEQ ID NO:11) (Massung, R. F., et al. 1996. *Virology* 221:291–300), and MPV-ZAI (monkeypox virus, isolated from a human patient from Zaire in 1996; SEQ ID NO:12). The putative heparin binding sites (K/R-X-K/R) are marked with solid bars, arrows indicate the termini of the rVCP constructs, and the cysteines are highlighted.

FIG. 16. Structure-function summary table of VCP, VCP homologs, and rVCPs. VCP/IMP/SPICE, MPV homology of VCP, recombinant VCP, and four recombinant segments of VCP are shown above along with whether they are able to inhibit hemolysis of sensitized sheep red blood cells and/or bind heparin (IMP=inflammation modulatory protein) Also listed are the number of positively charged amino acids (K+R) found in the protein, percentage of positively charged amino acids (% K+R) making up the protein, pI of the protein, and number of putative heparin binding sites found on the surface of the protein.

Figure 17B:
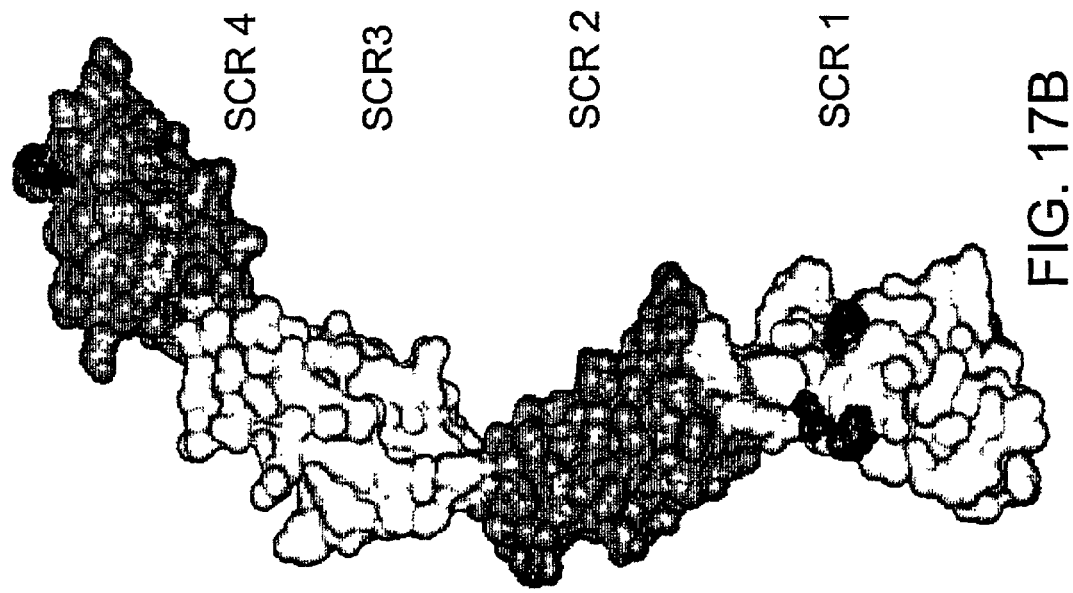
Figure 17A:
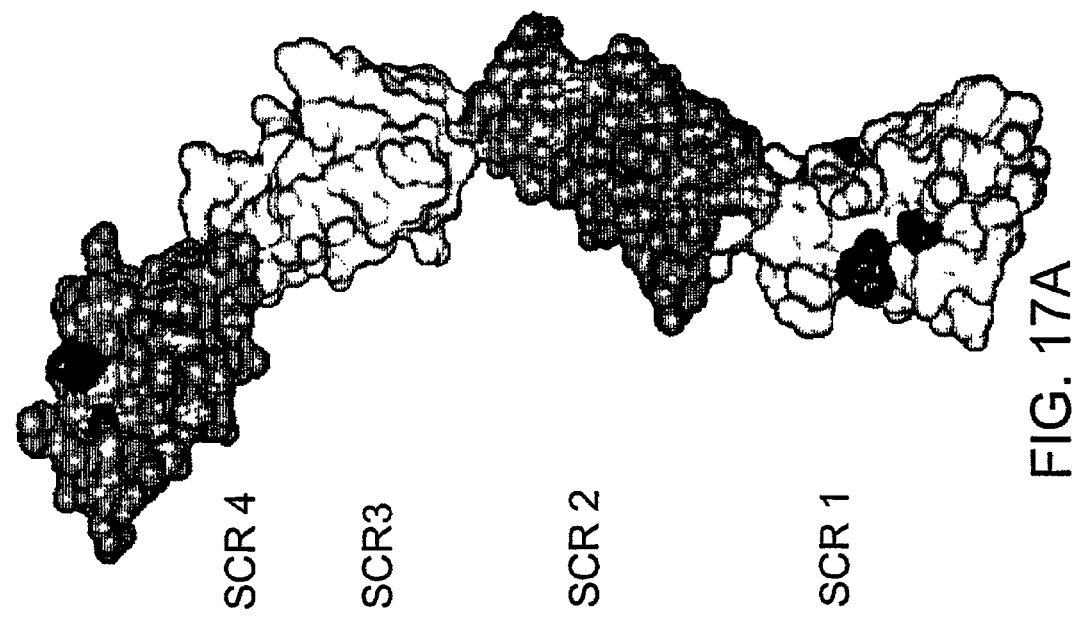

FIG. 17. VCP model showing the heparin binding sites. Front (FIG. 17A) and back (FIG. 17B) views of the modeled structure of VCP SCR (1–4) showing the heparin binding sites. In order to differentiate the extents of the individual modules, they are shaded appropriately.

DETAILED DESCRIPTION OF THE PREFERRED EMBODIMENTS OF THE INVENTION

As noted above the present invention provides a method for treating Alzheimer's disease comprising administering to a patient in need of such treatment a therapeutic amount of the protein of Formula (I):

```
M K V E S V T F L T L L G I G C V L S C C T I P S

R P I N M K F K N S V E T D A N A N Y N I G D T I

E Y L C L P G Y R K Q K M G P I Y A K C T G T G W

T L F N Q C I K R R C P S P R D I D N G Q L D I G

G V D F G S S I T Y S C N S G Y H L I G E S K S Y

C E L G S T G S M V W N P E A P I C E S V K C Q S

P P S I S N G R H N G Y E D F Y T D G S V V T Y S

C N S G Y S L I G N S G V L C S G G E W S D P P T

-continued

C Q I V K C P H P T I S N G Y L S S G F K R S Y S

Y N D N V D F K C K Y G Y K L S G S S S T C S P

G N T W K P E L P K C V R (SEQ ID NO:1)
```

The amino acid abbreviations are set forth below:

| Single-letter abbreviation | Three-letter abbreviation | Amino acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asp | Asparagine |
| P | Pro | Proline |
| Q | Glu | Glutamine |
| R | Arg | Arginine |
| S | Ser | Serine |
| T | Thr | Threonine |
| W | Trp | Tryptophan |
| V | Val | Valine |
| Y | Tyr | Tyrosine |

One skilled in the art will recognize that certain amino acids are prone to rearrangement. For example, Asp may rearrange to aspartimide and isoasparigine as described in I. Schbn et al., *Int. J. Pentide Protein Res.* 14: 485–94 (1979) and references cited therein. These rearrangement derivatives are included within the scope of the present invention. Unless otherwise indicated the amino acids are in the L configuration.

For purposes of the present invention, as disclosed and claimed herein, the following terms and abbreviations are defined as follows:

Base pair (bp)—refers to DNA or RNA. The abbreviations A,C,G, and T correspond to the 5'-monophosphate forms of the nucleotides (deoxy)adenine, (deoxy)cytidine, (deoxy)guanine, and (deoxy)thymine, respectively, when they occur in DNA molecules. The abbreviations U,C,G, and T correspond to the 5'-monophosphate forms of the nucleosides uracil, cytidine, guanine, and thymine, respectively when they occur in RNA molecules. In double stranded DNA, base pair may refer to a partnership of A with T or C with G. In a DNA/RNA heteroduplex, base pair may refer to a partnership of T with U or C with G.

Chelating Peptide—An amino acid sequence capable of complexing with a multivalent metal ion.

DNA—Deoxyribonucleic acid.

EDTA—an abbreviation for ethylenediamine tetraacetic acid.

ED50—an abbreviation for half-maximal value.

FAB-MS—an abbreviation for fast atom bombardment mass spectrometry.

Immunoreactive Protein(s)—a term used to collectively describe antibodies, fragments of antibodies capable of binding antigens of a similar nature as the parent antibody molecule from which they are derived, and single chain polypeptide binding molecules as described in PCT Application No. PCT/US 87/02208, International Publication No. WO 88/01649.

mRNA—messenger RNA.

MWCO—an abbreviation for molecular weight cut-off.

Patient—a patient is any animal, usually a mammal, preferably a human.

Plasmid—an extrachromosomal self-replicating genetic element.

PMSF—an abbreviation for phenylmethylsulfonyl fluoride.

Reading frame—the nucleotide sequence from which translation occurs "read" in triplets by the translational apparatus of tRNA, ribosomes and associated factors, each triplet corresponding to a particular amino acid. Because each triplet is distinct and of the same length, the coding sequence must be a multiple of three. A base pair insertion or deletion (termed a frameshift mutation) may result in two different proteins being coded for by the same DNA segment. To insure against this, the triplet codons corresponding to the desired polypeptide must be aligned in multiples of three from the initiation codon, i.e. the correct "reading frame" must be maintained. In the creation of fusion proteins containing a chelating peptide, the reading frame of the DNA sequence encoding the structural protein must be maintained in the DNA sequence encoding the chelating peptide.

Recombinant DNA Cloning Vector—any autonomously replicating agent including, but not limited to, plasmids and phages, comprising a DNA molecule to which one or more additional DNA segments can or have been added.

Recombinant DNA Expression Vector—any recombinant DNA cloning vector in which a promoter has been incorporated.

Replicon—A DNA sequence that controls and allows for autonomous replication of a plasmid or other vector.

RNA—ribonucleic acid.

RP-HPLC—an abbreviation for reversed-phase high performance liquid chromatography.

Transcription—the process whereby information contained in a nucleotide sequence of DNA is transferred to a complementary RNA sequence.

Translation—the process whereby the genetic information of messenger RNA is used to specify and direct the synthesis of a polypeptide chain.

Tris—an abbreviation for tris-(hydroxymethyl)aminomethane.

Treating—describes the management and care of a patient for the purpose of combating the disease, condition, or disorder and includes the administration of a compound of present invention to prevent the onset of the symptoms or complications, alleviating the symptoms or complications, or eliminating the disease, condition, or disorder. Treating obesity therefor includes the inhibition of food intake, the inhibition of weight gain, and inducing weight loss in patients in need thereof.

Vector—a replicon used for the transformation of cells in gene manipulation bearing polynucleotide sequences corresponding to appropriate protein molecules which, when combined with appropriate control sequences, confer specific properties on the host cell to be transformed. Plasmids, viruses, and bacteriophage are suitable vectors, since they are replicons in their own right. Artificial vectors are constructed by cutting and joining DNA molecules from different sources using restriction enzymes and ligases. vectors include Recombinant DNA cloning vectors and Recombinant DNA expression vectors.

X-gal—an abbreviation for 5-bromo-4-chloro-3-idolyl beta-D-galactoside.

SEQ ID NO: 1 refers to the sequence set forth in the sequence listing and means a complement-inhibiting protein of the formula:

```
M K V E S V T F L T L L G I G C V L S C C T I P S

R P I N M K F K N S V E T D A N A N Y N I G D T I

E Y L C L P G Y R K Q K M G P I Y A K C T G T G W

T L F N Q C I K R R C P S P R D I D N G Q L D I G

G V D F G S S I T Y S C N S G Y H L I G E S K S Y

C E L G S T G S M V W N P E A P I C E S V K C Q S

P P S I S N G R H N G Y E D F Y T D G S V V T Y S

C N S G Y S L I G N S G V L C S G G E W S D P P T

C Q I V K C P H P T I S N G Y L S S G F K R S Y S

Y N D N V D F K C K Y G Y K L S G S S S T C S P

G N T W K P E L P K C V R
```

(SEQ ID NO:1)

The present invention provides a method for treating Alzheimer's disease comprising administering to an organism an effective amount of a compound of Formula (I) in a dose between about 1 and 1000 μg/kg. A preferred dose is from about 10 to 100 μg/kg of active compound. A typical daily dose for an adult human is from about 0.5 to 100 mg. In practicing this method, compounds of the Formula (I) can be administered in a single daily dose or in multiple doses per day. The treatment regime may require administration over extended periods of time. The amount per administered dose or the total amount administered will be determined by the physician and depend on such factors as the nature and severity of the disease, the age and general health of the patient and the tolerance of the patient to the compound.

The instant invention further provides pharmaceutical formulations comprising compounds of the Formula (I). The proteins, preferably in the form of a pharmaceutically acceptable salt, can be formulated for parenteral administration for the therapeutic or prophylactic treatment of obesity. For example, compounds of the Formula (I) can be admixed with conventional pharmaceutical carriers and excipients. The compositions comprising claimed proteins contain from about 0.1 to 90% by weight of the active protein, preferably in a soluble form, and more generally from about 10 to 30%. Furthermore, the present proteins may be administered alone or in combination with other anti-Alzheimer's agents or agents useful in treating dementia (i.e., improving cognitive function). Preferred agents for use in combination with the protein of the present invention for treating Alzheimer's disease include acetylcholine precursors (e.g., choline chloride and phosphatidyl choline (lecithin)); cholinergic agonists (e.g., acetylcholine, acetyl-L-carnitine, anatoxine a, arecoline, bethanecol, carbachol, decamethonium, 1,1-dimethyl-4-phenyl-piperazinium, cis-Dioxolane, epibatidine, epiboxidine, methacholine, methylcarbamylcholine, methylfurtrethonium, metoclopramide, muscarine, nicotine, oxotremorine, pilocarpine, and pharmaceutically acceptable salts thereof); cholinesterase inhibitors (e.g., ambenonium, adrophonium, methylphysostigmine, neostigmine, pyridostigmine, and pharmaceutically acceptable salts thereof) and acetylcholinesterase inhibitors (e.g., physostigmine, tacrine (1,2,3,4-tetrahydro-9-aminoacridine), galanthamine, and pharmaceutically acceptable salts thereof).

For intravenous (IV) use, the protein is administered in commonly used intravenous fluid(s) and administered by infusion. Such fluids as, for example, physiological saline, Ringer's solution or 5% dextrose solution can be used.

For intramuscular preparations, a sterile formulation, preferably a suitable soluble salt form of a protein of the Formula (i), for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

The proteins for use in the presently claimed invention may be prepared by construction of the DNA encoding the claimed protein and thereafter expressing the DNA in recombinant cell culture. Techniques for making substitutional mutations at predetermined sites in DNA having a known sequence are well known, for example M13 primer mutagenesis. The mutations that might be made in the DNA encoding the protein of the present invention must not place the sequence out of reading frame and preferably will not create complementary regions that could produce secondary mRNA structure. See DeBoer et al., EP 75,444A (1983).

The protein of the present invention may be produced either by recombinant DNA technology or well known chemical procedures, such as solution or solid-phase peptide synthesis, or semi-synthesis in solution beginning with protein fragments coupled through conventional solution methods.

A. Solid Phase

The synthesis of the protein of the present invention may proceed by solid phase peptide synthesis or by recombinant methods. The principles of solid phase chemical synthesis of polypeptides are well known in the art and may be found in general texts in the area such as Dugas, H. and Penney, C., *Bioorganic Chemistry*, Springer-Verlag, New York, pgs. 54–92 (1981). For example, peptides may be synthesized by solid-phase methodology utilizing an PE-Applied Biosystems 430A peptide synthesizer (commercially available from Applied Biosystems, Foster City Calif.) and synthesis cycles supplied by Applied Biosystems. Boc amino acids and other reagents are commercially available from PE-Applied Biosystems and other chemical supply houses. Sequential Boc chemistry using double couple protocols are applied to the starting p-methyl benzhydryl amine resins for the production of C-terminal carboxamides. For the production of C-terminal acids, the corresponding PAM resin is used. Arginine, Asparagine, Glutamine, Histidine and Methionine are coupled using preformed hydroxy benzotriazole esters. The following side chain protection may be used:

Arg, Tosyl
Asp, cyclohexyl or benzyl
Cys, 4-methylbenzyl
Glu, cyclohexyl
His, benzyloxymethyl
Lys, 2-chlorobenzyloxycarbonyl
Met, sulfoxide
Ser, Benzyl
Thr, Benzyl
Trp, formyl
Tyr, 4-bromo carbobenzoxy Boc deprotection may be accomplished with trifluoroacetic acid (TFA) in methylene chloride. Formyl removal from Trp is accomplished by treatment of the peptidyl resin with 20% piperidine in dimethylformamide for 60 minutes at VC. Met(O) can be reduced by treatment of the peptidyl resin with TFA/dimethylsulfide/conHC1(95/5/1) at 25° C. for 60 minutes. Following the above pre-treatments, the peptides may be further deprotected and cleaved from the resin with anhydrous hydrogen fluoride containing a mixture of 10% m-cresol or m-cresol/1 0% p-thiocresol or m-cresol/p-thiocresol/dimethylsulfide. Cleavage of the side chain protecting group(s) and of the peptide from the resin is carried out at zero degrees Centigrade or below, preferably −20° C. for thirty minutes followed by thirty minutes at 0° C. After removal of the HF, the peptide/resin is washed with ether. The peptide is extracted with glacial acetic acid and lyophilized. Purification is accomplished by reverse-phase C18 chromatography (Vydac) column in 0.1% TFA with a gradient of increasing acetonitrile concentration.

One skilled in the art recognizes that the solid phase synthesis could also be accomplished using the FMOC strategy and a TFA/scavenger cleavage mixture.

B. Recombinant Synthesis

The protein of the present invention may also be produced by recombinant methods. Recombinant methods are preferred if a high yield is desired. The basic steps in the recombinant production of protein include:

a) construction of a synthetic or semi-synthetic (or isolation from natural sources) DNA encoding the protein of the present invention, b) integrating the coding sequence into an expression vector in a manner suitable for the expression of the protein either alone or as a fusion protein, c) transforming an appropriate eukaryotic or prokaryotic host cell with the expression vector, and d) recovering and purifying the recombinantly produced protein.

2.a. Gene Construction

Synthetic genes, the in vitro or in vivo transcription and translation of which will result in the production of the protein may be constructed by techniques well known in the art. owing to the natural degeneracy of the genetic code, the skilled artisan will recognize that a sizable yet definite number of DNA sequences may be constructed which encode the claimed proteins. In the preferred practice of the invention, synthesis is achieved by recombinant DNA technology.

Methodology of synthetic gene construction is well known in the art. For example, see Brown, et al. (1979) *Methods in Enzymology*, Academic Press, N.Y., Vol. 68, pp. 109–151. The DNA sequence corresponding to the synthetic claimed protein gene may be generated using conventional DNA synthesizing apparatus such as the Applied Biosystems Model 380A or 380B DNA synthesizers (commercially available from Applied Biosystems, Inc., 850 Lincoln Center Drive, Foster City, Calif. 94404).

It may be desirable in some applications to modify the coding sequence of the claimed protein so as to incorporate a convenient protease sensitive cleavage site, e.g., between the signal peptide and the structural protein facilitating the controlled excision of the signal peptide from the fusion protein construct.

The gene encoding the claimed protein may also be created by using polymerase chain reaction (PCR). The template can be a cDNA library (commercially available from CLONETECH or STRATAGENE) or mRNA isolated from human adipose tissue. Such methodologies are well known in the art Maniatis, et al. *Molecular Cloning: A Laboratory Manual*, Cold Spring Harbor Press, Cold Spring Harbor Laboratory, Cold Spring Harbor, N.Y. (1989).

2.b. Direct Expression or Fusion Protein

The claimed protein may be made either by direct expression or as fusion protein comprising the claimed protein followed by enzymatic or chemical cleavage. A variety of peptidases (e.g. trypsin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., Carter P., Site Specific Proteolysis of Fusion Proteins, Ch. 13 in *Protein Purification: From Molecular Mechanisms to Large Scale Processes*, American Chemical Soc., Washington, D.C. (1990).

2.c. Vector Construction

Construction of suitable vectors containing the desired coding and control sequences employ standard ligation techniques. Isolated plasmids or DNA fragments are cleaved, tailored, and relegated in the form desired to form the plasmids required.

To effect the translation of the desired protein, one inserts the engineered synthetic DNA sequence in any of a plethora of appropriate recombinant DNA expression vectors through the use of appropriate restriction endonucleases. The claimed protein is a relatively large protein. A synthetic coding sequence is designed to possess restriction endonuclease cleavage sites at either end of the transcript to facilitate isolation from and integration into these expression and amplification and expression plasmids. The isolated cDNA coding sequence may be readily modified by the use of synthetic linkers to facilitate the incorporation of this sequence into the desired cloning vectors by techniques well known in the art. The particular endonucleases employed will be dictated by the restriction endonuclease cleavage pattern of the parent expression vector to be employed. The choice of restriction sites are chosen so as to properly orient the coding sequence with control sequences to achieve proper in-frame reading and expression of the claimed protein.

In general, plasmid vectors containing promoters and control sequences which are derived from species compatible with the host cell are used with these hosts. The vector ordinarily carries a replication site as well as marker sequences which are capable of providing phenotypic selection in transformed cells. For example, *E. coli* is typically transformed using pBR322, a plasmid derived from an *E. coli* species (Bolivar, et al., *Gene* 2: 95 (1977)). Plasmid pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA technology.

The desired coding sequence is inserted into an expression vector in the proper orientation to be transcribed from a promoter and ribosome binding site, both of which should be functional in the host cell in which the protein is to be expressed. An example of such an expression vector is a plasmid described in Belagaje et al., U.S. Pat. No. 5,304,493, the teachings of which are herein are incorporated by reference. The gene encoding A-C-B proinsulin described in U.S. Pat. No. 5,304,493 can be removed from the plasmid pRB182 with restriction enzymes NdeI and BamHI. The genes encoding the protein of the present invention can be inserted into the plasmid backbone on a NdeI/BamHI restriction fragment cassette.

2.d. Procaryotic Expression

In general, procaryotes are used for cloning of DNA sequences in constructing the vectors useful in the invention.

For example, *E. coli* K12 strain 294 (ATCC No. 31446) is particularly useful. other microbial strains which may be used include *E. coli* B and *E. coli* X1776 (ATCC No. 31537). These examples are illustrative rather than limiting.

Prokaryotes also are used for expression. The aforementioned strains, as well as *E. coli* W3110 (prototrophic, ATCC No. 27325), bacilli such as *Bacillus subtilis*, and other enterobacteriaceae such as *Salmonella typhimurium* or *Serratia marcescans*, and various *Pseudomonas* species may be used. Promoters suitable for use with prokaryotic hosts include the β-lactamase (vector pGX2907 [ATCC 39344] contains the replicon and β-lactamase gene) and lactose promoter systems (Chang et al., *Nature*, 275:615 (1978); and Goeddel et al., *Nature* 281:544 (1979)), alkaline phosphatase, the tryptophan (trp) promoter system (vector pATH1 [ATCC 37695] is designed to facilitate expression of an open reading frame as a trpE fusion protein under control of the trp promoter) and hybrid promoters such as the tac promoter (isolatable from plasmid pDR540 ATCC-37282). However, other functional bacterial promoters, whose nucleotide sequences are generally known, enable one of skill in the art to ligate them to DNA encoding the protein using linkers or adaptors to supply any required restriction sites. Promoters for use in bacterial systems also will contain a Shine-Dalgarno sequence operably linked to the DNA encoding protein.

2.e. Eucaryotic Expression

The protein may be recombinantly produced in eukaryotic expression systems. Preferred promoters controlling transcription in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. β-actin promoter. The early and late promoters of the SV40 virus are conveniently obtained as an SV40 restriction fragment which also contains the SV40 viral origin of replication. Fiers, et al., *Nature,* 273:113 (1978). The entire SV40 genome may be obtained from plasmid pBRSV, ATCC 45019. The immediate early promoter of the human cytomegalovirus may be obtained from plasmid pCMBP (ATCC 77177). Of course, promoters from the host cell or related species also are useful herein.

Transcription of a DNA encoding the claimed protein by higher eukaryotes is increased by inserting an enhancer sequence into the vector. Enhancers are cis-acting elements of DNA, usually about 10–300 bp, that act on a promoter to increase its transcription. Enhancers are relatively orientation and position independent having been found 51 (Laimins, L. et al., *PNAS* 78:993 (1981)) and 3' (Lusky, M. L., et. al., *Mol. Cell Bio.* 3:1108 (1983)) to the transcription unit, within an intron (Banerji, J. L. et al., *Cell* 33:729 (1983)) as well as within the coding sequence itself (Osborne, T. F., et al., *Mol, Cell Bio.,* 4:1293 (1984)). Many enhancer sequences are now known from mammalian genes (globin, RSV, SV40, EMC, elastase, albumin, a-fetoprotein and insulin). Typically, however, one will use an enhancer from a eukaryotic cell virus. Examples include the SV40 late enhancer, the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells from other multicellular organisms) will also contain sequences necessary for the termination of transcription which may affect mRNA expression. These regions are transcribed as polyadenylated segments in the untranslated portion of the mRNA encoding protein. The 3' untranslated regions also include transcription termination sites.

Expression vectors may contain a selection gene, also termed a selectable marker. Examples of suitable selectable markers for mammalian cells are dihydrofolate reductase (DHFR, which may be derived from the BalII/HindIII restriction fragment of pJOD-10 [ATCC 68815]), thymidine kinase (herpes simplex virus thymidine kinase is contained on the BamHI fragment of vP-5 clone [ATCC 2028]) or neomycin (G418) resistance genes (obtainable from pNN414 yeast artificial chromosome vector [ATCC 37682]). When such selectable markers are successfully transferred into a mammalian host cell, the transfected mammalian host cell can survive if placed under selective pressure. There are two widely used distinct categories of selective regimes. The first category is based on a cell,s metabolism and the use of a mutant cell line which lacks the ability to grow without a supplemented media. Two examples are: CHO DHFR$^-$ cells (ATCC CRL-9096) and mouse LTK$^-$ cells (L-M(TK-) ATCC CCL-2.3). These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in nonsupplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., *J. Molec. Appl. Genet.* 1: 327 (1982), mycophenolic acid, Mulligan, R. C. and Berg, P. *Science* 209:1422 (1980), or hygromycin, Sugden, B. et al., *Mol. Cell. Biol.* 5:410–413 (1985). The three examples given above employ bacterial genes under eukaryotic control to convey resistance to the appropriate drug G418 or neomycin (geneticin), xgpt (mycophenolic acid) or hygromycin, respectively.

A preferred vector for eucaryotic expression is pRc/CMV. pRc/CMV is commercially available from Invitrogen Corporation, 3985 Sorrento Valley Blvd., San Diego, Calif. 92121. To confirm correct sequences in plasmids constructed, the ligation mixtures are used to transform *E. coli* K12 strain DH5a (ATCC 31446) and successful transformants selected by antibiotic resistance where appropriate. Plasmids from the transformants are prepared, analyzed by restriction and/or sequence by the method of messing, et al., *Nucleic Acids Res.* 9:309 (1981).

Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al., *Molecular Cloning: A Laboratory Manual*, Cold Spring Harbor Press, Cold Spring Harbor Laboratory, Cold Spring Harbor, N.Y. (1989), or *Current Protocols in Molecular Biology* (1989) and supplements.

Preferred suitable host cells for expressing the vectors encoding the claimed proteins in higher eukaryotes include: African green monkey kidney line cell line transformed by SV40 (COS-7, ATCC CRL-1651); transformed human primary embryonal kidney cell line 293, (Graham, F. L. et al., *J. Gen Virol.* 36:59–72 (1977), *Virology* 77:319–329, *Virology* 86:10–21); baby hamster kidney cells (BHK-21(C-13), ATCC CCL-10, *Virology* 16:147 (1962)); chinese hamster ovary cells CHO-DHFR-(ATCC CRL-9096), mouse Sertoli cells (TM4, ATCC CRL-1715, *Biol. Reprod.* 23:243–250 (1980)); african green monkey kidney cells (VERO 76, ATCC CRL-1587); human cervical epitheloid carcinoma cells (HeLa, ATCC CCL-2); canine kidney cells (MDCK, ATCC CCL-34); buffalo rat liver cells (BRL 3A, ATCC CRL-1442); human diploid lung cells (WI-38, ATCC CCL-75); human hepatocellular carcinoma cells (Hep G2, ATCC HB-8065); and mouse mammary tumor cells (MMT 060562, ATCC CCL51).

2.f. Yeast Expression

In addition to prokaryotes, eukaryotic microbes such as yeast cultures may also be used. *Saccharomyces cerevisiae*, or common baker's yeast is the most commonly used eukaryotic microorganism, although a number of other strains are commonly available. For expression in *Saccharomyces*, the plasmid YRp7, for example, (ATCC-40053, Stinchcomb, et al., *Nature* 282:39 (1979); Kingsman et. al., *Gene* 7:141 (1979); Tschemper et al., *Gene* 10:157 (1980)) is commonly used. This plasmid already contains the trp gene which provides a selection marker for a mutant strain of yeast lacking the ability to grow in tryptophan, for example ATCC no. 44076 or PEP4-1 (Jones, *Genetics* 85:12 (1977)).

Suitable promoting sequences for use with yeast hosts include the promoters for 3-phosphoglycerate kinase (found on plasmid pAP12BD ATCC 53231 and described in U.S. Pat. No. 4,935,350, Jun. 19, 1990) or other glycolytic enzymes such as enolase (found on plasmid pAC1 ATCC 39532), glyceraldehyde-3-phosphate dehydrogenase (derived from plasmid pHcGAPC1 ATCC 57090, 57091), *zymomonas mobilis* (U.S. Pat. No. 5,000,000 issued Mar. 19, 1991), hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein (contained on plasmid vector pCL28XhoLHBPV ATCC 39475, U.S. Pat. No. 4,840,896), glyceraldehyde 3-phosphate dehydrogenase, and enzymes responsible for maltose and galactose (GALI found on plasmid pRY121 ATCC 37658) utilization. Suitable vectors and promoters for use in yeast expression are further described in R. Hitzeman et al., European Patent Publication No 73,657A. Yeast enhancers such as the UAS Gal from *Saccharomyces cerevisiae* (found in conjunction with the CYC1 promoter on plasmid YEpsec-hilbeta ATCC 67024), also are advantageously used with yeast promoters.

In a preferred embodiment, a DNA molecule encoding the present invention is as shown below.

peptide can activate both the classical (antibody-independent) and alternate pathways of complement activation. The proposed complement activation is due to the binding of Aβ to the complement components, Clq and C3, respectively, which initiate formation of the proinflammatory C5a and C5b-9 membrane attack complex. In this example, we have investigated the in vitro findings for the likely complement-dependent proinflammatory properties of the Alzheimer's disease Aβ peptide. We have performed experiments using

```
-51 TTTTTATTATTTGTACGATGTCCAGGATAACATTTTTACGGATAAATAAAT
    ATGAAGGTGGAGAGCGTGACGTTCCTGACATTGTTGGGAATAGGATGCGTTCTATCATGCTGTACT    66
    M  K  V  F  S  V  T  F  L  T  L  L  G  I  G  C  V  L  S  C  C  T     22

ATTCCGTCACGACCCATTAATATGAAATTTAAGAATAGTGTGGAGACTGATGCTAATGCTAATTAC    132
    I  P  S  R  P  I  N  M  K  F  K  N  S  V  E  T  D  A  N  A  N  Y     44

AACATAGGAGACACTATAGAATATCTATGTCTACCTGGATACAGAAAGCAAAAAATGGGACCTATA    198
    N  I  G  D  T  I  E  Y  L  C  L  P  G  Y  R  K  Q  K  M  G  P  I     66

TATGCTAAATGTACAGGTACTGGATGGACACTCTTTAATCAATGTATTAAACGGAGATGCCCATCG    264
    Y  A  K  C  T  C  I  C  W  T  L  F  N  Q  C  I  K  R  R  C  P  S     88

CCTCGAGATATCGATAATGGCCAACTTGATATTGGTGGAGTAGACTTTGGCTCTAGTATAACGTAC    330
    P  R  D  I  D  N  G  Q  L  D  I  G  G  V  D  F  G  S  S  I  T  Y     110

TCTTGTAATAGCGGATATCATTTGATCGGTGAATCTAAATCGTATTGTGAATTAGGATCTACTGGA    396
    S  C  N  S  G  Y  H  L  I  G  E  S  K  S  Y  C  E  L  G  S  T  G     132

TCTATGGTATGGAATCCCGAGGCACCTATTTGTGAATCTGTTAAATGCCAATCCCCTCCATCTATA    462
    S  M  V  W  N  P  E  A  P  I  C  F  S  V  K  C  Q  S  P  P  S  I     154

TCCAACGGAAGACATAACGGATACGAGGATTTTTATACCGATGGGAGCGTTGTAACTTATAGTTGC    528
    S  N  G  R  H  N  G  Y  E  D  F  Y  T  D  G  S  V  V  T  Y  S  C     176

AATAGTGGATATTCGTTGATTGGTAACTCTGGTGTCCTGTGTTCAGGAGGAGAATGGTCCGATCCA    594
    N  S  G  Y  S  L  I  G  N  S  G  V  L  C  S  G  G  E  W  S  D  P     198

CCCACGTGTCAGATTGTTAAATGTCCACATCCTACAATATCAAACGGATACTTGTCTAGCGGGTTT    660
    P  T  C  Q  I  V  K  C  P  H  P  T  I  S  N  G  Y  L  S  S  G  F     220

AAAAGATCATACTCATACAACGACAATGTAGACTTTAAGTGCAAGTACGGATATAAACTATCTGGT    726
    K  R  S  Y  S  Y  N  D  N  V  D  F  K  C  K  Y  G  Y  K  L  S  G     242

TCCTCATCATCTACTTGCTCTCCAGGAAATACATGGAAGCCGGAACTTCCAAAATGTGTACGC      792
    S  S  S  S  T  C  S  P  G  N  T  W  K  P  E  L  P  K  C  V  R        264
```

(SEQ ID NO:2).

This DNA molecule is disclosed in U.S. Pat. No. 5,157,110, the contents of which are incorporated herein by reference.

In addition, labeled VCP can be used as a probe to detect amyloid plaques in situ or post mortem. In such an assay the VCP would bind to the complement components in the plaque. Subsequent detection of the label would be indicative of the presence of amyloid plaques. For use in such a diagnostic method, VCP may be labeled with any suitable label known in the art. Particularly preferred labels include fluorescent labels (e.g., fluorescein) and enzymatic labels (e.g., peroxidase).

The following examples are presented in order to more fully illustrate the preferred embodiments of the invention. They should in no way be construed, however, as limiting the broad scope of the invention.

EXAMPLE 1

The amyloid plaque is the hallmark of Alzheimer's disease (AD). The transmembrane domain and a portion of the C-terminus (Aβ) of the amyloid precursor protein (APP), are known to form the nucleus of the amyloid plaque. It has been demonstrated recently, using in vitro assays, that the Aβ congenic C5-deficient and C5-sufficient mice injected with synthetic Aβ and recombinant polypeptide (C-100) containing Aβ. Injection of C-100 into C5-sufficient mice induced a clear increase in the number of polymorphonuclear cells (neutrophils) at the site of injection, due to complement activation and the subsequent release of proinflammatory chemotactic factors. In sharp contrast, the C5-deficient mice did not show any increase in cellular influx. The vaccinia virus complement control protein (VCP), an inhibitor of both the classical and alternate pathway can down-regulate the biologically significant activation of complement by Aβ, as demonstrated by an in vitro immunoassay. The therapeutic down-regulation of Aβ-caused complement activation could greatly alleviate the progression of some of the chronic neurodegeneration characteristic of AD.

The aim of the experiments detailed in this Example was to first determine whether the activation of complement by Aβ can occur in a mouse connective tissue air-pouch model developed to determine the qualitative and quantitative changes in influx of immune cells. Our rationale was that the immune cells within the connective tissue of different organs arise from the same lineage. We were also interested in determining whether a viral inhibitor (of both the classical and alternate pathway) could block the complement activation by Aβ. The viral inhibitor, termed vaccinia virus complement control protein (VCP) is structurally similar to the family of the human complement control proteins containing short consensus repeat (Kotwal, G. J. & Moss, B. (1988) *Nature* 335:176–178). Unlike the large and complex, human complement control proteins, VCP is much smaller and it retains the functionality of the human proteins. Functionally VCP resembles the first complement receptor (CR1) as it is able to bind both to the third component and the fourth component of the complement system (Kotwal, G. J. (1996) *The Immunologist* 4:157–164; Kotwal, G. J. et al. (1990) *Science* 250:827830; McKenzie, R. et al. *J. Infect Dis.* 166:1245–1250). Thus, VCP can effectively block the complement pathway at an early stage following complement activation and thereby potentially block the downstream events leading to the formation of C5a and membrane attack complex.

The homologue of VCP in cowpox virus has been termed as the inflammation modulatory protein (IMP) (Miller, C. G. et al. (1997) *Virology* 229:126–133). IMP has been shown in a mouse air-pouch model to significantly reduce the influx of inflammatory cells and drastically diminish the tissue damage elicited by cowpox virus infection (Kotwal, G. J., et al. (1998) *Mol. Cell. Biochem.* 185:39–46). We report here that the Aβ is capable of causing a greater influx of immune cells in a mouse model, described earlier (id.), in the presence of the fifth complement component but not in its absence. This cause and effect relation suggests that the in vitro findings are biologically significant. Furthermore, we show that the Aβ activated complement activity can be blocked by VCP.

Materials and Methods

Aβ Fiber Formation

100 μg of Aβ$_{1-42}$ (QCB, Hopkinton, Mass.) was slowly solubilized in 25 μl double distilled water. After solubilization was complete, 25 μl of 2× TBS (Tris-buffered saline), pH 7.4, (100 mM Tris, 300 mM NaCl) was slowly titrated and mixed, giving a final Aβ$_{1-42}$ concentration of 2 μg/μl (444 μM). The peptide was incubated at 24° C. for approximately 2–3 days to allow for fibril formation.

Construction of pAPPc Used for Cell-Free Transcription-Translation

A pUC18 plasmid containing the coding sequence for the C-terminal 100 amino acids of APP(C-100) inserted into an EcoRI restriction site (pFB68L) was used as a template for cloning into pTM3 (FIG. 5). Forward (JD01F) and reverse (JDOIR) primers were designed and synthesized (Bio-Synthesis, Lewisville, Tex.) for use in PCR with pFB68L as the template. The primers were designed with two base pair changes so that the 1.1 kb PCR product would be a cDNA of the APP C-terminus with two new restriction sites, one at the 5'(NcoI) and one at the 3' (Sal/I) end. After purification of the PCR product, it and plasmid pTM3 were digested with NcoI and Sal/I and ligated with T4 DNA ligase (Gibco BRL, Gaithersburg, Md.). This resulted in a recombinant plasmid, pAPPc, which contained within the original multiple cloning site (MCS) the APP C-terminus under the transcriptional control of a T7 bacteriophage promoter (pT7) and termination sequence (T7t). An incorporated encephalomyocarditis virus translational enhancer leader sequence (EMC) served in lieu of a 5' cap for the mRNA. Other features of the plasmid include a guanosyl phosphoribosyl transferase (GPT) gene under the control of The 7.5 kbp vaccinia promoter (p7.5K) for positive selection of the plasmid in eukaryotic cells. The 5' and flanking sequences of the vaccinia virus thymidine kinase (TK) gene are required for homologous recombination to generate a recombinant TK-negative vaccinia virus. A bacterial origin of replication (ori) is required for plasmid replication in transfected bacteria and an ampicillin-resistance gene (Amp$^r$) for selection of transformed bacteria.

The new recombinant plasmid, pAPPc, was transformed into competent *E. coli* JM 105 (Gibco BRL) and transformants were selected for their ability to form colonies on media containing ampicillin. Colonies were selected and further amplified before isolation of the plasmid DNA by alkaline lysis minipreparation (Maniatis, T. et al. (1984) *Molecular Cloning: A Laboratory Manual*. Cold Spring Harbor Press, New York, p. 363). A clone transformed with pAPPc, as determined by restriction analysis, was amplified and plated on selective media to analyze for purity (FIG. 6A). Twelve colonies were chosen and the plasmid DNA amplified and digested as before and checked for homogeneity on an agarose gel (FIG. 6B) and by Southern hybridization (FIG. 6C) (Southern, E. M. (1975) *J. Mol. Biol.* 98:503–517). The correct sequence of the inserted DNA was confirmed by the dideoxy chain-terminating method (Sanger, F. et al., (1977) *Proc. Natl. Acad. Sci. USA* 74:5463–5467) using the Fidelity DNA Sequencing System manufactured by Oncor (Gaithersburg, Md.) (FIG. 7). Five sets of primers from within the known sequence of APP were utilized for this sequencing (arrows in FIG. 7).

In Vitro Coupled Transcription/Translation of pAPPc to Yield C-100

A coupled wheat germ extract transcription/translation reaction system containing T7 RNA polymerase (Promega, Madison, Wis.) was used for expression of pAPPc. This system allows for transcription of a DNA under the control of a T7 promoter and translation of the produced mRNA all in one reaction tube. The addition of a radiolabelled amino acid to the mixture allows for labeling of all newly synthesized polypeptides. Manufacturer's suggested protocols were followed with reaction volumes of 50 μl, with or without the addition of 40 μCi of [$^{35}$S]-methionine (Amersham, Arlington Heights, Ill.) and either 1 μg of pAPPc, pTM3, luciferase control DNA or no DNA added. The reactions were incubated at 30° C. for 90 min. The amount of labeled polypeptide produced was measured in a liquid scintillation counter (Pharmacia, Uppsala, Sweden), and equal counts were run on a SDS-PAGE for confirmation of predicted size polypeptide production.

Murine Connective Tissue Air Pouch Model

This procedure was modified from a previous protocol (Kotwal, G. J., et al. (1998) *Mol. Cell. Biochem.* 185:39–46). 10 μl of unlabeled transcription/translation product from reactions containing either pAPPc (C-100) or pTM3 DNA were mixed with 90 μl 1 M Tris, pH 7.4 (Sigma, St. Louis, Mo.) and incubated at 24° C. for 24 h to allow for fiber formation. After incubation, the mixture was further diluted with an equal volume of Tris buffer, and 100 μl of this dilution was used in each animal. Mouse strains B10.D2/nSnJ (Jackson Laboratory, Bar Harbor, Me.), which produces normal amounts of C5 (C5+/+) and strain B10.D2/oSnJ (Jackson Laboratory), a congenic mouse completely deficient in C5 (C5−/−), were used for all injections.

The mice were physically immobilized, and 1 ml of air was injected into the skin (subcutaneously) of the animal's dorsum to form a connective tissue air pouch. 100 μl of blinded/coded sample of Tris buffer was then injected into the nascent air pouch of an identical strain mouse. The animals were then sacrificed at different time intervals by an overdose of anesthesia. FIG. 8 is a flowchart demonstrating the distribution of animals for injection with various samples and the time points after injection of sacrifice. The time points were selected on the basis of expected times when an in vivo reaction would occur.

The air pouch, consisting of a single cell layer of connective tissue, was surgically harvested, mounted and stained with May-Grunwald/Giemsa (Sigma, St. Louis, Mo.). Photographs of the slides were taken with a Zeiss Universal Research Microscope using a 40× oil immersion objective.

Quantitative Analysis of Connective Tissue Section

Using a 5×5 mm grid mounted in the eyepiece at 400× magnification, 20 grid fields per blinded slide were randomly selected, and all leukocytes within the field were counted and categorized as either monocyte, neutrophil or eosinophil. Although they were present, mast cells were not counted. Average values of all the fields for each of the cell types were calculated, as well as standard deviations, and plotted for comparison.

Determination of Agammaglobulinemic Human Serum Complement Pathway Integrity by Hemolysis Assay X-linked agammaglobulinemic human serum (AHS) described before (Adams, G. et al. (1997) *Pediatr. Infect. Dis. J.* 16:533–534), was serially diluted (1:5, 1:15, 1:30 and 1:60) with dextrose gelatin veronal buffer (DGVB)(Sigma, St. Louis, Mo.) in a total volume of 30 µl. The dilutions were mixed with 200 µl of sensitized sheep red blood cells (SSRBC) (Diamedix, Miami, Fla.) and incubated at 37° C. for one hour. Whole cell s were pelleted by centrifugation at 3000×g for three minutes. The absorbance of lysed cell supernatant was measured at a wavelength of 405 nm using a EL×800 microplate reader (Bio-Tek Instruments, Winoski, Vt.). An increase in absorbance directly correlated with an increase in cell lysis due to complement activation. Hemolysis was seen at the lowest dilutions (1:60) tested, with only a slight decrease in absorbance.

VCP $CH_{50}$ Determination by Hemolysis Assay

The amount of VCP required to reduce complement-induced sSRBC hemolysis by half ($CH_{50}$) was determined using a microplate assay described earlier (Kotwal, G. J. et al. (1990) *Science* 250:827–830). Differing volumes (2, 1, 0.5, 0.1, or 0.01 µl) of VCP were added to 200 µl of sSRBC (Diamedix) and 1 µl of AHS or normal human sera (NHS) in a total volume of 250 µl and, incubated at 37° C. for 1 h. Measurement of equal amounts of water-lysed sSRBCs was taken to be 100% hemolysis, whereas sSRBCs incubated in buffer without serum or VCP served as a negative hemolysis control. After incubation, whole cells were removed by centrifugation at 3000×g for 3 min at room temperature and the supernatant measured for cell lysis at an absorbance of 405 nm on a EL×800 microplate reader. A graph of percent inhibition versus VCP dilutions allowed the $CH_{50}$ to be evaluated.

Measurement of Complement Activation

The ability and quantity of complement activation by Aβ was measured using an enzyme immunoassay specific for the end product of activation of the complement cascade: soluble membrane attack complex (SC5b-9) (Quidel, San Diego, Calif.). Soluble membrane attack complex is a multiprotein complex composed of the activated terminal proteins of complement activation (C5–C8 and several C9). This assay uses an immobilized monoclonal antibody specific for human C9 which captures SC5b-9 formed in solution on the surface of a microliter plate where it can bind a secondary antibody conjugated to horseradish peroxidase. The addition of a chromogenic substrate produces a color change, which can be measured by a plate reader at an absorbance of 405 nm. The manufacturer's suggested protocol was followed under the following conditions. NHS or AHS was diluted to a final concentration of 1–5 and assayed at 1:25 (100 µl total volume). Experimental reactions contained 50 µM Aβ and either 3 µl (VCP $CH_{50}$=0.0.62 µl/1 µl NHS) vaccinia virus complement control protein (VCP) or Minimal Essential Medium (MEM) (Gibco BPL, Gaithersburg, Md.), the same in which VCP was suspended. Positive controls of heat-activated IgG or zymosan were run concurrently to ensure the presence of an intact and functioning complement protein system. Negative controls of NHS or AHS with or without MEM were included for the measurement of background complement activation and to determine whether the media had either a positive or negative influence on the formation of SC5b-9.

Results

Expression of App C-Terminus (C-100) In Vitro

As described in FIG. 5, PCR amplification of pFB68L containing DNA coding for the C-terminal 100 amino acids of APP with primers JD01F and JD01R resuled in a cDNA with newly engineered NcoI and SalI restriction endonuclease sites at its 5' and 3' ends, respectively. A calculated size of 1.1 kbp was confirmed by agarose gel electrophoresis. After digestion with NcoI and SalI, the cDNA and plasmid pTM3 was transformed into competent *E. coli*, amplified, and purified using a maxiprep kit (Qiagen, Chatsworth, Calif.). The pAPPc was sequenced and the precise open reading frame expressed along with the primers used for sequencing is shown in FIG. 7. The pAPPc was then used in an in vitro wheat germ extract coupled transcription/translation reaction. A product of approximately 10 kDa termed C-100 was observed by sodium dodecyl sulfate polyacrylamide gel electrophoresis (SDS-PAGE) and its identity was confirmed as corresponding to the APP C-terminus by immunoprecipitation with antibodies raised against the carboxyl terminus of APP.

Mouse Air Pouch Experiments

Based on encouraging preliminary observations suggesting cellular influx only in the presence of Aβ in a pilot study with eight mice, 32 additional mice were employed to evaluate the effect of Aβ, with the experimenter blinded to the samples being investigated. The number of mice injected in this study and the distribution of animals for injection with different samples are shown in FIG. 8. Thirty-two animals were injected over three different experimental runs with either TBS or Tris as background controls, products from in vitro coupled transcription/translation reactions containing either pTM3 or pAPPc DNA, or fibrillar Aβ peptide. Samples were injected into air pouches in either C5+/+ or C5−/− mice. After injection, an incubation period of either five or 48 h was allowed before the animals were sacrificed and tissues were taken.

After harvesting, mounting and staining the fixed connective tissues, they were examined microscopically for differences in the number and type of inflammatory cells present in each section. Fields were randomly chosen and the number of neutrophils, eosinophils and monocytes were counted within each field and the average and standard deviation were obtained as described in the Methods section.

FIG. 9 is a compilation of the results in graphical form, and represents the averages of the different experimental variations. At 5 h post-injection (FIG. 9A), the numbers of monocytes and eosinophils present in the different spreads were nearly the same. The neutrophil counts, however, showed a significant increase in connective tissue excised from C5+/+ mice injected with C-100. Since neutrophil numbers were not increased in mice injected with in vitro reaction from the control pTM3 vector DNA, it must be the specific C-100 produced only in the in vitro reactions that is stimulating neutrophil influx into the region, and not the reaction mix in general. The possibility that the Aβ fibril formation is enhanced by the coupled transcription-translation reaction cannot be ruled out. Also, no notable neutrophil increase is seen in any of the injected C5−/− mice. This indicates that the inflammatory response present in a few of the mice must be complement-mediated since elimination of a critical fifth component (C5) of the cascade also diminishes cellular influx. Overall, this result seems to be indicative of an early inflammatory response in the presence of complement. In order to determine if the means of the cell count of the C5+/+ mice injected with C-100 or with the control were significantly different, the Mann-Whitney Rank Sum test was performed. The difference in the median values of the 2 groups was greater than would be expected by chance-, there was a statistically significant difference (P<0.001). Similar results were obtained when an unpaired t-test was used. There also seemed to be a significant difference between the male and female mice injected with C-100. At 48 h after injection, monocyte numbers were increased, compared to 5 h (FIG. 2B), whereas neutrophil levels had returned to control levels. The average number of monocytes seen in sections injected with C-100 or Aβ peptide were higher than those seen in tissues injected with either Tris/TBS or pTM3 control. Also, monocyte numbers in C5+/+ mice injected with pAPPc-encoded product or Aβ peptide injected C5+/+ mice were slightly higher than in their C5−/− counterparts.

A general change in the number and type of cells was observed, as is apparent in the composite photo, showing representative fields, from the different experimental situations (FIG. 10). The early response (FIG. 10D) showed an influx of neutrophils to the site of injection when the material injected into C5+/+ was the APP C-terminus. Later, at 48 h, post-injection (FIG. 10H), there seemed to be an increase in the number of mononuclear cells present in experimental sections, but not in controls. At later time points, the number of neutrophils was markedly decreased. Other cell type numbers remained relatively unchanged regardless of what was injected, or the amount of time allowed to pass before the sacrifice of the animal.

In Vitro Activation of Complement by Aβ and Inhibition by VCP

Addition of 50 μM Aβ to twenty-fold diluted NHS resulted in strong activiation of the complement cascade, as measured by formation of SC5b-9 in an enzyme immunoassay. The quantity of activation was extrapolated from control standards with their own internal controls (FIG. 11A) and expressed in ng/ml. External controls of zymosan and heat-activated IgG (HAG) were also used to confirm complement activation by intact alternative and classical pathways, respectively. These external controls exhibited very high levels of activation (FIG. 11A), beyond the measurement of the plate reader under experimental conditions.

When NHS was incubated at 7° C. for 90 min in the presence of 50 μM Aβ, high levels of complement activation were detected in the range of 150–200 ng/ml as compared to insignificant levels in the absence of Aβ (FIG. 11A). Addition of purified VCP to the reaction containing NHS and Aβ consistently resulted in complete inhibition (90% or 9-fold) of complement activation to background levels (FIG. 11B).

When these experiments were repeated, substituting agammaglobulinemic serum for NHS, with an intact complement protein pathway as determined by hemolysis assay (see methods) for NHS, levels of activation very similar to those seen using NHS were observed (FIG. 11C). Addition of VCP to samples incubated with AHS and Aβ again resulted in inhibition of activation. Serum from agammaglobulinemic patients is devoid of IgM and deficient in IgG, but allowed complement activation similar to the serum with normal levels of IgG and IgM. This confirmed earlier observations that activation of complement by Aβ is independent of either IgG or IgM anti-body.

Discussion

Histopathological evidence of AD coupled with in vitro studies showing that Aβ fibrils can cause complement activation via the classical complement pathway point to an immune response as having an important role in disease progression (Cribbs, D. H. et al. (1997) *Neuroreport.* 8:3457–3462, Jiang, H. et al. (1994) *J. Immunol.* 152: 5050–5059; Mann, D. M. A. et al. (1995) *Acta Neuropathol* 90: 472–477; Webster, S. et al. (1997). *J. Neurochem.* 69:388–398). The presence of activated microglia, reactive astrocytes, acute phase proteins and complement factors within and around plaques are all signs of an inflammatory response. It is known that the amyloid deposition is capable of causing activation of the classical pathway of the complement cascade in an antibody-independent manner. The complement system forms one of the first molecular lines of defense against infectious agents. Uncontrolled, it can trigger autoimmune destruction of healthy tissue. Deposition of complexes and formation of immunomodulators by the cascade have been associated with activating microglia (Elkabes, S. et al. (1996): *J. Neurosci.* 16:2508–2521), the macrophages of the brain, which in turn cause a progression and maintenance of the inflammation, by secreting cytokines like IL-I which would attract other immune cells and astrocytes. Local tissue destruction follows, along with a further persistence of a chronic form of inflammation. In direct suggestion for the pivotal role of inflammation in AD is its reduced incidence in patients routinely receiving nonsteroidal anti-inflammatory agents to reduce inflammation due to other causes such as arthritis. The use of anti-complement and anti-inflammatory therapies would greatly augment the treatment of AD (Breitner, J. C. et al. (1995) *Neurobiology aging* 16(4):523–530; Mackenzie, I. R. & Munoz, D. G. (1998) *Neurology* 50(4):986–990; McGeer, P. L. et al. (1996) *Neurology* 47(2):425–432). Prior to the present invention, anti-cholinesterase inhibitors (e.g. tacrine, donepezil), that may also decrease secretion of the amyloid precursor protein, have been the only effective therapy for AD, and only in a limited number of patients.

In these experiments, we have shown that the Aβ fibrils either made from in vitro coupled transcription-translation or from synthetic peptides can, in a mouse model, cause influx of classical inflammatory cells in complement sufficient mice but not in complement deficient mice. This clearly demonstrates that the Aβ fibrils cause complement activation that results in the formation of the potent chemotactic factors C5a and C5b-9 in mice which have C5, but not in mice lacking C5. There also seems to be a differential expression of immune cells, with neutrophils seen soon after the injection of Aβ fibrils containing samples, while the monocytes are seen at later time points such as 48 h. Complement activation studies using the Ig-deficient serum lacking IgM from patients with X-linked agammaglobulinemia confirms earlier observation that the complement activation by Aβ fibrils is antibody-independent or not significantly altered by the presence of normal levels of antibody.

Aβ activates both the classical and alternate complement cascades. Our findings showing that the vaccinia virus complement control protein (VCP), an inhibitor of both the classical and alternate pathways, can block complement activation by Aβ, which thus prevents the release of C5a, is particularly significant. It proves that the novel complement activation by Aβ contributing to cellular influx can indeed be blocked.

EXAMPLE 2

Surface Exposed Conserved K/R-X-K/R Sites and Net Positive Charge on Poxviral Complement Control Proteins Contribute to Heparin Binding and to Inhibition of Molecular Interactions with Human Endothelial Cells The most recently identified property of the multifunctional VCP (vaccinia virus compliment control protein) is its ability to bind heparin. It has been shown in previous studies, as well as this one, to exhibit lysozyme-like heparin binding activity. Because of this activity, VCP can be taken up by mast cells and possibly persist in the tissue for extended periods of time, helping to preserve the viral habitat (Kotwal, G. J., 1998. D. E. 10th International Congress of Immunology 1:315–320.). It has also been shown to reduce chemotactic migration of leukocytes in the presence and absence of the chemokine MIP-1 α (macrophage inflammatory protein-1 alpha). This suggests that VCP can bind to heparin-like molecules lining the surface of endothelial cells, blocking chemokine binding, thereby blocking the chemotactic signal.

In this study, we further characterize the biological significance of VCPs ability to bind heparin. Using flow cytometry, the amount of specific antibody binding to human endothelial cells—in the presence and absence of VCP—was measured. It was found that VCP was able to inhibit antibody binding to major histocompatibility complex class I molecules on human endothelial cells. This suggests that VCP can interfere with molecular interactions with infected cells and could prevent antibody-dependent cell-mediated cytotoxicity as well as other cytotoxic cell interactions with target cells. The ability of VCP to bind heparin-like molecules suggests that it plays many roles and therefore may have a variety of applications. It is for these reasons that we have been interested in obtaining a better understanding of the molecular basis for the VCP-heparin interaction. Through examination of several recombinant VCP (rVCP fragments, it has now been determined that the percentage of positively charged amino acids, overall charge, and the number of putative heparin binding sites are all important factors governing the heparin binding ability of VCP.

Flow microfluorimetric analysis. Human umbilical cord vascular endothelial cells (HUVECs) were obtained from the American Type Culture Collection (Manassas, Va.) at passage thirteen. Monolayer cultures were maintained using F12K Ham's media supplemented with 10% fetal bovine serum (FBS), (Sigma), 30 μg/ml endothelial cell growth supplement (Sigma), and 100 μg/ml heparin (Sigma), at 37° C. in humidified air containing 5% $CO_2$. Cells were cultured to approximately 80% confluency in 75 cm² vented flasks (Flacon, Lincoln Park, N.J.) coated with 1.5% gelatin (Sigma) in phosphate buffer saline. Cells were trypsinized (0.25% trypsin, 1 mM EDTA, Sigma), $4 \times 10^5$ cells/ml were placed in a 6-well flat-bottom culture plates (3.5 cm diameter, Falcon, Lincoln Park, N.J.), coated with 1.5% gelatin, and incubated for 24 h in F12K media without growth factor (Lian et al., 1996. J. Immunol. 157:864–873). For analysis of antibody interaction with cell surface class I HLA-ABC molecules, triplicate wells (2 ml each) were trypsinized and washed with FTA hemagglutination buffer (Becton Dickinson) and stained for 30 min on ice with 0.25 μg of phycoerythrin-conjugated mouse antihuman HLA-ABC monoclonal antibody (Caltag, Burlingame, Calif.), or a mouse IgG2a mAb (an isotype-match negative control) in the presence or absence of 2 or 5 μg of VCP. After incubation, cells were washed three times in FTA buffer, and then fixed in Hank's balanced salt solution (HBSS) containing 2% paraformaldehyde. Before staining, cell cultures were assessed for viability by trypan blue dye exclusion and, in all cases, the cells were found to be >95% viable. The percentage of positively stained cells were determined using a flow cytometer (Becton Dickinson FACScan, San Jose, Calif.) equipped with a single 15-mW argon laser tuned to 488 nm. Forward and 90° angle light scatter and integrated log phycoerythrin and FITC fluorescence signals were collected and analysed. Variability between duplicate samples was less than 10%. To compensate for any background fluorescence, the control threshold was set less than 1% binding of control mAbs. Data were acquired from analysis of >3000 events. A single homogenous cell population was indicated as detected by forward and 90° light scatter.

Cloning of VCP

Fragments of VCP were expressed in *Pichia pastoris* using the secretory expression vector pPIC9. The fragments corresponded to amino acids 18–146 [rVCP SCR (1,2)], 82–204 [rVCP SCR (2,3)], 145–263 [rVCP SCR (3,4)] and 18–262 [rVCP SCR (1–4)] (SCR=short consensus repeats). Genomic DNA from vaccinia virus was used as template for the amplification of the DNA fragments encoding the above protein fragments by PCR. In all cases except for rVCP SCR (3,4) the oligonucleotides used introduced a 5' EcoRI site and a 3' NotI site which were used for cloning the fragments into the expression vector. For rVCP SCR (3,4), cloning was carried out as described earlier (Wiles, P., et al. 1995. *J. Biol. Chem.* 270:25805–25811).

Selection of clones and expression of rVCP SCR (3,4) has been described previously (Wiles, A. P., et al. 1997. *J. Mol. Biol.* 272:253–265). For rVCP SCR (1,2), rVCP SCR (2,3) and rVCP SCR (1–4) clones transformed with the expression vectors described above where selected on the basis of their ability to grow on histidine deficient medium. Small-scale expression screening was performed by inoculating 5 ml of buffered minimal glycerol (BMG) and growing at 30° C. until the $OD_{600}$ reached between 6 and 10. The cells were harvested and resuspended in 2 ml (for KM71 cells) or 15 ml (for GS115 cells) of buffered minimal methanol (BMM). Cells were grown with vigorous shaking for 4 to 5 days with daily addition of methanol to reach a concentration of 0.5%. Media from these inductions was analysed by SDS-PAGE and the highest level expressers selected. For rVCP SCR (1,2), (2,3), and (1–4), the KM71 cell line proved to produce the most protein. For large-scale growth of rVCP SCR (1,2) and rVCP SCR (1–4), 100 ml of BMG was inoculated with 5 ml of an overnight culture and grown at 30° C. with vigorous shaking overnight. This culture was then used to inoculate several liters of BMG. The cultures were grown for 48 hours until the OD reached approximately 20. The cells were spun down and resuspended in the same volume of BMM and grown for 4 to 5 days with vigorous shaking. Cells were fed methanol to a concentration of 1% every 24 hours. For rVCP SCR (2,3), BMG media was inoculated with an overnight culture and grown at 30° C. with vigorous shaking until an OD of approximately 6 had been attained. The pellet was then harvested by centrifugation, resuspended in BMM media (40% of the total BMG volume) and grown for 5 days with daily addition of methanol to a concentration of 0.5%.

Purification of rVCP SCR (3,4) has been described previously (Wiles, A. P., et al. 1997. *J. Mol. Biol.* 272:253–265). For purification of rVCP SCR (1,2), media was concentrated down to a small volume using a combination of a Millipore Prep/Scale-TFF cartridge (3 kDa molecular weight cut-off) and Amicon stirred-cell (with 3 kDa molecular weight cut-off). The sample was exchanged into 50 mM Tris-HCl (pH 9.0) using a Pharmacia PD-10 column and loaded onto a Pharmacia Mono-Q column, equilibrated in the same buffer. The protein was then eluted with a NaCl gradient of 0 to 100% over twenty minutes. Fractions containing rVCP SCR (1,2) were collected and concentrated using Amicon stirred-cell ultrafiltration and then loaded onto a Brownlee Aquapore C4 reverse-phase column and the protein eluted with an acetonitrile gradient. Fractions containing pure rVCP SCR (1,2) were collected and lyophilised. For purification of rVCP SCR (2,3), media was concentrated to approximately 50 ml using an Amicon concentrator (3 kDa cut-off) before being centrifuged at 20,000×g for 1 hour and the pellet discarded. The sample was exchanged into 5 mM sodium acetate (pH 4.0) using a PD-10 column and applied to a Mono-S cation exchange column (Amersham Pharmacia, Uppsala, Sweden), equilibrated in the same buffer. Protein was eluted with a NaCl gradient and fractions corresponding to pure rVCP SCR (2,3) were pooled and lyophilised. For purification of rVCP SCR (1–4), media was concentrated to a small volume by the same means as rVCP SCR (1,2). The protein was exchanged into 20 mM phosphate pH 6 using a PD-10 column and dried.

Heparin Binding Ability

In order to establish a basis for comparison, 10 µg each of bovine serum albumin (BSA), heparin binding protein (HBP)(described earlier (Flodgaard, H., et al. 1991. *Eur. J. Biochem.* 197:535–547)), lysozyme, and MIP-1α were pooled, dissolved in 1 ml of ultapure water, and passed through a 1 ml HiTRAP heparin column and the unbound material collected. The bound proteins were washed with 1 ml of ultrapure water and then eluted with increasing sodium chloride concentrations ranging from 250 mM up to 4.0 M. Next, 20 µg of purified recombinant rVCP SCR (1,2), rVCP SCR (2,3), rVCP SCR (3,4), rVCP or 10 µg of wild type VCP were each dissolved in 1 ml of ultrapure water and passed through separate 1 ml HiTRAP heparin columns and the unbound materials collected. After washing the column with 1 ml of ultrapure water, the proteins were eluted with sodium chloride concentrations ranging from 250 mM to 2.5 M. The fractions were then separated using SDS-PAGE and silver stained. Densitometric readings were taken using the Alphalmager 2000 software system. Finally, 0.5 ml of the fraction containing the protein was concentrated by ultrafiltration and its activity tested using the hemolysis assay.

Sequencing of the VCP Homolog in MPV (Monkeypox Virus)

Sequencing was done as described previously (Shchelkunov, S. N., et al. 1998. *Virology* 243:432–460).

Hemolysis Assay

The biological activity of the proteins were determined by using the hemolysis assay, described earlier (Kotwal, G. J., et al. 1990. Science 250:827–830). In order to more specifically quantitate their activity, each protein was tested as a series of dilutions ranging from 0.5 to 5.0 μg.

Model of VCP

The structure of the two unknown VCP modules (VCP SCR 1 and VCP SCR 2) were modeled by homology with the four known VCP module structures: VCP SCR 3, VCP SCR 4, fH (factor H)SCR 15 and fH SCR 16, using the program MODELLER (Sali, A. and T. L. Blundell. 1993. *J. Mol. Biol.* 234:779–815). Five models of each module were created. The model which was closest to the average structure (as measured by r.m.s.d.) was used in the construction of the VCP SCR (1–4) model. Construction of the VCP SCR (1–4) was undertaken using the molecular visualization package, InsightII (Msi Inc. San Diego, Calif.). This was achieved by simply bonding the two modeled VCP structures to the NMR derived structure of the VCP SCR (3,4) module pair (Wiles, A. P., et al. 1997. *J. Mol. Biol.* 272: 253–265). No attempt was made to accurately model the junctions between modules 1 and 2 and modules 2 and 3. Rather, torsion angles in the two residues linking the module pairs were set to give a relatively extended conformation.

Results:

In order to determine the biological consequences of heparin binding by VCP, we tested whether VCP was able to block functional molecular interactions with human vascular endothelial cells. Flow cytometric analysis of HUVECs treated with mouse monoclonal antibodies to human MHC class I molecules—in the presence and absence of VCP—show that VCP is able to modulate antibody binding in a dose-dependent manner. As shown in FIG. 12, addition of 5 μl (2 μg) of VCP to antibody treated HUVECs, reduced antibody binding from 91.5% down to 75.4%. An additional 15 μl (5 μg total) of VCP reduced antibody binding from 91.5% to 61.0%—suggesting that it is blocking in a dose-dependent manner.

To calibrate the HiTRAP heparin column, several proteins having different binding affinities for heparin were passed through the column and eluted with increasing sodium chloride concentrations. SDS PAGE analysis of the eluted fractions containing these proteins of various heparin-binding abilities can be seen in FIG. 13. Analysis suggests that BSA does not bind heparin, since it is present only in the unbound and wash fractions. Lysozyme and MIP-1 α, which bound heparin with moderate and equal affinity, were contained within the 500 mM and 750 mM sodium chloride fractions. HBP, showing the highest affinity for heparin, was eluted by a sodium chloride concentration of 2.0 M.

In order to better characterize the heparin binding ability of the VCP molecule, VCP, recombinant VCP, and various recombinant segments of VCP were passed through HiTRAP heparin columns and analyzed using SDS PAGE, shown in FIG. 14. The results suggest that the full-length natural and recombinant proteins bind heparin with close to or equal affinity as lysozyme and MIP-1 α; both VCP and rVCP were concentrated primarily in the 500 mM and 750 mM sodium chloride fractions. PAGE analysis of the various recombinant VCP segments revealed even more interesting data. Recombinant rVCP SCR (1,2) and rVCP SCR (3,4) bound heparin with the same strength as the full-length protein, eluting once again at 500 mM and 750 mM. While recombinant rVCP SCR (2,3), on the other hand, did not bind heparin at all and was found primarily in the unbound and wash fractions. The activity of the purified proteins was then tested using the hemolysis assay. The results indicate that only the full-length protein inhibits lysis of sensitized sheep red blood cells—anywhere from 60 to 90% inhibition. The rVCP segments showed no inhibition of lysis; suggesting that the whole protein is needed to block complement activation. Although, the naturally truncated VCP homolog produced by monkeypox virus (MPV (shown in FIGS. 15 and 16), which lacks almost the entire fourth SCR, has been shown to inhibit hemolysis of sensitized sheep red blood cells. Thus, indicating that it is blocking the classical pathway of complement activation.

To more precisely identify the molecular basis behind the VCP-heparin interaction, the amino acid sequences were analyzed using the MacVector software system. Putative heparin binding sites (K/R-X-K/R) were first identified—shown in FIG. 15 along with the sequence alignment of different pox virus VCP homologs—and predicted to be located on the surface of the protein. The amino acid sequences were then scanned to determine the total number of positive amino acids (K+R), the percentage made up of these positively charged amino acids (% K+R), and overall pI of the protein—the results are summarized in FIG. 15. All of the proteins shown to bind heparin had an overall pI of greater than 7.0, and more importantly, were made up of greater than 9% positively charged amino acids. The results also suggest that SCR 1 and SCR 4 contribute the most to this interaction. Although the results show there is no simple answer to how VCP binds heparin, it is clear that the overall positive charge, number of putative binding sites, and the percentage of positive amino acids making up the protein, have a significant effect on its ability to interact with and bind heparin.

Discussion:

The ability of VCP to bind heparin sulfate proteoglycan molecules adds a new dimension to its role in modulating the host immune response. In previous studies, the ability of VCP to bind heparin was found to permit uptake by mast cells—possibly allowing for tissue persistence over extended periods of time. In addition, earlier studies have shown that binding to heparin-like molecules on the surface of endothelial cells can block chemokine adherence, resulting in reduced chemotactic signaling. In this study, flow cytometry was used to demonstrate that VCP can interfere with antibody binding to endothelial cells. More importantly, this study demonstrates that addition of VCP significantly decreases the amount of antibody able to attach to HUVECs in a dose-dependent manner. It is postulated that VCP, binding to heparin-like molecules on the surface of endothelial cells, prevents antibody adherence. This binding may therefore block antibody attachment through stearic interference, and block both molecular and cellular interactions—which are dependent on target cell adhesion molecules binding to cytotoxic cells. Furthermore, this novel mechanism can enable virus infected cells or the antigen presenting cell from destruction by host defense mechanism. Thus VCP enables orthopoxviruses, all of which encode homologs of VCP, to evade the immune system by multiple mechanisms, e.g. by blocking complement pathways, blocking antibody-dependent cytotoxic cell activity (ADCC) or by interfering with attachment of cytotoxic T cells to virus infected cells. In addition, as explained below, VCP can inhibit alternative pathway activation in a manner similar to factor H, another heparin binding protein.

Due to the apparent importance heparin binding has in many of the biological activities exhibited by VCP, we became interested in better characterizing the molecular reasons for this interaction. Recombinant segments of VCP—each representing two of the four SCRs—were generated by genetic engineering vaccinia virus DNA, encoding VCP, into the *Pichia pastoris* expression system. The ability of these recombinant segments to bind heparin was then tested. It was determined that recombinant proteins rVCP SCR (1,2) and rVCP SCR (3,4) retained the same binding affinity as the full-length native protein. While recombinant protein rVCP SCR (2,3) retained no heparin binding ability at all. In order to explain this, the amino acid sequences of the recombinant protein segments were more closely examined. It was determined that the number, and more importantly, the percentage of positively charged amino acids making up the protein contributed greatly to its ability to interact with heparin. Also, the overall charge and number of putative binding sites (K/R-X-K/R) making up the protein, appears to play a role in heparin binding. For the most part, the ability of VCP to bind heparin lies in its first and fourth SCR. These two short consensus repeats possess within them the highest percentage of positive amino acids, the greatest number of putative binding sites, and have a very strong overall positive charge.

In order to better visualize the positioning of heparin binding sites in the VCP molecule, a model was developed using four VCP module structures: VCP SCR 3, VCP SCR 4, factor H (fH) SCR 15 and fH SCR 16 see FIG. 17. AS can be seen in this model, heparin binding exists primarily at the ends—SCRs one and four. The middle of the molecule therefore does not contribute any to the binding (hence VCP SCR (2,3) showed no ability to bind).

It is clear that the ability to bind polyanions, such as heparin, is crucial for the function of many immune-regulating proteins. Factor H (fH), for example, binds to the polyanion sialic acid on the surface of mammalian cells, preventing activation of the alternative pathway. Like VCP, fH is made up of SCRs, two of which have been shown to have heparin binding abilities (Blackmore, T. K., et al. 1998. *J. Immunol.* 160:3342–3348). It is postulated that these heparin-binding domains are responsible for binding sialic acid, thereby preventing alternative pathway activation. The heparin binding regions of many other proteins exhibiting heparin binding activity have been mapped (Cardin, A. D., et al. 1991. *Methods Enzymol.* 203:556–83:556–583; Cardin, A. D. and H. J. Weintraub. 1989. *Arteriosclerosis* 9:21–32; Marino, M., et al. 1999. *J. Biol. Chem.* 274: 30377–30386; Sendak, R. A. and A. Bensadoun. 1998. *J. Lipid Res.* 39:1310–1315.; Wong, P., et al. 1995. *J. Biol. Chem.* 270:25805–25811). In most cases (including ours), binding is the result of dense regions of positively charged amino acids. These arginine and/or lysine rich regions vary in sequence and length among heparin binding proteins. Interestingly, the heparin binding sequence used by VCP and its homologs is short and relatively conserved.

In summary, by examining the heparin-binding ability of VCP, we have gained a better understanding of the molecular basis by which this interaction occurs. In addition, the data presented here further enhances our understanding of this truly unique, yet compact, multifunctional viral protein. It resembles in structure and function giant complex human complement regulatory proteins human C4b binding protein (C4b-BP) and the complement receptor 1 (CR1), respectively. Not only is VCP a miniature version of these large molecules, it has retained all the complement modulating functions, and as we have described here, added a number of additional functions to its repertoire due to its ability to bind heparin-like molecules. This better understanding may some day help in the exploitation of VCP's possible therapeutic properties in the treatment of inflammatory conditions such as restonosis, systemic lupus erythematosus, xenograft transplant rejections, and Alzheimer's Disease, the latter particularly in view of the know ability of heparin-binding proteins to stimulate neurite outgrowth in vitro (Cheng, K. W. 1992 *Neurosci. Lett.* 142:77–80).

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for reducing Aβ-induced inflammation in a patient in need of such treatment comprising administering an effective amount of a pharmaceutical composition comprising a protein with the amino acid sequence of SEQ ID NO:1, or a pharmaceutically acceptable salt thereof, and a pharmaceutically acceptable carrier therefor.

2. A method according to claim 1, wherein the carrier is aqueous.

3. A method according to claim 1, wherein the composition further comprises an cholinesterase inhibitor.

4. A method according to claim 3, wherein the cholinesterase inhibitor is selected from the group consisting of ambenonium, adrophonium, methylphysostigmine, neostigmine, pyridostigmine, and pharmaceutically acceptable salts thereof.

5. A method according to claim 3, wherein the cholinesterase inhibitor is an acetylcholinesterase inhibitor.

6. A method according to claim 5, wherein the acetylcholinesterase inhibitor is selected from the group consisting of tacrine, galanthamine, and pharmaceutically acceptable salts thereof.

* * * * *